US008877505B2

(12) United States Patent
May et al.

(10) Patent No.: US 8,877,505 B2
(45) Date of Patent: Nov. 4, 2014

(54) COMPOSITION AND METHOD FOR STABILIZING FLUORESCENT PARTICLES

(75) Inventors: Eric May, Chandler, AZ (US); Alexandra Nagy, Oro Valley, AZ (US); Jerome Kosmeder, Tucson, AZ (US)

(73) Assignee: Ventana Medical Systems, Inc., Tucson, AZ (US)

(*) Notice: Subject to any disclaimer, the term of this patent is extended or adjusted under 35 U.S.C. 154(b) by 244 days.

(21) Appl. No.: 13/382,509

(22) PCT Filed: Feb. 1, 2011

(86) PCT No.: PCT/US2011/023383
§ 371 (c)(1),
(2), (4) Date: Jan. 5, 2012

(87) PCT Pub. No.: WO2011/097248
PCT Pub. Date: Aug. 11, 2011

(65) Prior Publication Data
US 2012/0122094 A1   May 17, 2012

Related U.S. Application Data
(60) Provisional application No. 61/337,363, filed on Feb. 2, 2010.

(51) Int. Cl.
G01N 21/64     (2006.01)
C12Q 1/68      (2006.01)
G01N 33/533    (2006.01)
C09K 11/02     (2006.01)
G01N 33/58     (2006.01)
B82Y 15/00     (2011.01)

(52) U.S. Cl.
CPC ............ *C09K 11/025* (2013.01); *G01N 33/533* (2013.01); *G01N 33/588* (2013.01); *B82Y 15/00* (2013.01); *Y10S 977/774* (2013.01); *Y10S 977/902* (2013.01)
USPC .............................. 436/18; 977/774; 977/902

(58) Field of Classification Search
None
See application file for complete search history.

(56) References Cited

U.S. PATENT DOCUMENTS

| 6,649,138 | B2 | 11/2003 | Adams et al. |
| 6,682,596 | B2 | 1/2004 | Zehnder et al. |
| 6,815,064 | B2 | 11/2004 | Treadway et al. |
| 7,118,627 | B2 | 10/2006 | Hines et al. |
| 7,250,082 | B2 | 7/2007 | Jang et al. |
| 7,253,014 | B2 | 8/2007 | Barron et al. |
| 7,682,789 | B2 | 3/2010 | Chen et al. |
| 7,790,481 | B2 | 9/2010 | Takeuchi et al. |
| 7,985,557 | B2 | 7/2011 | Kosmeder et al. |
| 2003/0177941 | A1 | 9/2003 | Barbera-Guillem |
| 2005/0147974 | A1 | 7/2005 | Muller-Schulte |
| 2006/0003394 | A1 | 1/2006 | Song |
| 2006/0246523 | A1 | 11/2006 | Bieniarz et al. |
| 2008/0057513 | A1 | 3/2008 | Farrell |
| 2008/0212866 | A1 | 9/2008 | Lett et al. |
| 2009/0098057 | A1 | 4/2009 | Zheng |
| 2009/0176253 | A1 | 7/2009 | Bieniarz et al. |

FOREIGN PATENT DOCUMENTS

| EP | 2 085 782 | 8/2009 |
| JP | 2009-108126 | 5/2009 |
| WO | WO 2005/001889 | 1/2005 |
| WO | WO 2009/149013 | 12/2009 |
| WO | WO 2010/022332 | 2/2010 |

OTHER PUBLICATIONS

Boldt et al., "Comparative Examination of the Stability of Semiconductor Quantum Dots in Various Biochemical Buffers," *The Journal of Physical Chemistry*, 110:1959-1963, 2006.
Bullen et al., "The Effects of Chemisorption on the Luminescence of CdSe Quantum Dots," *Langmuir*, 22:3007-3013, 2006.
Dannhauser et al., "Photophysics of Quantized Colloidal Semiconductors Dramatic Luminescence Enhancement by Binding of Simple Amines," *The Journal of Physical Chemistry*, 90:6074-6076, 1986.
Freeman et al., "Self-assembly of semiconductor quantum-dots on electrodes for photoelectrochemical biosensing," www.rsc.org/publishing/journals/PP/article.asp?doi=b612435f, 1 page, 2009.
International Search Report and Written Opinion of the International Searching Authority, mailed Aug. 16, 2011, for corresponding International Application No. PCT/US2011/023383, 16 pages.
Landes et al., "Photoluminescence of CdSe Nanoparticles in the Presence of a Hole Acceptor: n-Butylamine," 105:2981-2986, 2001.
Lees et al., "The Preparation of Colloidally Stable, Water-Soluble, Biocompatible, Semiconductor Nanocrystals with a Small Hydrodynamic Diameter," *ACSNANO*, 3(5):1121-1128, 2009.

(Continued)

*Primary Examiner* — Anand Desai
(74) *Attorney, Agent, or Firm* — Klarquist Sparkman, LLP

(57) ABSTRACT

Embodiments of a composition for stabilizing fluorescent signal of nanoparticles and methods for its use are disclosed. In some embodiments, the composition has a pH from 7 to 10 and includes borate, protein and/or protein hydrolysate, an amine, a preservative, and a nonionic surfactant. In particular embodiments, the amine is an N-ethanol substituted amine, such as ethanolamine, diethanolamine, triethanolamine, N-methyldiethanolamine, N,N-dimethylethanolamine, or a combination thereof. In some embodiments, a fluorescent particle solution, such as a quantum dot solution or quantum dot conjugate solution, is diluted in the composition and stored at 4° C. In certain embodiments, the fluorescence intensity of the diluted fluorescent particle remains substantially the same when stored at 4° C. for at least one month or at least three months. In particular embodiments, a diluted quantum dot conjugate is used to detect a hybridized probe or a protein antigen.

26 Claims, 18 Drawing Sheets

(56) References Cited

OTHER PUBLICATIONS

Li-Qun et al., "Effect of Amino Acid on the Fluorescence of CdTe Quantum Dots," *Acta Phys.-Chim. Sin.*, 24(4):725-728, 2008 (English abstract).

Liu et al., "pH-sensitive Photoluminescence of CdSe/ZnSe/ZnS Quantum Dots in Human Ovarian Cancer Cells," *J Phys. Chem. C Nanomater Interfaces*, 111(7):2872-2878, 2007.

Nose et al., "Chemical role of amines in the colloidal synthesis of CdSe quantum dots and their luminescence properties," *Journal of Luminescence*, 126:21-26, 2007.

"Qdot® Mouse IgG2a Isotype Control Conjugates," *Molecular Probes® invitrogen detection technologies*, 1 page, 2008.

"Qdot® Streptavidin Conjugates," *Molecular Probes® invitrogen detection technologies*, pp. 1-15, 2007.

Travert-Branger et al., "Oligomeric PEG-Phospholipids for Solubilization and Stabilization of Fluorescent Nanocrystals in Water," *Langmuir*, 24:3016-3019, 2008.

Xie J., "Ultra-high surface fibrous membranes from electrospinning of natural proteins: casein and lipase enzyme," *Journal of Materials Science*, 3:2125-2133, 2003.

Zhu et al., "Compatibility of quantum dots with immunobuffers, and its effect on signal/background of quantum dot-based immunoassay," *Anal Bioanal Chem*, 9 pages, 2009.

COMPOSITION AND METHOD FOR STABILIZING FLUORESCENT PARTICLES

CROSS REFERENCE TO RELATED APPLICATIONS

This is the U.S. National Stage of International Application No. PCT/US2011/023383, filed Feb. 1, 2011, which was published in English under PCT Article 21(2), which in turn claims the benefit of U.S. Provisional Application No. 61/337,363, filed Feb. 2, 2010, each of which is incorporated herein in its entirety by reference.

FIELD

This disclosure concerns the composition and use of a novel stabilization buffer for storing fluorescent particles.

BACKGROUND

Biological specimens, such as tissue sections from human subjects, can be treated with a stain containing an organic fluorophore conjugated to an antibody which binds to protein, protein fragments, or other targets in the specimen. The stained specimen is then illuminated with light and the fluorophore fluoresces. A digital camera attached to a microscope is used to capture an image of the specimen. The areas where the fluorophore/antibody combination are bound to the target of interest (e.g., protein produced by cancerous cells) appear as colored regions in the image of the specimen, with the color of the area being dictated by the fluorescence spectrum of the fluorophore applied to the specimen. In addition to the visible spectrum, the fluorescence signal may be detected in the infrared or ultraviolet regions, depending on the emission spectrum of the particular fluorophore. A stain containing two or more fluorophores can also be applied to the specimen. These methods have a variety of uses, including diagnosis of disease, assessment of response to treatment, and development of new drugs to fight disease.

More recently, quantum dots have been developed as a detection material for biological staining and imaging applications. Quantum dots (Qdot™ nanocrystals or Qdots™) are nano-crystalline luminescent semiconductor materials. Quantum dots provide several advantages over traditional organic fluorophores for use in biological staining applications. These advantages include narrow emission band peaks, broad absorption spectra, intense signals and relative fluorescent signal stability. However, the fluorescence intensity of quantum dots and quantum dot conjugates in solution is historically unstable if stored under incompatible conditions.

SUMMARY

Compositions for stabilizing fluorescent signal and usage of nanoparticles, such as quantum dots (Qdot™ nanocrystals) and Qdot™ conjugates are disclosed. Storing nanoparticles in the disclosed compositions, for example, minimizes particle aggregation and provides conditions compatible with fluorescence. As a result, small amounts can be used in automated and manual procedures while still maintaining sensitivity and specificity of the nanoparticle and/or nanoparticle conjugate in an assay format.

Embodiments of a novel composition for stabilizing fluorescent particles, such as quantum dots and quantum dot conjugates, and methods for its use are disclosed. Certain disclosed embodiments of the composition include a) a substituted amine other than an amino acid or an alkyl-substituted alkyl amine or (b) an amine and a protein and/or protein hydrolysate, wherein at least one of the amine or the protein and/or protein hydrolysate is present at a concentration effective to stabilize and/or increase fluorescence of a fluorescent particle stored in the composition. In some embodiments, the composition has a pH in the range of 7-10 and includes 0.02 M to 0.5 M borate, 0.05 wt % to 1.5 wt % protein and/or protein hydrolysate, 25 mM to 200 mM alkyl amine, 0.05 wt % to 0.2 wt % preservative, and 0.005 wt % to 0.05 wt % surfactant.

In certain embodiments, the amine is a substituted amine having the formula $R_nNH_{(3-n)}$, where n=1, 2, or 3, each R is independently an aliphatic group, a heteroaliphatic group, an aryl group, a heteroaryl group, an alkyl aryl group, or an aryl alkyl group, and at least one R is substituted. In some embodiments, at least one R is substituted with one or more —OH, —OR$_1$, —CO$_2$R$_1$, —CN groups, or combinations thereof, where R$_1$ is a substituted or unsubstituted aliphatic or aryl group.

In some embodiments, the amine is a primary, secondary or tertiary amine. In some embodiments, the alkyl amine is an alkanolamine. In certain embodiments, the amine is an N-ethanol substituted amine, such as ethanolamine, diethanolamine, triethanolamine, N-methyldiethanolamine, N,N-dimethylethanolamine, or a combination thereof.

In some embodiments, the protein and/or protein hydrolysate is vegetable tryptone, salmon peptone, casein acid hydrolysates, casein base hydrolysates, chicken albumin hydrolysate, gelatin from fish skin, or a combination thereof. In certain embodiments, the preservative is a) sodium azide, b) a preservative composition comprising 9.5-9.9% 2-methyl-4-isothiazolin-3-one, c) a preservative composition comprising 2.3% 5-chloro-2-methyl-4-isothiazolin-3-one, 0.7% 2-methyl-4-isothiazolin-3-one, 2-3% alkyl carboxylate as a stabilizer, and 93-95% modified glycol, or d) a combination thereof. In some embodiments, the surfactant is a non-ionic surfactant, such as Tween® 20 (polyethylene glycol sorbitan monolaurate), Triton® X-100 (polyethylene glycol p-(1,1,3,3-tetramethylbutyl)-phenyl ether)) or Brij 35 (polyoxyethyleneglycol dodecyl ether)

In a particular embodiment, the composition has a pH of 8 to 8.5 and includes 50 mM borate, 1.05% (w/w) casein hydrolysates, 50 mM triethanolamine, 0.08 wt % sodium azide, and 0.005 wt % polyethylene glycol sorbitan monolaurate.

Embodiments of a method for using the novel composition also are disclosed. In some embodiments, a fluorescent particle solution, such as a quantum dot solution or quantum dot conjugate solution, is diluted in the composition to produce a diluted fluorescent particle solution, and the diluted fluorescent particle/composition solution is stored at a temperature below ambient temperature to increase the shelf life of the fluorescent particle. In some embodiments, fluorescence of the suspended fluorescent particle is stabilized for at least one month, at least two months, at least three months, or at least six months. In certain embodiments, the fluorescence intensity of a quantum dot or quantum dot conjugate suspended in an embodiment of the disclosed compositions remains substantially the same when the suspended fluorescent particle is stored for at least one month at 4° C. In particular embodiments, the fluorescence intensity of a quantum dot or quantum dot conjugate suspended in an embodiment of the disclosed storage compositions remains substantially the same for at least three months at 4° C. For purposes of comparison, the same quantum dot or quantum dot conjugate stored without the disclosed composition, for example in an alternative or prior art composition, exhibits a significant decrease in fluorescence intensity after one month at 4° C.

In certain embodiments, a fluorescent particle stored in the composition has an increased fluorescence at a given time point relative to fluorescence of the particle stored in an embodiment of the composition lacking one or more of the alkyl amine, the protein, the surfactant, and/or the preservative. In some embodiments, initial fluorescence is increased. In other embodiments, increased fluorescence occurs at a time subsequent to initial formulation. In some embodiments, increased fluorescence is sustained for at least 5 hours, at least 25 hours, at least 100 hours, at least 250 hours, at least 750 hours, at least 1500 hours, at least 3,000 hours, or at least 4300 hours (i.e., six months). In particular embodiments, the fluorescence of a quantum dot or quantum dot conjugate is increased from 5% to 20%, from 5% to 15%, at least 5%, at least 10%, at least 15%, or at least 20% when suspended in an embodiment of the disclosed storage compositions compared to the quantum dot or quantum dot conjugate suspended in an alternative or prior art composition. In certain embodiments, fluorescence intensity, at a time subsequent to mixing the fluorescent particle with the composition, is increased at least 5% relative to fluorescence intensity of the fluorescent particle in a composition devoid of (a) a substituted amine other than an amino acid or an alkyl-substituted alkyl amine or (b) an amine and a protein and/or protein hydrolysate.

In some embodiments, a probe is hybridized to a target to provide a hybridized probe, e.g., in a fluorescence in situ hybridization (FISH) assay. A quantum dot-antibody conjugate suspended in the disclosed storage composition is used to detect the hybridized probe. In some embodiments, a quantum dot-antibody conjugate is used to detect protein antigens on tissue, e.g., in a fluorescence immunohistochemistry (IHC) assay. In some embodiments, the quantum dot-antibody conjugate concentration is 0.5 nM to 150 nM, 1 nM to 125 nM, 5 nM to 100 nM, 25 nM to 75 nM, 1 nM, 5 nM, 10 nM, 25 nM, 50 nM, 75 nM, or 100 nM in the disclosed composition. In certain embodiments, the quantum dot-antibody conjugate concentration is 50 nM in the disclosed composition.

The foregoing and other objects, features, and advantages of the invention will become more apparent from the following detailed description, which proceeds with reference to the accompanying figures.

DETAILED DESCRIPTION

I. Terms and Definitions

Figure 1:
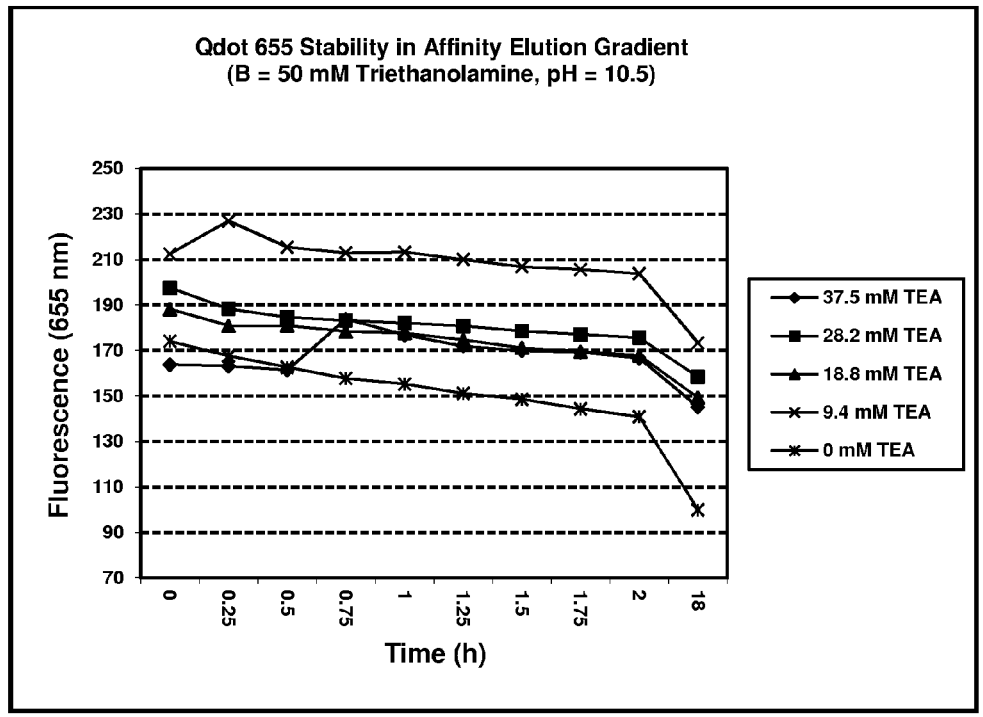
FIG. 1 is a graph of fluorescence light units at 655 nm versus time for Qdot™ 655-30N nanocrystals in an affinity elution gradient with 50 mM triethanolamine at pH 10.5.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited. It is further to be understood that all nucleotide sizes or amino acid sizes, and all molecular weight or molecular mass values, given for nucleic acids or polypeptides or other compounds are approximate, and are provided for description.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

The term aliphatic means having a branched or unbranched carbon chain. The chain may be saturated (having all single bonds) or unsaturated (having one or more double or triple bonds). The chain may be linear or cyclic (i.e., cycloaliphatic).

Alkyl: A hydrocarbon group having a saturated carbon chain. The chain may be branched or unbranched, and may be linear or cyclic (i.e., cycloalkyl). The term lower alkyl means the chain includes 1-10 carbon atoms.

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any chordate such as a vertebrate, for example, in mammals such as humans, goats, rabbits and mice) and fragments thereof that specifically bind to a molecule of interest (or a group of highly similar molecules of interest) to the substantial exclusion of binding to other molecules. An "antibody" typically comprises a polypeptide ligand having at least a light chain or heavy chain immunoglobulin variable region that specifically recognizes and binds an epitope of an antigen. Immunoglobulins are composed of a heavy and a light chain, each of which has a variable region, termed the variable heavy ($V_H$) region and the variable light ($V_L$) region. Together, the $V_H$ region and the $V_L$ region are responsible for binding the antigen recognized by the immunoglobulin. Exemplary immunoglobulin fragments include, without limitation, proteolytic immunoglobulin fragments [such as $F(ab')_2$ fragments, Fab' fragments, Fab'-SH fragments and Fab fragments as are known in the art], recombinant immunoglobulin fragments (such as sFv fragments, dsFv fragments, bispecific sFv fragments, bispecific dsFv fragments, $F(ab)'_2$ fragments, single chain Fv proteins ("scFv"), and disulfide stabilized Fv proteins ("dsFv"). Other examples of antibodies include diabodies, and triabodies (as are known in the art), and camelid antibodies. "Antibody" also includes genetically engineered molecules, such as chimeric antibodies (for example, humanized murine antibodies), and heteroconjugate antibodies (such as, bispecific antibodies). See also, *Pierce Catalog and Handbook, 1994-1995* (Pierce Chemical Co., Rockford, Ill.); Kuby, J., *Immunology*, $3^{rd}$ Ed., W.H. Freeman & Co., New York, 1997.

Aromatic or aryl compounds typically are unsaturated, cyclic hydrocarbons having alternate single and double bonds. Benzene, a 6-carbon ring containing three double bonds, is a typical aromatic compound.

Bioconjugate or Conjugate: A compound having a nanoparticle, such as a quantum dot, and a biomolecule effectively coupled to the nanoparticle, either directly or indirectly, by any suitable means. For example, the biomolecule can be covalently or noncovalently (e.g. electrostatically) coupled to the nanoparticle. Indirect attachment of the biomolecule to the nanoparticle also is possible, such as by using a "linker" molecule, so long as the linker does not negatively affect the luminescence of the quantum dot or the function of the biomolecule. The linker preferably is bio-compatible. Common molecular linkers known in the art include a primary amine, a thiol, streptavidin, neutravidin, biotin, or similar compounds.

Biomolecule: Any molecule that may be included in a biological system, including but not limited to, a synthetic or naturally occurring protein or fragment thereof, glycoprotein, lipoprotein, amino acid, nucleoside, nucleotide, nucleic acid, oligonucleotide, DNA, RNA, carbohydrate, sugar, lipid, fatty acid, hapten, antibody, and the like.

Blocking protein: A protein or protein hydrolysate composition used to decrease the background nonspecific binding (i.e., nonspecific probe attachment or protein binding) in hybridization and detection reactions. Examples of blocking proteins include, but are not limited to, casein, casein hydrolysates, vegetable tryptone, vegetable protein hydrolysate, soy protein hydrolysate, peptone, casein peptone, salmon peptone, gelatin, gelatin hydrolysate, goat globulin protein, chicken albumin, and bovine serum albumin.

Conjugating, joining, bonding or linking: Coupling a first unit to a second unit. This includes, but is not limited to, covalently bonding one molecule to another molecule, non-covalently bonding one molecule to another (e.g., electrostatically bonding) (see, for example, U.S. Pat. No. 6,921, 496, which discloses methods for electrostatic conjugation), non-covalently bonding one molecule to another molecule by hydrogen bonding, non-covalently bonding one molecule to another molecule by van der Waals forces, and any and all combinations of such couplings.

Detectable Label: A detectable compound or composition that is attached directly or indirectly to another molecule, such as an antibody or a protein, to facilitate detection of that molecule. Nanoparticles are a non-limiting example of a class of detectable labels.

Detergent or Surfactant: A detergent or surfactant is a surface-active agent that concentrates at nonpolar liquid-polar liquid interfaces (e.g., oil-water) and exerts an emulsifying action. Detergents are classified as anionic, cationic, or nonionic, depending on their mode of chemical action. Nonionic detergents function via a hydrogen-bonding mechanism. Further, surfactants or detergents reduce interfacial tension between two liquids. A surfactant molecule typically has a polar or ionic "head" and a nonpolar hydrocarbon "tail." Upon dissolution in water, the surfactant molecules aggregate and form micelles, in which the nonpolar tails are oriented inward and the polar or ionic heads are oriented outward toward the aqueous environment. The nonpolar tails create a nonpolar "pocket" within the micelle. Nonpolar compounds in the solution are sequestered in the pockets formed by the surfactant molecules, thus allowing the nonpolar compounds to remain mixed within the aqueous solution.

Fluorescence: A type of luminescence in which an atom or molecule absorbs energy and then emits visible light as it transitions from a higher to a lower electronic state. The term "fluorescence" is restricted to phenomena in which the time interval between absorption and emission of energy is extremely short, e.g., $10^{-9}$ to $10^{-7}$ sec.

Fluorescence in situ hybridization (FISH): FISH is a technique used to detect and localize the presence or absence of specific nucleic acid sequences, such as DNA sequences on chromosomes. FISH uses fluorescently labeled probes that bind to only those parts of the chromosome with which they show a high degree of sequence similarity under defined reaction conditions. FISH also can be used to detect particular mRNA sequences within tissue samples.

Fluorophore: The functional group, or portion, of a molecule that causes the molecule to fluoresce when exposed to an excitation source. The term "fluorophore" also is used to refer to fluorescent compounds used to mark proteins with a fluorescent label.

Heteroaliphatic compounds are aliphatic compounds having at least one heteroatom, i.e., one or more carbon atoms has been replaced by another atom, typically, nitrogen, oxygen, or sulfur.

Heteroaryl compounds are aromatic compounds having at least one heteroatom, i.e., one or more carbon atoms in the ring has been replaced with an atom having at least one lone pair of electrons, typically nitrogen, oxygen, or sulfur.

Nanoparticle or nanocrystal: A nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. A nanoparticle can produce a detectable signal, for example, through absorption and/or emission of photons (including radio frequency and visible photons) and plasmon resonance.

Photoluminescence: A process in which an atom or molecule absorbs photons and is excited to a higher energy state. The atom or molecule then returns to a lower energy state by emitting a photon. Two type of photoluminescence are fluorescence and phosphorescence. Fluorescence is characterized by an extremely short time period (e.g., $10^{-8}$ to $10^{-3}$ second) between absorption and emission. Phosphorescence is a slow process of transition back to a lower energy state after excitation has ceased, sometimes lasting minutes or hours. As used herein in regard to quantum dots, photoluminescence refers to fluorescence.

Quantum dot: A nanoscale particle that exhibits size-dependent electronic and optical properties due to quantum confinement. Quantum dots have, for example, been constructed of semiconductor materials (e.g., cadmium selenide and lead sulfide) and from crystallites (grown via molecular beam epitaxy), etc. A variety of quantum dots having various surface chemistries and fluorescence characteristics are commercially available from Invitrogen by Life Technologies, Inc. (Carlsbad, Calif.) (see, for example, U.S. Pat. Nos. 6,815, 064, 6,682596 and 6,649,138, each of which patents is incorporated by reference herein). Quantum dots are also commercially available from, e.g., Evident Technologies (Troy, N.Y.) and Ocean NanoTech, LLC (Springdale, Ariz.). Other quantum dots include alloy quantum dots such as ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN quantum dots (alloy quantum dots and methods for making the same are disclosed, for example, in US Publication No. 2005/0012182 and PCT Publication WO 2005/001889).

Stable/stabilizing: As used herein with respect to a fluorescent particle, the term "stable" means having substantially no loss in fluorescence intensity over a period of time, such as one or more hours, one or more days, one or more weeks, or one or more months. Stabilizing a fluorescent particle means placing the fluorescent particle in a composition that prevents or reduces diminishing fluorescence intensity of the fluorescent particle over a period of time, or even increases the fluorescent particle's fluorescence intensity, as compared to fluorescence intensity of the fluorescent particle in the absence of the composition.

Substituted: Refers to a molecule or group in which one or more atoms have been replaced by a functional group, an atom other than hydrogen, or a radical. For example, an amine has the general formula $R_nNH_{(3-n)}$ where n=1, 2, or 3, wherein each R is independently an aliphatic group, a heteroaliphatic group, an aryl group, a heteroaryl group, an alkyl aryl group, an aryl alkyl group. A substituted amine refers to an amine in which at least one hydrogen on one R group has been replaced by a functional group, an atom other than hydrogen, or a radical. For instance, a substituted alkyl amine refers to an alkyl amine in which one or more hydrogens on the alkyl chain has been replaced by another atom or functional group. Ethanolamine is one example of a substituted alkyl amine, where a hydrogen atom of the ethyl chain has been replaced by —OH.

II. Quantum Dots

Chromogenic and/or fluorescent semiconductor nanocrystals, also often referred to as quantum dots, can be used as detectable labels. Nanocrystalline quantum dots are semiconductor nanocrystalline particles, and without limiting the present invention to use with particle light emitters of a particular size, typically range from 2-10 nm in size.

Quantum dots typically are stable fluorophores, often are resistant to photo bleaching, and have a wide range of excitation wavelengths with a narrow emission spectrum. Quantum dots having particular emission characteristics, such as emissions at particular wavelengths, can be selected such that plural different quantum dots having plural different emission characteristics can be used to identify plural different targets. Quantum dot bioconjugates are characterized by quantum yields comparable to the brightest traditional fluorescent dyes available. Additionally, these quantum dot-based fluorophores absorb 10-1000 times more light than traditional fluorescent dyes. Emission from the quantum dots is narrow and symmetric, which means that overlap with other colors is minimized, resulting in minimal bleed-through into adjacent detection channels and attenuated crosstalk, which can lead to the simultaneous multiplexing of differentially emitting quantum dots for detection purposes. Symmetrical and tunable emission spectra can be varied according to the size and material composition of the particles, which allows flexible and close spacing of different quantum dots without substantial spectral overlap. In addition, their absorption spectra are broad, which makes it possible to excite all quantum dot color variants simultaneously using a single excitation wavelength, thereby minimizing sample autofluorescence.

Furthermore, it has been found that pegylation, the introduction of polyethylene glycol groups onto the quantum dot conduits, can substantially decrease non-specific protein:quantum dot interaction. Certain quantum dots are commercially available, such as from Life Technologies, Inc. Several working embodiments utilize quantum dot nanoparticles, such as Qdot™565 and Qdot™800 nanocrystals, where the number used in such nomenclature refers to the approximate wavelength of the nanoparticle's emission maximum. For example, a Qdot™565 nanocrystal emits light having a wavelength of 565 nm and produces a light-green color. Thus, quantum dots can be selected to provide a detectable signal at a particular wavelength. Detection is performed through a variety of means, for example a fluorescent microscope, fluorometer, fluorescent scanner, etc., depending on a given application.

III. Quantum Dot Conjugates

Quantum dot use has been limited by their lack of biocompatibility. New advances in surface coating chemistry, however, have helped to overcome these problems. See, for example, Wu, X. et al. Immunofluorescent labeling of cancer marker Her2 and other cellular targets with semiconductor quantum dots, *Nature Biotechnol.* 21, 41-46 (2003); Jaiswal, J. K., Mattoussi, H., Mauro, J. M. & Simon, S. M. Long-term multiple color imaging of live cells using quantum dot bioconjugates, *Nature Biotechnol.* 21, 47-51 (2003); and Dubertret, B. et al. In vivo imaging of quantum dots encapsulated in phospholipid micelles. *Science* 298, 1759-1762 (2002).

Quantum dots also have been conjugated to biorecognition molecules, Id., such as streptavidin. These conjugates have been used for target detection on both fixed cells and tissue sections. In addition, cell-surface proteins and the endocytic compartments of live cells have been detected with quantum dot bioconjugates.

Quantum dots can be conjugated to biomolecules, e.g., an amino acid, peptide/protein, or nucleoside/nucleotide/nucleic acid. Specific exemplary biomolecules useful for making bioconjugates include, without limitation: monoclonal or polyclonal antibodies, such as IgA, IgD, IgE, IgG, IgM; antibody fragments that specifically bind to a molecule of interest (or a group of highly similar molecules of interest) to the substantial exclusion of binding to other molecules including, without limitation, proteolytic antibody fragments (such as $F(ab')_2$ fragments, Fab' fragments, Fab'-SH fragments and Fab fragments as are known in the art), recombinant antibody fragments (such as sFv fragments, dsFv fragments, bispecific sFv fragments, bispecific dsFv fragments, $F(ab)'_2$ fragments, single chain Fv proteins ("scFv"), and disulfide stabilized Fv proteins ("dsFv"). Other useful biomolecules include diabodies, triabodies, and camelid antibodies; genetically engineered antibodies, such as chimeric antibodies, for example, humanized murine antibodies); heteroconjugate antibodies (such as bispecific antibodies); streptavidin; receptors; enzymes; BSA; polypeptides; aptamers; and combinations thereof.

Bioconjugates comprising quantum dots and biomolecules, are commercially available. Alternatively, quantum dot bioconjugates can be synthesized. Methods for making biomolecules/quantum dot conjugates are generally known in the art, and useful bioconjugates can be made by any suitable method.

Figure 35:
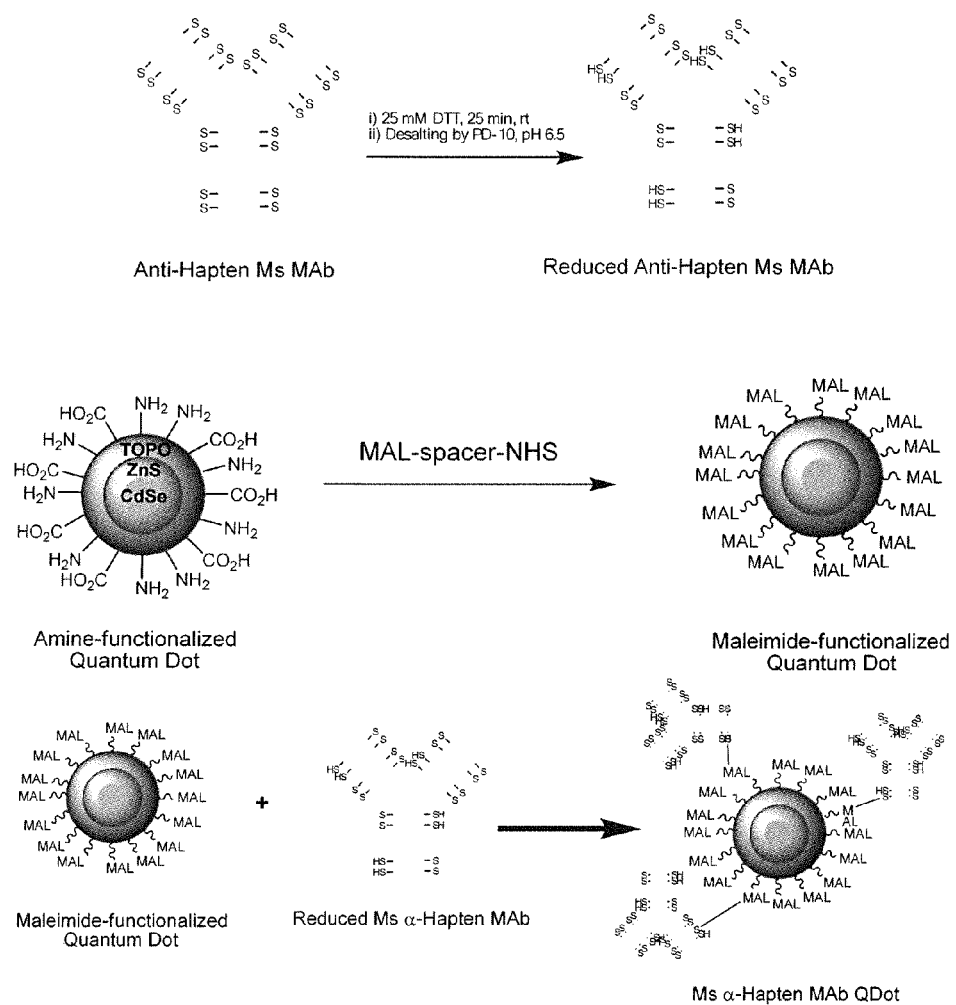
FIG. 35 is a schematic drawing illustrating an exemplary process for making certain disclosed quantum dot bioconjugates.

For example, an immunoglobulin can be incorporated into a CdSe/ZnS quantum dot shell by: 1) reducing native disulfides by treatment with dithiothreitol (DTT); 2) functionalizing amine-terminated, quantum dot capping groups with a suitable heterobifunctional NHS ester-(spacer)$_x$-maleimide (x=4, 8, 12); 3) derivatizing maleimide-terminated quantum dots with these thiolated immunoglobulins; and 4) purifying the conjugates using suitable techniques, such as size-exclusion chromatography. The process is depicted in FIG. 35.

A streptavidin conjugate can be made by substituting a thiolated streptavidin for the thiolated immunoglobulin in the process, e.g., a streptavidin molecule treated with 2-iminothiolane.

The quantum dots used in the above examples are protected by an electrostatically bound organic shell of trioctyl phosphine oxide (TOPO) and an intercalating amphiphilic polymer to induce water solubility. This polymer has approximately 30 terminal amine groups for further functionalization. See E. W. Williams, et. al., "Surface-Modified Semiconductive and Metallic Nanoparticles Having Enhanced Dispersibility in Aqueous Media", U.S. Pat. No. 6,649,138 (incorporated by reference herein). In order to form highly sensitive quantum dot conjugates, antibodies can be attached to the quantum dots with varying ratios. The chemistry is similar to that described in U.S. Patent Publication Nos. 2006/0246523 and 2009/0176253, which are incorporated by reference herein in their entireties.

IV. Quantum Dot Detection

Standard fluorescence microscopes are a tool for detecting quantum dots and quantum dot bioconjugates. Since quantum dot bioconjugates are virtually photo-stable, time can be taken with the microscope to find regions of interest and adequately focus on the samples. Quantum dot bioconjugates are useful any time bright photo-stable emission is required and are particularly useful in multicolor applications where only one excitation source/filter is available and minimal crosstalk among the colors is required. For example, quantum dots have been used to form conjugates of streptavidin and IgG to label cell surface markers and nuclear antigens and to stain microtubules and actin (Wu, X. et al. (2003), *Nature Biotech*, 21, 41-46).

As an example, fluorescence can be measured with the multispectral imaging system Nuance™ (Cambridge Research & Instrumentation, Woburn, Mass.). As another example, fluorescence can be measured with the spectral imaging system SpectraView™ (Applied Spectral Imaging, Vista, Calif.). Multispectral imaging is a technique in which spectroscopic information at each pixel of an image is gathered and the resulting data analyzed with spectral image-processing software. For example, the Nuance™ system can take a series of images at different wavelengths that are electronically and continuously selectable and then utilize the images with an analysis program designed for handling such data. The Nuance™ system is able to obtain quantitative information from multiple dyes simultaneously, even when the spectra of the dyes are highly overlapping or when they are co-localized, or occurring at the same location in the sample, provided that the spectral curves are different. Many biological materials autofluoresce, or emit lower-energy light when excited by higher-energy light. This signal can result in lower-contrast images and data. High-sensitivity cameras without multispectral imaging capability increase the autofluorescence signal along with the fluorescence signal. Multispectral imaging can unmix, or separate out, autofluorescence from tissue and thereby increase the achievable signal-to-noise ratio.

V. Fluorescent Particle Storage

The fluorescence intensity of stored fluorescent particles, such as quantum dots and quantum dot conjugates in solution, decreases over time. For example, Qdot™-antibody conjugates that have been stored in commercially available buffers for a period of time have reduced fluorescence signal intensity in FISH assays compared to freshly prepared Qdot™-antibody conjugate solutions. Without being limited to a theory of operation, the loss in signal intensity is potentially due to either aggregation of the conjugates and/or loss of the nanomaterial's quantum yield.

Disclosed herein are embodiments of a novel composition, which stabilizes and reduces the relative fluorescence loss for fluorescent particles in solution. In some embodiments, the composition can stabilize the fluorescence intensity of a quantum dot or quantum dot conjugate over a time period of at least one month when the quantum dot or quantum dot conjugate is stored in the composition at a temperature less than ambient temperature, such as at 4° C. This particular storage temperature is cited not to limit the method to storing at a particular temperature, but rather to provide a basis for comparing stabilized versus non-stabilized compositions. In some embodiments, the fluorescence intensity may remain substantially the same when the fluorescent particle is stored in a disclosed embodiment of the composition for several weeks or months at 4° C. In certain embodiments, stabilizing the fluorescent particle means that there is less than 50% loss, less than 30% loss, less than 20% loss, less than 10% loss, less than 5% loss, less than 1% loss, 5% to 30% loss, 5% to 20% loss, 1% to 10% loss, 1% to 5% loss, or even 0% loss in relative fluorescence intensity when the fluorescent particle is stored in a disclosed embodiment of the composition for at least one day, at least one week, at least one month, at least two months, at least three months, or at least six months at 4° C. For example, in certain embodiments the relative fluorescence intensity remains substantially the same after storage in the composition for one month at 4° C. In a particular embodiment, the composition can stabilize the fluorescence intensity for at least three months when a quantum dot-antibody conjugate is stored in the composition at 4° C. In a working example, the relative fluorescence intensity of a quantum dot-antibody conjugate remained substantially the same after a three-month period of storage at 4° C. Thus, in some embodiments, fluorescence of the suspended fluorescent particle is stabilized for at least one month, at least two months, at least three months, or at least six months. For purposes of comparison, the same quantum dot or quantum dot conjugate stored without the disclosed composition, for example in an alternative or prior art composition, exhibits a significant decrease in fluorescence intensity after one month at 4° C., and may exhibit complete loss of fluorescence after a few months, e.g., after three months. The stabilization compositions as disclosed herein also allow for automated methods in a diluted fashion on a platform.

In certain embodiments, the composition can increase the fluorescence intensity of a fluorescent particle relative to a comparable composition lacking one or more of the amine, the protein, the surfactant, and/or the preservative. In some embodiments, initial fluorescence is increased. In other embodiments, increased fluorescence is seen at a time subsequent to initial formulation. In some embodiments, fluorescence remains increased for at least 5 hours, at least 25 hours, at least 100 hours, at least 250 hours, at least 750 hours, at least 1500 hours, at least 3,000 hours, or at least 4300 hours (i.e., 6 months). In particular embodiments, the fluorescence of a quantum dot or quantum dot conjugate, relative to the same conjugate not dispersed in the composition, is increased typically at least 5%, such as from 5% to 20%, from 5% to 15%, at least 5%, at least 10%, at least 15%, or at least 20%.

While investigating potential affinity chromatography elution conditions for Qdot™ conjugates, it was initially discovered that elution buffers containing tertiary alkyl amines containing ethanol substituents stabilized the relative loss of fluorescence for Qdot™ nanoparticles in solution. This influence was further demonstrated in a wide variety of buffers. Several different amines (1°, 2° and 3°) with various functionalities were investigated and provided similar effects. However, based on initial results, trialkanolamines, such as triethanolamine, provided the greatest fluorescence stabilization at elevated temperatures of 37° C. and 45° C. Chromatography eluents containing high salt concentration (e.g., 2 M NaCl, 2.25 M KI or 2.5 M $MgCl_2$), high organic concentration (e.g., 25% aqueous polyethylene glycol), or highly acidic conditions (e.g., 50 mM citric acid, pH=3.0) were shown to greatly diminish the Qdot™ photoluminescence.

Compositions were tested to determine their ability to stabilize Qdot™ fluorescence. Certain disclosed embodiments included an amine, a buffer, blocking protein, a preservative, and a surfactant. An initial Qdot™ stabilization buffer (QSB) composition was formulated. This initial QSB composition included 0.32 M borate (pH 8.3), 1.05 wt % casein base hydrolysates, 50 mM triethanolamine, 0.08 wt % sodium azide preservative (available from Sigma-Aldrich, St. Louis, Mo.), and 0.005 wt % Tween® 20 surfactant (available from Sigma-Aldrich, St. Louis, Mo.). Each QSB component was evaluated to determine its effect on Qdot™ stability. Additionally, the QSB was evaluated to determine its effects on staining efficiency in fluorescence in situ hybridizations (FISH).

A. Amine

Addition of an amine to a Qdot™ stabilization buffer composition can stabilize the fluorescence of a Qdot™ nanocrystal or Qdot™ conjugate over time. Without being bound by any particular theory of operation, it is believed that the amine may passivate quantum dot surface defects, thus increasing the luminescence quantum yield of the quantum dot. The amine can be a primary, secondary, or tertiary amine, such as an aliphatic amine, a heteroaliphatic amine, an aryl amine, a heteroaryl amine, an alkyl aryl amine, an aryl alkyl amine, or a cyclic amine (e.g., cyclohexylamine, pyridine). The amine has a general formula, $R_nNH_{(3-n)}$, where n=1, 2, or 3, and each R is independently an aliphatic group, a heteroaliphatic group, an aryl group, a heteroaryl group, an alkyl aryl group, or an aryl alkyl group. Each R can be substituted or unsubstituted. In some embodiments, at least one R is substituted with, for example, one or more —OH, —OR$_1$, —CO$_2$R$_1$, or —CN groups, or a combination thereof, where R$_1$ is a substituted or unsubstituted aliphatic or aryl group. The amine also can be a substituted or unsubstituted cyclic amine, e.g., cyclohexylamine. Typically, the amine is a substituted amine, particularly a substituted alkyl amine other than an amino acid or an alkyl-substituted alkyl amine. In some embodiments, the amine is an unsubstituted lower alkyl amine or a substituted lower alkyl amine other than an amino acid or an alkyl-substituted lower alkyl amine (e.g., 1-methylbutylamine). In certain embodiments, the substituted alkyl group is a lower alkyl alcohol or lower alkyl nitrile. For example, the substituted alkyl group may be ethanol or propionitrile. A secondary or tertiary amine may include a combination of alkyl and/or substituted alkyl groups. In particular embodiments, the amine includes an alkanol group, such as an N-ethanol group. Exemplary amines with an N-ethanol group include ethanolamine, diethanolamine, triethanolamine, N-methyldiethanolamine, N,N-dimethyl-ethanolamine, N,N-bis(2-hydroxyethyl)glycine, and bis(2-hydroxyethyl)amino-tris(hydroxymethyl)-methane.

It was determined that, for disclosed embodiments, amines containing an N-ethanol substituent (e.g., ethanolamine, diethanolamine, triethanolamine, N-methyldiethanolamine, or N,N-dimethylethanolamine) provided the greatest fluorescence stabilization. Thus, the hydroxyl functional group, and similar groups such as —OR$_1$ and —CN facilitate fluorescent stability. Although ethanol-substituted amines provided similar effects at 4° C. and room temperature (e.g., 25° C.), triethanolamine provided the greatest fluorescence stabilization at elevated temperatures of 37° C. and 45° C. for disclosed embodiments.

The amine may be used in Qdot™ stabilization buffer compositions in any effective amount, such as an amount greater than zero up to at least 200 mM, typically from 25 mM to 200 mM, more typically 38 mM to 75 mM. In some embodiments, the amine is present at a concentration less than or equal to 200 mM, such as 25-200 mM, 50-100 mM, or 38-75 mM. In certain embodiments, the QSB composition includes 25-200 mM of an ethanol-substituted amine. For example, the composition may include 50 mM ethanolamine, diethanolamine, triethanolamine, N-methyldiethanolamine, N,N-dimethyl-ethanolamine, or a combination thereof. In a particular embodiment, the composition includes 50 mM triethanolamine.

In certain embodiments, QSB compositions comprising an amine increase fluorescence of a quantum dot or quantum dot conjugate stored in the QSB composition. In some embodiments, an initial increase in fluorescence (e.g., as measured with a spectral scanning multimode plate reader) is seen compared to a QSB composition without an amine. In certain embodiments, the increased fluorescence persists for at least 25 hours after initial formulation.

B. Buffer Salt, Concentration and pH

Various buffer systems were investigated to determine their compatibility with quantum dots. The effects of buffer pH also were evaluated.

Buffers with elevated pH values (e.g., greater than or equal to pH 7) and moderate salt concentrations (e.g., from 0.02 M to 0.5 M) have been found to stabilize at least some Qdot™ nanocrystals and Qdot™-antibody conjugates. Any buffer that stabilizes fluorescence for a period of time, and does not interfere with imaging results, can be used. Exemplary buffers for storing quantum dots include borate buffers, phosphate-buffered saline (PBS), Tris-buffered saline (TBS), and combinations thereof. Suitable, commercially available buffers may include FortéBio Kinetics Buffer additive (added to 10×PBS, pH 7.4, FortéBio, Inc., Menlo Park, Calif.), and Pierce SEA BLOCK (a steelhead salmon serum-based blocking formulation in PBS buffer with 0.1% sodium azide). In certain embodiments, borate buffers at an approximate concentration of 0.4 M (e.g., 0.42 M borate, pH 8.3), 10×PBS (pH 7.5, 100 mM phosphate, 150 mM sodium chloride), FortéBio Kinetics Buffer additive (added to 10×PBS, pH 7.4), Solution A, and Pierce SEA BLOCK were found to stabilize Qdot™ fluorescence.

In some embodiments, compositions comprising a buffer and an amine are further compatible with Qdot™ fluorescence. In particular embodiments, the amine is an N-ethanol substituted amine, e.g., triethanolamine. For example, 0.4 M borate with 50 mM TEA (pH 8.6) and 10×PBS with 50 mM TEA (pH 8.3) demonstrate improved Qdot™ stability compared to 0.4 M borate or 10×PBS alone.

Borate buffer was selected as a suitable exemplary Qdot™ stabilization buffer, and the effects of salt concentration and pH were evaluated. Photoluminescence is known to decrease in some buffers with a high salt concentration (e.g., greater than 2 M). Without being bound by any particular theory of operation, high salt concentrations may facilitate diffusion of small molecules through the phospholipid outer layer of a polymer-coated quantum dot, resulting in a decrease or complete loss of photoluminescence or quantum yield. Thus, moderate salt concentrations, greater than zero to about 2 M, may be more suitable for Qdot™ stabilization.

In some embodiments, for example, a borate concentration of 0.02 M to 0.5 M, or 0.05 M to 0.32 M, is compatible with Qdot™ fluorescence. In certain embodiments, salt concentrations at the lower end of the range are compatible with quantum dots and associated proteins, and aggregation is minimized. In a particular embodiment, Qdot™ fluorescence was more compatible when the borate concentration was 0.32 M compared to other buffer formulations.

A buffer composition with an acidic pH was found to reduce Qdot™ photoluminescence relative to compositions having a neutral or basic pH. For example, a 50 mM citric acid solution, pH 3.0, was shown to greatly diminish photoluminescence. Thus, a pH greater than or equal to 7 is preferentially suitable for storing Qdot™ nanocrystals and Qdot™-antibody conjugates. A pH greater than 10.5, however, may be unsuitable for long-term stability of antibodies. Hence, in some embodiments, the composition has a pH of 7 to 10, such as 7 to 9.5, 7 to 9, 7.5 to 9.5, 8 to 9, or 8 to 8.5.

C. Protein

Addition of nonspecific proteins, protein hydrolysates, or peptides i.e., "blocking proteins," to fluorescence in situ hybridization assays has been shown to reduce background signal and improve detection of a hybridized probe or antibody conjugate. Some commercially available buffers include blocking proteins. For example, FortéBio Kinetics Buffer additive includes 0.1 mg/mL BSA (bovine serum albumin). Solution A, includes 1.5 wt % casein base hydrolysates. It is advantageous to include proteins, protein hydrolysates, or peptides in a Qdot™ storage composition to stabilize fluorescence.

Any protein concentration that facilitates Qdot™ stability and does not interfere with imaging can be used. However, if the protein concentration is too high, protein aggregation may occur and reduce the fluorescence intensity of a Qdot™ nanocrystal or Qdot™-antibody conjugate. Thus, a suitable composition includes sufficient protein to stabilize fluorescence intensity and reduce background signal during subsequent assays, while maintaining a protein concentration that minimizes aggregation. In some embodiments, a QSB composition includes from greater than zero to at least 2 wt %, such as from 0.05 wt % to 1.5 wt %, 1.0 wt % to 1.1 wt %, or 0.06 wt % to 0.60 wt % protein, protein hydrolysates, or peptides. Further, a person of ordinary skill in the art will recognize the importance of utilizing a filtered protein source so as not to introduce aggregated proteins into the system.

Numerous sources of proteins, protein hydrolysates, and peptides are commercially available. Suitable sources may include vegetable tryptone, casein hydrolysates, gelatin, salmon peptone, goat globulin protein, chicken albumin hydrolysate, or combinations thereof. In some embodiments, vegetable tryptone, casein acid hydrolysates, casein base hydrolysates, gelatin from fish skin, or a combination thereof is used. Thus, in certain embodiments, a QSB composition includes vegetable tryptone, casein acid hydrolysates, casein base hydrolysates, gelatin from fish skin, or combinations thereof, in a concentration from greater than zero to at least 2 wt %, such as from 0.5 wt % to 1.5 wt %, such as 0.05 wt % to 1.1 wt %, 1.0 wt % to 1.1 wt %, 0.06 wt % to 0.60 wt %, or 0.25 wt % to 0.55 wt %.

In certain embodiments, inclusion of a protein in the QSB composition stabilizes fluorescence of a quantum dot or quantum dot conjugate stored in the QSB composition. Without being bound by any particular theory, proteins, protein hydrolysates, or peptides may stabilize fluorescence of quantum dots or quantum dot conjugates by forming micelles around the quantum dots or conjugates, thereby minimizing aggregation and maintaining solubility of the quantum dots or conjugates.

D. Surfactant

Addition of a surfactant to a QSB composition may reduce aggregation of protein and Qdot™-antibody conjugates. Surfactants may form micelles surrounding Qdot™-antibody conjugates in an aqueous solution, and hinder aggregation processes, thus stabilizing Qdot™ fluorescence.

Some ionic detergents, such as sodium dodecyl sulfate, were detrimental to the relative quantum yields of Qdot™ nanoparticles. In some embodiments, nonionic detergents were found to stabilize Qdot™ fluorescence. Suitable nonionic detergents include, for example, aliphatic glycols, particularly alkylene glycols (such as Tween® 20 (polyethylene glycol sorbitan monolaurate) and Triton® X-100 (polyethylene glycol p-(1,1,3,3-tetramethylbutyl)-phenyl ether)), oxygenated alkylene glycols (such as Brij 35 (polyoxyethyleneglycol dodecyl ether)), and alcohol ethoxylates (such as Tergitol™ 15-S-9, a secondary alcohol ethoxylate, available from Dow Chemical Company). In certain embodiments, 0.05 wt % Brij 35 in 50 mM borate buffer, pH 8.3, was shown to stabilize the fluorescence intensity of Qdot™ nanocrystals or Qdot™ conjugates.

To determine the effect of surfactant concentration, Tween® 20 was evaluated over a range of 0.0025 wt % to 0.20 wt % in 50 mM borate buffer, pH 8.3. Concentrations from 0.005 wt % to 0.050 wt % demonstrated greater fluorescence stability than lower or higher concentrations. Triton® X-100 was effective at similar concentrations. Thus, in some embodiments, the QSB composition may include a nonionic detergent with a concentration of from greater than zero to 0.05 wt %, such as 0.005 wt % to 0.05 wt %, or 0.005 wt % to 0.01 wt %.

In certain embodiments, inclusion of a surfactant in the QSB composition increases fluorescence stability of a quantum dot or quantum dot conjugate stored in the QSB composition.

E. Preservative

In some embodiments, the QSB composition includes a preservative, such as an antibacterial agent. Suitable preservatives include, for example, isothiazolinones, glycols, azides, and combinations thereof. Exemplary preservatives include ProClin® 300 (2.30% 5-chloro-2-methyl-4-isothiazolin-3-one, 0.70% 2-methyl-4-isothiazolin-3-one, 2-3% alkyl carboxylate (a stabilizer), and 93-95% modified glycol; available from Sigma-Aldrich, St. Louis, Mo.), ProClin® 950 (9.5-9.9% 2-methyl-4-isothiazolin-3-one, Sigma-Aldrich), and sodium azide. Based upon other commercial buffer compositions, 0.01 wt % ProClin® 300 was selected initially and evaluated. However, the low concentration did not provide adequate antibacterial protection in the Qdot™ stabilization buffer. A concentration of 0.05 wt % was found to be an effective preservative, but resulted in decreased fluorescence of Qdot™ nanocrystals.

Sodium azide also was evaluated as a potential preservative and compared to ProClin® 300. Compositions including 0.05 wt % ProClin® 300 or 0.08 wt % sodium azide were evaluated with eight different Qdot™ nanocrystals. Although the relative change in fluorescence varied among the Qdot™ nanocrystals, the overall loss in fluorescence was less when the composition included sodium azide as compared to when the composition included ProClin® 300. Similar results were obtained with Qdot™-antibody conjugates.

Thus, in some embodiments, the QSB composition includes a preservative. In certain embodiments, the QSB composition includes an effective amount of sodium azide, such as a concentration of from f greater than zero to 0.2 wt %, such as 0.05 wt % to 0.2 wt %, or 0.05 wt % to 0.1 wt %. In a particular embodiment, the QSB composition includes 0.08 wt % sodium azide.

F. Qdot™ Stabilization Buffer

Certain disclosed embodiments of a Qdot™ stabilization buffer composition include a salt (0.02 M to 0.5 M), an amine (25-200 mM), a protein (0.05 wt % to 1.5 wt %), a surfactant (0.005 wt % to 0.05 wt %), and a preservative (0.05 wt % to 0.1 wt %). The QSB composition has a pH in the range of 7 to 9. In some embodiments, the salt is borate (0.02 M to 0.5 M), the amine is an N-ethanol substituted amine (50-100 mM), and the pH is in the range of 8 to 9. In particular embodiments, the QSB composition includes 0.32 M borate, 50 mM triethanolamine, 1.1 wt % protein (e.g., casein acid hydrolysates, casein base hydrolysates, chicken albumin hydrolysates, vegetable tryptone, salmon peptone, gelatin from fish skin, or combinations thereof), 0.08 wt % sodium azide, and 0.005 wt % surfactant (e.g., Tween® 20, Triton® X-100 or Brij 35), with a pH of 8-8.5.

A study of several Qdot™-antibody conjugates in deconstructed QSB compositions (i.e., compositions in which one component was removed) demonstrated that the complete QSB composition (0.32 M borate buffer (pH=8.3), 50 mM TEA, 1.05 wt % casein base hydrolysates, 0.08 wt % sodium azide, and 0.005 wt % Tween® 20) provided the best overall fluorescence stability for the conjugates. The presence of protein in the buffer had the largest effect on fluorescence stability. (See Example 9, Table 22.)

However, at least some of the components may have a synergistic effect when used in combination. For example, in 10 mM PBS buffer, the addition of either 50 mM triethanolamine (buffer pH=9.3) or 1.05 wt % casein base hydrolysates (buffer pH=7.8) had little effect on the fluorescence stability of Qdot™655-30N nanocrystals compared to 10 mM PBS buffer (pH=7.4) alone. (See, e.g., Example 3, Table 6.) However, when both 50 mM triethanolamine and 1.05 wt % casein base hydrolysates were added to the buffer (pH=9.1), a relative fluorescence decrease of only 2.6% was seen after 50 hours as compared to a 16.1% relative fluorescence decrease in 10 mM PBS alone. In 0.32 M borate buffer (pH=8.3), the Qdot™655-30N nanocrystals exhibited a fluorescence decrease of 23.6%. Addition of 50 mM TEA (final buffer pH=8.8) produced a fluorescence decrease of 14.1%, and addition of 1.05 wt % casein base hydrolysates (buffer pH=8.5) produced a decrease of only 6.4%. However, the addition of TEA and casein base hydrolysates to 0.32 M borate buffer (pH=9.0) resulted in significantly increased stability with a relative fluorescence decrease of only 0.3% after 50 hours. Indeed, the change in quantum yield of the nanocrystals was minimal even after 4 months. The synergistic effect of the combined buffer components provide a compatible environment for the nanocrystals such that aggregation is minimized and nanocrystal fluorescence is preserved.

G. Applications

The fluorescence of Qdot™-antibody conjugates in commercially available buffers decreases over time. For example, Qdot™-antibody conjugates (Qdot™565-30N-MsAntiHapten) diluted in Solution A and used in a fluorescence in situ hybridization assay exhibited a noticeable loss in fluorescence intensity after one month in storage at 4° C. (See Example 11B.) Qdot™-antibody conjugates diluted in an embodiment of the disclosed QSB composition, however, exhibited no loss in fluorescence after three months in storage and exhibited only a slight loss in fluorescence after four months in storage. Thus, some embodiments of the Qdot™ stabilization composition stabilize the fluorescence intensity of Qdot™-antibody conjugates for at least one month, at least two months, at least three months, or at least four months in storage at 4° C.

Embodiments of the disclosed QSB composition are suitable for storing Qdot™-antibody conjugates used in fluorescence in situ hybridization (FISH) wherein the conjugate is used to detect a labeled probe hybridized to tissue and/or fluorescence immunohistochemistry (IHC) applications wherein the conjugate is used to detect protein antigens on tissue. In some embodiments, the quantum dot-antibody conjugate concentration is stored at a concentration of 0.5 nM to 150 nM, 1 nM to 125 nM, 5 nM to 100 nM, 25 nM to 75 nM, 1 nM, 5 nM, 10 nM, 25 nM, 50 nM, 75 nM, or 100 nM in the disclosed QSB composition. In certain embodiments, the quantum dot-antibody conjugate concentration is stored at a concentration of 50 nM in the disclosed QSB composition.

VI. Examples

Example 1

Effect of Triethanolamine on Qdot™ Stability

The relative fluorescent stability of Qdot™655-30N nanocrystals and their antibody bioconjugates was examined in solution for various chromatography elution conditions at room temperature. A 50 µL aliquot of a 50 nM solution of the Qdot™ nanocrystal in affinity binding buffer (10 mM PBS, 150 mM NaCl, 10 mM EDTA at pH=7.0) was suspended in a 150 µL aliquot of a mixture of an aqueous triethanolamine (TEA, pH=10.5) solution and affinity binding buffer.

Figure 2:
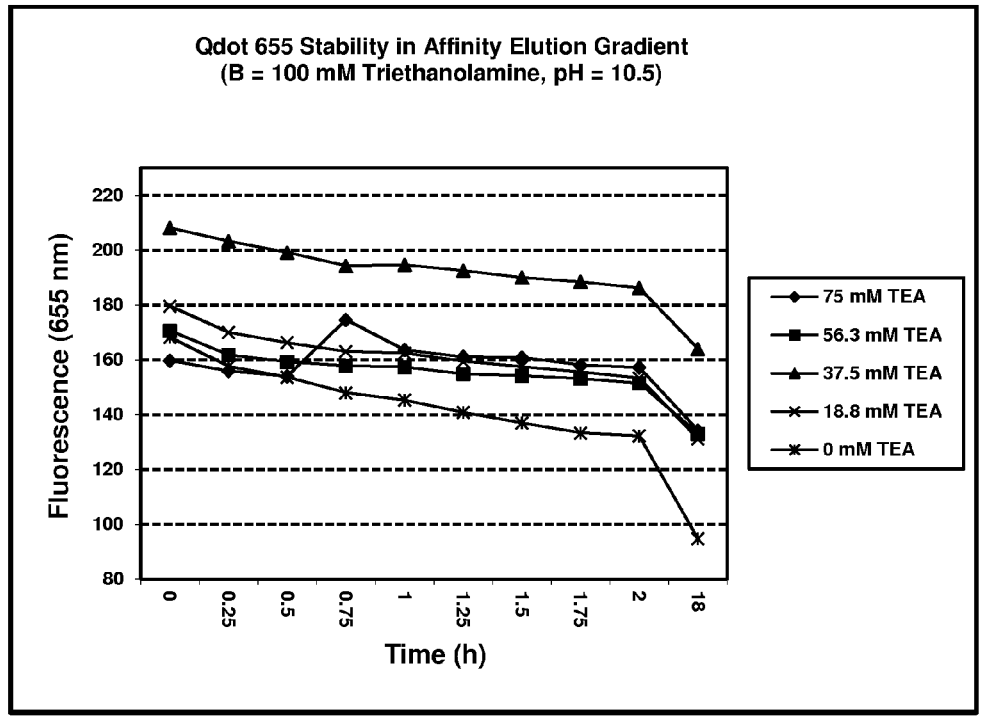
FIG. 2 is a graph of fluorescence light units at 655 nm versus time for Qdot™ 655-30N nanocrystals in an affinity elution gradient with 100 mM triethanolamine at pH 10.5.

The relative fluorescence of the Qdot™ solution was monitored as a function of time using a Thermo Varioskan spectral scanning multimode plate reader (available from Thermo Fisher Scientific, Waltham, Mass.) with a $\lambda_{ex}$=400 nm and 525 nm with a $\lambda_{em}$=655 nm. Four 200 µL replicates of the 50 nM Qdot™655-30N nanocrystals solution were monitored in a low-binding plate (i.e., a plate including a surface that minimizes cell attachment, protein absorption, enzyme activation and cellular activation). The fluorescence was graphed versus time (FIGS. 1-2) and reported as a percent change at set time points (Table 1). The values in Table 1 are the percent loss in fluorescence at 655 nm at 18 hours. The elution buffer contains variable concentrations of TEA (as found in Table 1) at pH 10.5.

TABLE 1

| [TEA] in Elution Buffer (B) | Elution Gradient (% B) | 0% | 25% | 50% | 75% | 100% |
|---|---|---|---|---|---|---|
| 25 mM | Concentration TEA (mM) | 0.0 | 4.7 | 9.4 | 14.1 | 18.8 |
|  | % Change Fluorescence | 47.08 | 27.59 | 22.91 | 16.62 | 25.00 |
| 50 mM | Concentration TEA (mM) | 0.0 | 9.4 | 18.8 | 28.2 | 37.5 |
|  | % Change Fluorescence | 42.59 | 18.38 | 20.68 | 19.82 | 11.36 |
| 100 mM | Concentration TEA (mM) | 0.0 | 18.8 | 37.5 | 56.3 | 75.0 |
|  | % Change Fluorescence | 43.70 | 26.97 | 21.22 | 22.04 | 15.96 |
| 200 mM | Concentration TEA (mM) | 0.0 | 37.6 | 73.0 | 112.6 | 150.0 |
|  | % Change Fluorescence | 41.90 | 25.83 | 22.36 | 30.10 | 28.22 |

Addition of triethanolamine to the affinity binding buffer showed an increase in the observed fluorescence stability for Qdot™655-30N nanocrystals and had less percent change in fluorescence with time. An increase in the ratio of triethanolamine to affinity binding buffer generally increased this observed fluorescent stability. An initial examination of variable triethanolamine concentrations at pH=10.5 showed that the greatest benefit was achieved with 50 or 100 mM solutions of triethanolamine, wherein 50 mM was very similar or slightly more beneficial than 100 mM.

Figure 3:
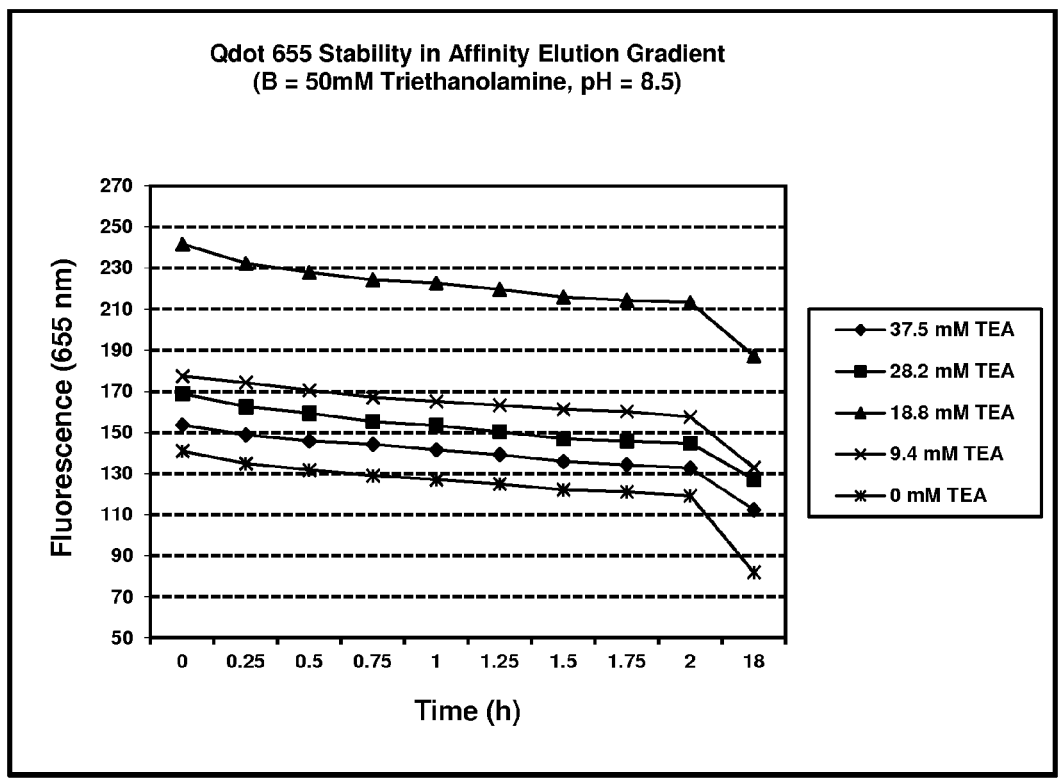
FIG. 3 is a graph of fluorescence light units at 655 nm versus time for Qdot™ 655-30N nanocrystals in an affinity elution gradient with 50 mM triethanolamine at pH 8.5.

Further experimentation was performed with 50 mM triethanolamine at variable elution buffer pH (FIG. 3, Table 2). The values in Table 2 are the percent loss in fluorescence at 655 nm over time after 18 hour time point.

Figure 4:
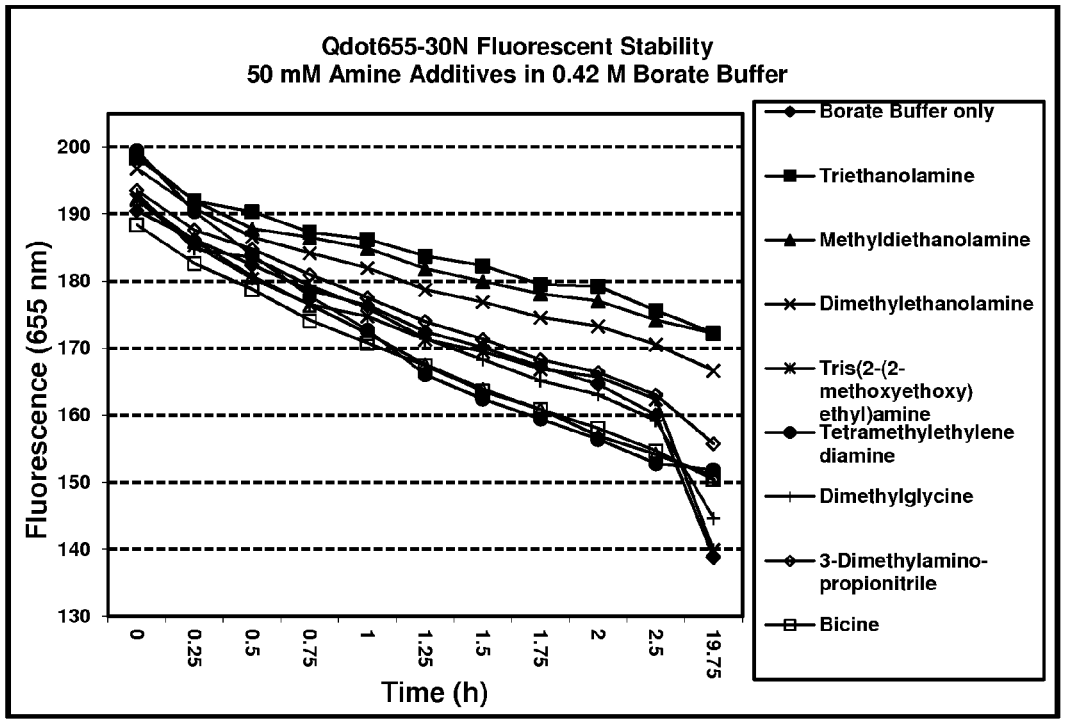
FIG. 4 is a graph of fluorescence light units at 655 nm versus time for Qdot™655-30N nanocrystals in 0.42 M borate buffer with 50 mM amine additives.

50 mM. The relative fluorescence change for a solution of Qdot™655-30N nanoparticles was measured using a Thermofisher Varioskan spectral scanning multimode plate reader. The results are shown in FIG. 4 and Table 3. Data values in Table 3 are represented as percent decrease in Qdot™ fluorescence in solution with time.

TABLE 2

| | | % Change Fluorescence (655 nm) | | | | |
|---|---|---|---|---|---|---|
| % B Elution Gradient [Concentration TEA (mM)] | | 0% (0.0 mM) | 25% (9.4 mM) | 50% (18.8 mM) | 75% (28.2 mM) | 100% (37.5 mM) |
| pH of 50 mM TEA Elution Buffer (B) | pH = 7.5 | 40.12 | 26.77 | 20.47 | 22.32 | 25.06 |
| | pH = 8.5 | 41.88 | 25.11 | 22.52 | 24.70 | 26.84 |
| | pH = 9.5 | 45.95 | 31.22 | 27.25 | 26.03 | 27.69 |
| | pH = 10.5 | 42.59 | 18.38 | 20.68 | 19.82 | 11.36 |

The addition of 50 mM aqueous triethanolamine at pH=10.5 to solutions of Qdot™ nanoparticles in affinity binding buffer resulted in less decrease in observed fluorescence of the Qdot™ samples compared to nanoparticles in affinity binding buffer without such addition. This initial examination of pH for triethanolamine solutions showed that the greatest benefits were achieved with pH=10.5. However, a pH of 10.5 is not suitable for long term antibody stability. A modest increase in fluorescent stability was seen at pH=8.5. This increased fluorescent stability was also observed with 50 mM triethanolamine added to a 50 nM solution of Qdot™655-30N nanocrystals in a 0.42 M borate buffer (pH=8.3).

TABLE 3

| 50 mM Amine Additive in 0.42M Borate Buffer | pH of Solution | % Change Fluorescence (655 nm) | |
|---|---|---|---|
| | | t = 2.5 h | t = 19.75 h |
| 0.42M Borate Buffer Only | 8.5 | 16.0 | 27.1 |
| Triethanolamine | 8.9 | 11.5 | 13.2 |
| N-Methyldiethanolamine | 9.1 | 12.4 | 13.4 |
| N,N-Dimethylethanolamine | 9.4 | 13.4 | 15.3 |
| Tris(2-(2-methoxyethoxy)ethyl)amine | 8.8 | 15.5 | 27.2 |
| N,N,N',N'-Tetramethylethylene diamine | 9.5 | 23.4 | 23.9 |
| N,N-Dimethylglycine | 8.6 | 17.5 | 25.0 |
| 3-Dimethylaminopropionitrile | 8.8 | 15.8 | 19.5 |
| Bicine | 8.1 | 17.9 | 20.2 |
| Bis-TRIS | 8.3 | 19.8 | 21.5 |

Example 2

Effect of Amines on Qdot™ Stability

Quantum dots may include surface defects, which affect luminescence. Some ligands may passivate these surface defects, thus increasing the luminescence quantum yield of the quantum dots. Bullen and Mulvaney investigated the effects of amines on luminescence intensity, and concluded that, "there is no clear effect of the alkylamine ligand chain length on the luminescence intensity for alkyl chains ranging from $C_2$ to $C_{18}$. More significantly, the luminescence clearly follows this trend: primary>>secondary>tertiary amines." (Langmuir, 2006, 22:3007-3013, at p. 3009.) The effect was attributed, at least in part, to the effect that ligand dimensions have on the maximum possible surface ligand coverage: "This suggests that, while increasing the hydrophobicity of the ligand increases surface affinity, it does not compensate for the larger adsorption footprint. At saturation, more of the primary ligand adsorbs." (Bullen, p. 3012.)

Various 1°, 2° and 3° amines with variable functional groups were investigated as alternative amine additives to a 50 nM solution of Qdot™655-30N nanocrystals in 0.42 M borate buffer at pH=8.3. Triethanolamine, N-methyldiethanolamine, N,N-dimethylethanolamine, tris(2-(2-methoxyethoxy)ethyl)amine, N,N,N,N-tetramethylene diamine, N,N-dimethylglycine, 3-dimethylaminoproprionitrile, bicine (N,N-bis(2-hydroxyethyl)glycine), and bis-TRIS (bis(2-hydroxyethyl)amino-tris(hydroxymethyl)-methane) were evaluated. Each amine was added to a final concentration of 50 mM.

In stark contrast to the results obtained by Bullen and Mulvaney, the greatest stability in fluorescence intensity was obtained with triethanolamine, a tertiary amine. A fluorescent stability effect similar to triethanolamine was observed with other 2° and 3° amine additives. However, triethanolamine provided the greatest fluorescence stabilization for disclosed embodiments. Other N-alkylated amines that contained an N-ethanol substituent, mainly N-methyldiethanolamine and N,N-dimethylethanolamine, provided comparable stability.

It was found that an N-ethanol functionalized amino acid, namely bicine or N,N-Bis(2-hydroxyethyl)glycine, increased the fluorescence stability of the Qdot™ solution. Replacing the N-ethanol substituents of bicine with methyl substituents in N,N-dimethylglycine reduced the overall fluorescence stabilization, but did not decrease the fluorescence of the Qdot™ solution.

Capping the hydroxyl group in the N-ethanol substituents with a 2-methoxyethoxy ether as found in tris(2-(2-methoxyethoxy)ethyl)amine produced the same result as with the borate buffer alone. Substitution of an N-ethanol group with a tris(hydroxymethyl)methane group as found in bis-TRIS, bis(2-hydroxyethyl)amino-tris(hydroxymethyl)methane, increased the overall fluorescent stability relative to the borate buffer alone. Thus, it appears that the functional group, —OH, facilitates fluorescence stability.

Example 3

Effect of Buffer Salts on Qdot™ Stability

Figure 5:
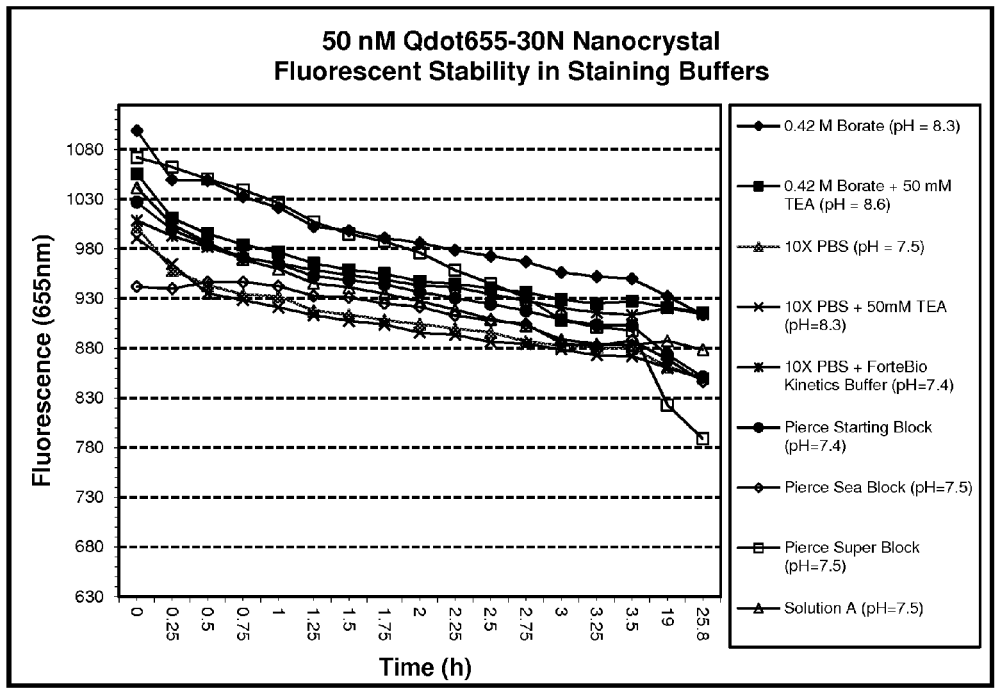
FIG. 5 is a graph of fluorescence light units at 655 nm versus time for Qdot™655-30N nanocrystals in various buffers.

The fluorescence stability of 50 nM Qdot™655-30N nanocrystals in various buffer compositions was evaluated. The buffer compositions included 0.42 M borate (pH 8.3), 0.42 M borate with 50 mM triethanolamine (TEA) (pH 8.6), 10×PBS (100 mM phosphate, 150 mM NaCl, pH 7.5), 10×PBS with 50 mM TEA (pH 8.3) FortéBio Kinetics buffer additive (in 10×PBS), Pierce Starting Block (pH 7.5, available from Thermo Fisher Scientific, Rockford, Ill.), Pierce SEA BLOCK (pH 7.5), and Pierce Super Block (pH 7.5). The results are shown in FIG. 5 and Table 4. Fluorescence data was acquired using a Thermofisher Varioskan spectral scanning multimode plate reader. Data values at 19.0 h and 91.0 h are represented as percent decrease in fluorescence of Qdot™ solution with time. The values at 0 h are the initial fluorescence readings.

TABLE 4

| Buffer Composition (pH) | Qdot Fluorescence (655 nm) | | |
| --- | --- | --- | --- |
| | 0 h | 19.0 h | 91.0 h |
| 0.42M Borate (8.3) | 1099.0 | 15.2 | 24.6 |
| 0.42M Borate, 50 mM TEA (8.6) | 1055.7 | 12.7 | 14.4 |
| 10X PBS (7.5) | 1002.1 | 14.1 | 24.2 |
| 10X PBS, 50 mM TEA (8.3) | 990.7 | 13.2 | 18.7 |
| 10X PBS + ForteBio Kin. Buf. Addit. (7.4) | 1008.5 | 8.7 | 9.8 |
| Pierce Starting Block (7.5) | 1027.0 | 14.9 | 26.4 |
| Pierce Sea Block (7.5) | 942.0 | 7.8 | 18.6 |
| Pierce Super Block (7.5) | 1071.9 | 23.2 | 39.8 |
| Solution A (7.5) | 1041.7 | 14.8 | 15.5 |

The FortéBio Kinetics Buffer additive contains 0.1 mg/mL BSA as a blocking protein, ~0.002 wt % Tween® 20 as a surfactant, and ~0.005 wt % sodium azide as an antibacterial agent. Solution A is an aqueous solution comprising 1.5 wt % casein base hydrolysates and 0.08 wt % sodium azide, which were previously determined to be required for efficient FISH staining using Qdot™-antibody conjugates. An initial evaluation of these additives was performed by formulating variants of three buffer systems (10 mM PBS, 10×PBS and 0.42 M borate) with 1.05 wt % casein base hydrolysates, 50 mM triethanolamine, 0.005 wt % Tween® 20 and 0.008 wt % ProClin® 300 without adjustment of pH. The concentration casein base hydrolysates wt % was initially lowered, as compared to the casein concentration in Solution A, to avoid potential protein aggregation. Concentration of surfactant was increased to bring it above critical micelle concentration (CMC) levels (i.e., the concentration above which micelles spontaneously form). Additionally, Solution A, SEA BLOCK, and MAXblock™ (a non-mammalian blocking agent in PBS, pH 7.4, with 0.09% sodium azide, available from Active Motif® (Carlsbad, Calif.) were evaluated.

Figure 6:
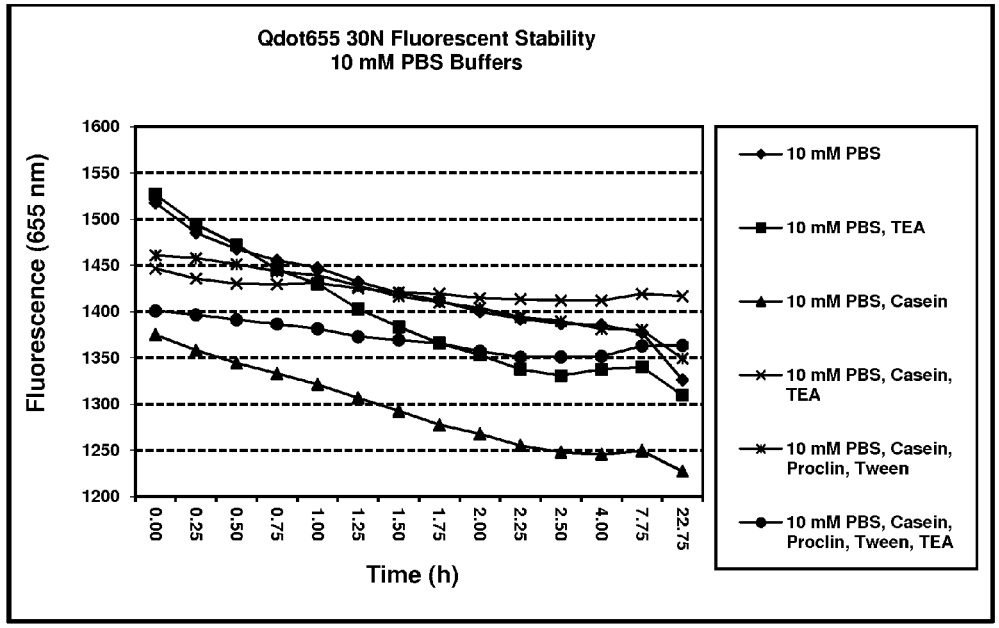
FIG. 6 is a graph of fluorescence light units at 655 nm versus time for Qdot™655-30N nanocrystals in 10 mM PBS buffers containing various additives.
Figure 7:
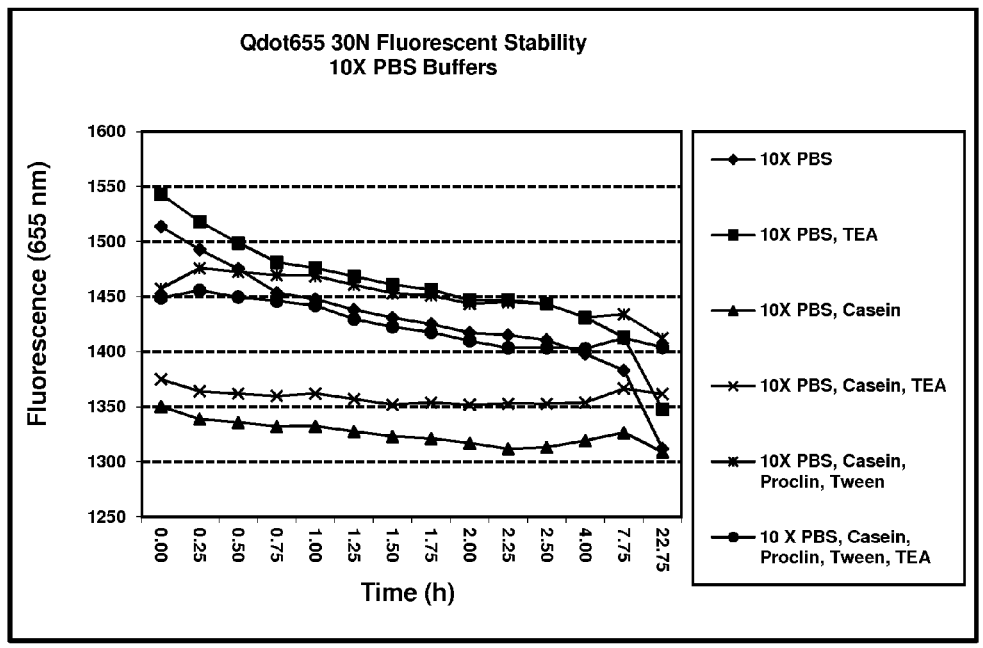
FIG. 7 is a graph of fluorescence light units at 655 nm versus time for Qdot™655-30N nanocrystals in 10× PBS buffers containing various additives.
Figure 8:
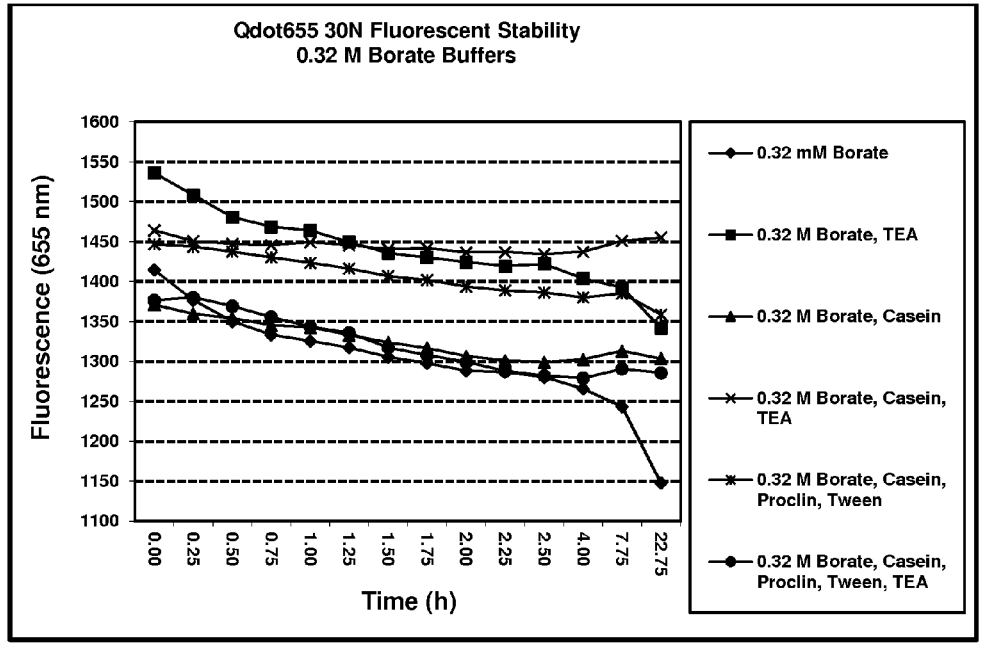
FIG. 8 is a graph of fluorescence light units at 655 nm versus time for Qdot™655-30N nanocrystals in 0.32 M borate buffers containing various additives.

Fluorescence data was acquired using a Thermofisher Varioskan spectral scanning multimode plate reader. The results are shown in FIGS. 6-8, and Tables 5-6. Table 5 provides the buffer formulations used in Table 6. Data values in Table 6 are represented as the percent decrease in fluorescence of Qdot™ solution with time.

TABLE 5

| Buffer | Buffer Formulations |
| --- | --- |
| A | Base Buffer Salt |
| B | A + 50 mM TEA |
| C | A + 1.05% Casein Base Hydrolysates |
| D | C + 50 mM TEA |
| E | C + 0.008% Proclin 300 + 0.005% Tween 20 |
| F | E + 50 mM TEA |

TABLE 6

| Base Buffer | Formulation | pH | Qdot Fluorescence (655 nm) | | |
| --- | --- | --- | --- | --- | --- |
| | | | 4.0 h | 7.75 h | 22.75 h |
| 10 mM PBS | A | 7.4 | 8.7 | 9.2 | 12.6 |
| | B | 9.3 | 12.4 | 12.2 | 14.2 |
| | C | 7.8 | 9.4 | 9.1 | 10.7 |
| | D | 9.1 | 2.4 | 1.9 | 2.1 |
| | E | 7.6 | 5.5 | 5.5 | 7.6 |
| | F | 9.2 | 3.5 | 2.7 | 2.7 |
| 10X PBS | A | 7.5 | 7.6 | 8.6 | 13.3 |
| | B | 8.3 | 7.3 | 8.4 | 12.7 |
| | C | 7.9 | 2.3 | 1.8 | 3.1 |
| | D | 9.1 | 1.5 | 0.6 | 1.0 |
| | E | 7.9 | 1.8 | 1.6 | 3.1 |
| | F | 9.3 | 3.2 | 2.5 | 3.1 |
| 0.32M Borate | A | 8.3 | 10.5 | 12.1 | 18.9 |
| | B | 8.8 | 8.6 | 9.4 | 12.6 |
| | C | 8.5 | 5.0 | 4.2 | 4.9 |
| | D | 9.0 | 1.8 | 0.9 | 0.6 |
| | E | 8.7 | 4.6 | 4.3 | 6.1 |
| | F | 8.9 | 7.1 | 6.2 | 6.6 |
| SeaBlock | n/a | 7.5 | 0.5 | 1.7 | 6.3 |
| MAX BLOCK | n/a | 7.5 | 6.9 | 6.8 | 10.0 |
| Solution A | n/a | 7.5 | 2.9 | 2.5 | 3.4 |

Initial results demonstrated that the greatest fluorescence stability of the Qdot™ solution was seen with the addition of both 50 mM of triethanolamine and 1.05 wt % of casein base hydrolysates. The fluorescence stability was most pronounced in 0.32 M borate buffer. The addition of ProClin® 300 and Tween® 20 appeared to depreciate the observed increase in fluorescent stability.

Figure 9:
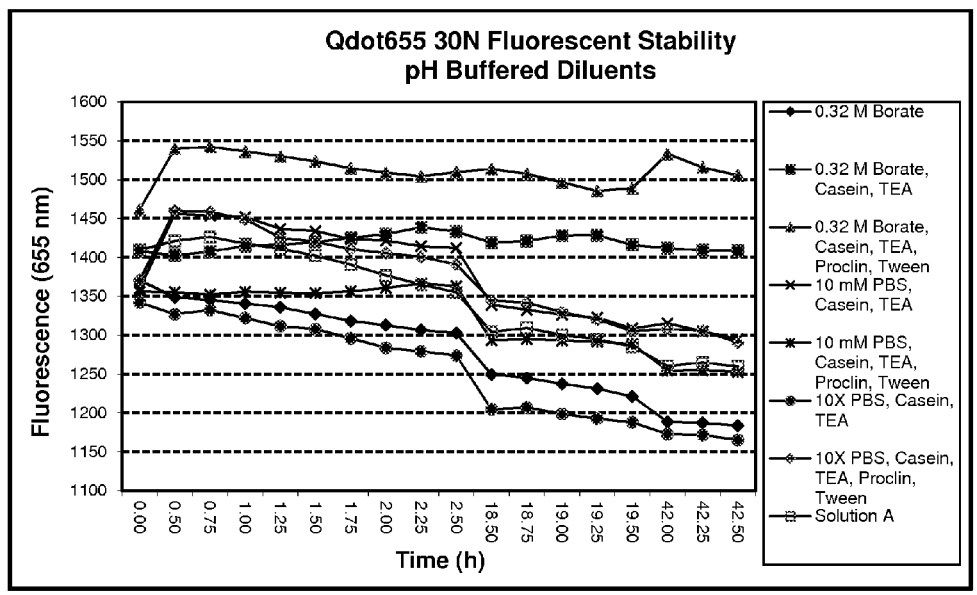
FIG. 9 is a graph of fluorescence light units at 655 nm versus time for Qdot™655-30N nanocrystals in three buffer systems containing blocking protein and triethanolamine, with and without a preservative and surfactant.

To confirm that these observations were not related to pH variations, the fluorescence of 50 nM solutions of Qdot™655-30N nanoparticles was monitored in the three buffer systems (0.1×PBS—pH 7.4, 1×PBS—pH 7.5, and 0.32 M borate—pH 8.3) with 1.05% casein base hydrolysates and 50 mM triethanolamine both with and without 0.005% Tween® 20 and 0.008% ProClin® 300. In each case, the pH was adjusted to the pH of the "parent" buffer. The data was acquired using a Thermofisher Varioskan spectral scanning multimode plate reader. The results are shown in Table 7 and FIG. 9. The values in Table 7 are the percent fluorescence decrease with time. Negative values represent an increase in relative fluorescence.

TABLE 7

| Buffer | Qdot Fluorescence (655 nm) | | |
| --- | --- | --- | --- |
| | 2.5 h | 18.75 h | 42.5 h |
| 0.32M Borate | 5.0 | 9.7 | 13.7 |
| 0.32M Borate + A | −1.8 | −1.4 | 0.0 |
| 0.32M Borate + B | −3.3 | −2.4 | −3.0 |
| 10 mM PBS + A | −3.9 | 2.4 | 4.8 |
| 10 mM PBS + B | −0.5 | 4.6 | 7.6 |
| 10X PBS + A | 5.1 | 10.7 | 13.2 |
| 10X PBS + B | −1.5 | 3.0 | 5.8 |
| Solution A | 3.9 | 7.7 | 10.6 |

A = 1.05% casein base hydrolysates and 50 mM TEA
B = A + 0.008% ProClin ® 300 and 0.005% Tween ® 20

The greatest Qdot™ photoluminescence stability occurred with the addition of both 50 mM triethanolamine and 1.05 wt % casein base hydrolysates to 0.32 M borate buffer.

Figure 10:
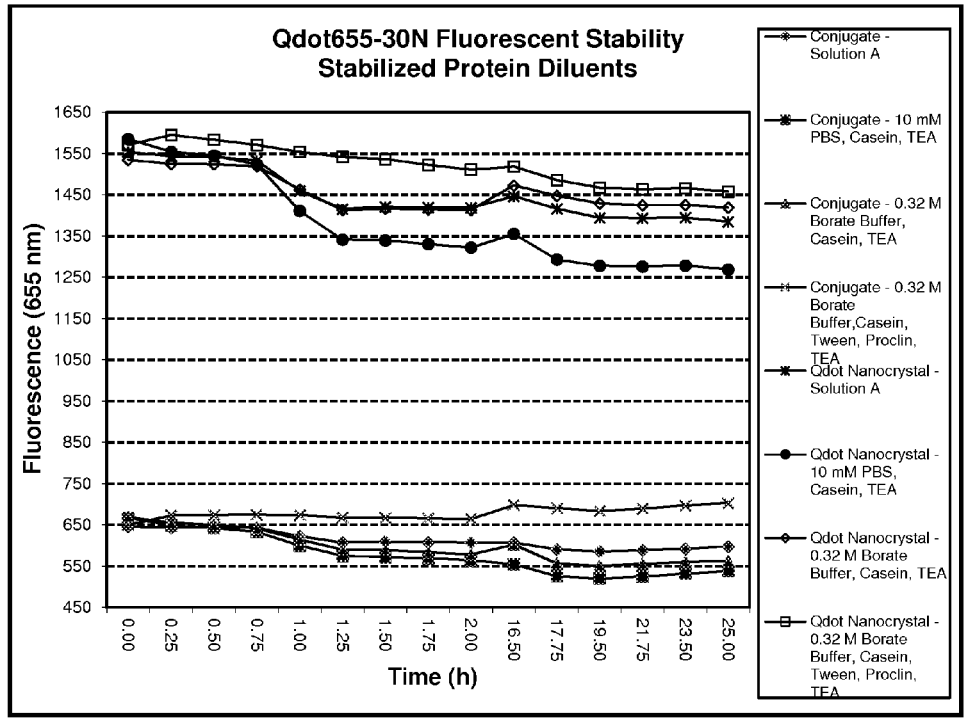
FIG. 10 is a graph of fluorescence light units at 655 nm versus time for Qdot™655-30N nanocrystals and a Qdot™655-30N-Ms MAb conjugate in three buffers with various additives.

Examination of the effect of these diluents on Qdot™-antibody conjugates was further examined. The relative fluorescence change for Qdot™655-30N nanoparticles and a Qdot™655-30N-Ms MAb conjugate in various buffers (Solution A, 10 mM PBS, and 0.32 M borate) with various combinations of additives (1.05% casein, 50 mM TEA, 0.008% ProClin® 300, and 0.005% Tween® 20) was evaluated. Fluorescence data was acquired using a Thermofisher Varioskan spectral scanning multimode plate reader. The results are shown in FIG. 10 and Tables 8-9. Table 8 provides the buffer formulations evaluated in FIG. 10 and Table 9. Data values in Table 9 are represented as the percent fluorescence decrease with time.

TABLE 8

| Diluent | Buffer Formulation |
|---|---|
| A | Solution A |
| B | 10 mM PBS, Casein, TEA, pH = 7.5 |
| C | 0.32M Borate, Casein, TEA, pH = 8.3 |
| D | 0.32M Borate, Casein, Proclin 300, Tween 20, TEA, pH = 8.3 |

TABLE 9

| | | Qdot ™ Fluorescence (655 nm) | | | | | |
|---|---|---|---|---|---|---|---|
| | | 2 h | | 16.5 h | | 25 h | |
| Sample | Diluent | 400 nm | 535 nm | 400 nm | 535 nm | 400 nm | 535 nm |
| Q655-30N-MS | A | 6.07 | 5.83 | 6.07 | 5.04 | 7.48 | 7.06 |
| MAb Conjugate | B | 15.47 | 16.31 | 16.95 | 17.09 | 19.44 | 20.31 |
| | C | 13.49 | 14.30 | 9.90 | 9.82 | 15.87 | 16.40 |
| | D | −2.17 | −0.42 | −7.36 | −6.63 | −8.11 | −6.85 |
| Q655-30N | A | 8.07 | 8.42 | 6.29 | 6.95 | 10.25 | 10.72 |
| Nanocrystal | B | 16.60 | 17.10 | 14.52 | 15.45 | 19.95 | 20.19 |
| | C | 7.92 | 7.67 | 4.04 | 3.44 | 7.53 | 7.24 |
| | D | 3.81 | 3.87 | 3.35 | 3.75 | 7.20 | 7.85 |

These results showed the fluorescent stability was comparable with Qdot™-antibody conjugates. In the case of the Qdot™655-30N-Ms MAb conjugate, the 0.32 M borate buffer with 1.05% casein base hydrolysates and 50 mM triethanolamine, 0.005% Tween® 20 and 0.008% ProClin® 300 (FIG. 10, Table 9) provided a greater stability than the other buffers and was chosen as the base buffer to develop for the Qdot™ Stabilization Buffer (QSB).

Example 4

Effect of Borate Buffer pH and Molarity on Qdot™ Stability

Figure 11:
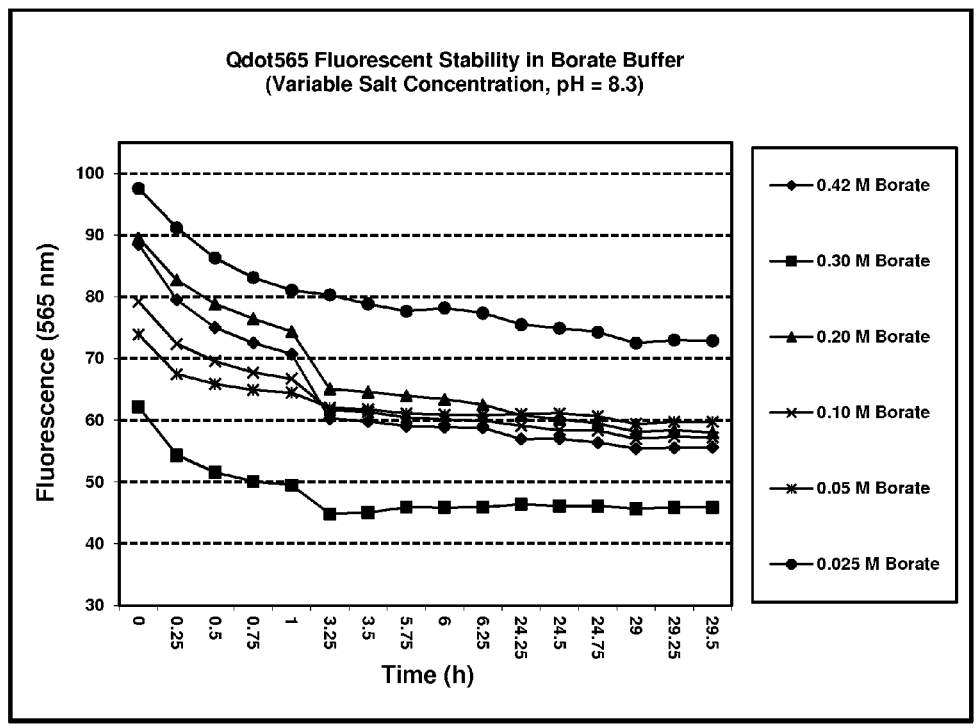
FIG. 11 is a graph of fluorescence light units at 565 nm versus time for Qdot™565-30N nanocrystals in borate buffer at pH 8.3 with variable salt concentrations.

The fluorescence stability of a 50 nM solution of Qdot™565-30N nanocrystals was explored using borate buffer with variable borate salt molarities. The borate molarity was varied from 0.025 M to 0.42 M while maintaining the pH=8.3. Fluorescence data was acquired using a Thermofisher Varioskan spectral scanning multimode plate reader. Excitation was performed at 400 nm, and repeated at 475 nm to confirm results. The results are shown below in Table 10 and FIG. 11. The values at 0 h in Table 10 are the initial fluorescence readings. The data values for other time points are represented as the percent fluorescence decrease with time.

TABLE 10

| | | Qdot ™ Fluorescence (565 nm) | | | | | |
|---|---|---|---|---|---|---|---|
| Borate Molarity (pH = 8.3) | | 0.42M | 0.3M | 0.2M | 0.1M | 0.05M | 0.025M |
| 0 h | 400 nm | 88.522 | 62.172 | 89.555 | 79.213 | 73.916 | 97.579 |
| 1.0 h | 475 nm | 22.3 | 21.3 | 18.1 | 16.7 | 13.6 | 17.4 |
| | 400 nm | 20.1 | 20.4 | 16.9 | 15.8 | 12.7 | 16.9 |
| 3.5 h | 475 nm | 34.6 | 28.4 | 29.2 | 23.8 | 17.0 | 19.0 |
| | 400 nm | 32.4 | 27.5 | 27.9 | 22.6 | 16.4 | 19.2 |
| 6.0 h | 475 nm | 35.4 | 26.7 | 30.5 | 25.1 | 18.9 | 20.9 |
| | 400 nm | 33.5 | 26.2 | 29.2 | 24.1 | 17.6 | 19.9 |
| 24.5 h | 475 nm | 37.9 | 26.8 | 33.9 | 27.3 | 18.3 | 23.4 |
| | 400 nm | 35.6 | 25.8 | 32.8 | 26.3 | 17.3 | 23.2 |
| 29.5 h | 475 nm | 39.0 | 27.4 | 35.9 | 29.0 | 20.5 | 25.0 |
| | 400 nm | 37.2 | 26.2 | 35.2 | 27.8 | 19.2 | 25.3 |

It appears that the borate molarity had very little effect on the Qdot™565-30N nanocrystal fluorescence stability with time. Any change in Qdot™ fluorescence was rapid and occurred primarily within the first 3 hrs. A lower salt concentration may help stabilize proteins and minimize aggregation. A 50 mM borate concentration was chosen to examine other variables.

Figure 12:
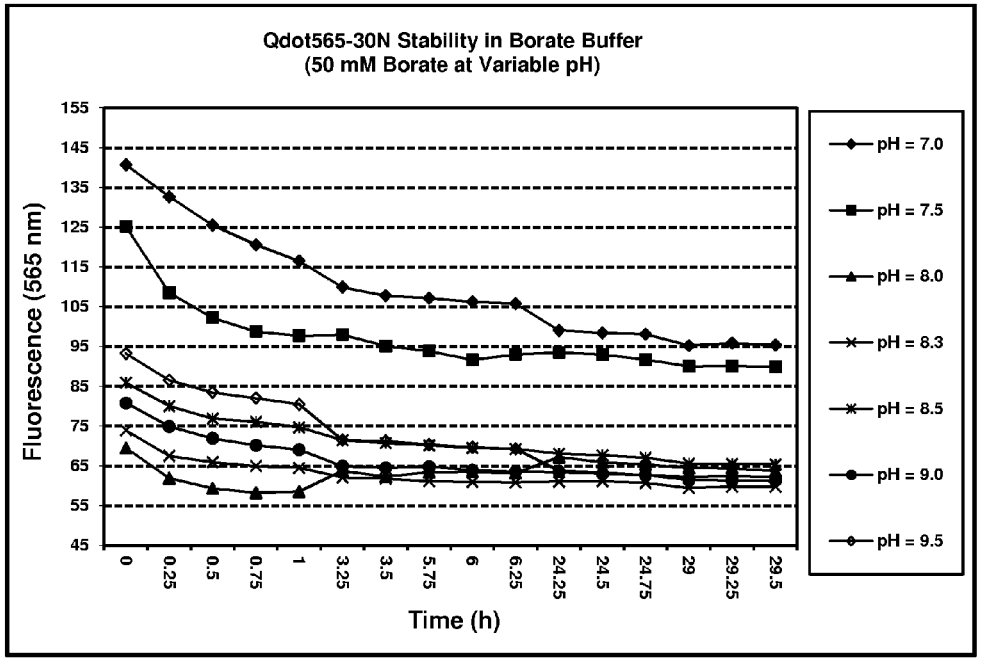
FIG. 12 is a graph of fluorescence light units at 565 nm versus time for Qdot™565-30N nanocrystals in 50 mM borate buffer at various pH values.

Next, the fluorescence stability of a 50 nM solution of Qdot™565-30N nanocrystals was further explored in 50 mM borate buffer with variable pH. The pH of the borate buffer was varied between pH=7.0 to 9.5 to optimize the stability of the Qdot™ photoluminescence. The borate salt concentration was maintained at 50 mM relative to the previous results in Table 10. Fluorescence data was acquired using a Thermofisher Varioskan spectral scanning multimode plate reader. The results of the experiment are shown below in Table 11 and FIG. 12. The values at 0 h in Table 11 are the initial fluorescence readings. The data values for other time points are represented as the percent fluorescence decrease with time.

Example 5

Effect of Protein Concentration and Source on Qdot™ Stability

Figure 13:
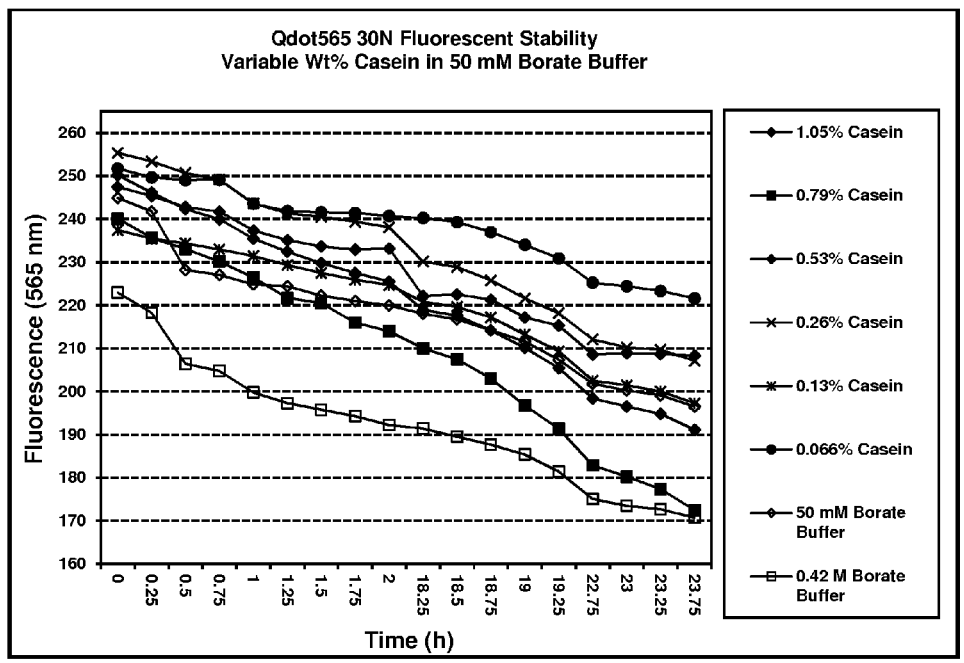
FIG. 13 is a graph of fluorescence light units at 565 nm versus time for Qdot™565-30N nanocrystals in 50 mM borate buffer at pH 8.3 with various protein concentrations.

Earlier stability studies showed that protein aggregation was responsible for depletion of Qdot™-antibody conjugates from solution. Thus, experiments were designed to determine the lowest concentration at which casein would still have a fluorescence stability influence. The fluorescence stability of a 50 nM solution of Qdot™565-30N nanocrystals was explored using 50 mM borate buffer at pH=8.3 with the concentration of casein base hydrolysates varying from 0.066 wt % to 1.05 wt %. Fluorescence data was acquired using a Thermofisher Varioskan spectral scanning multimode plate reader. The results are shown below in Table 12 and FIG. 13. The values at 0 h in Table 12 are the initial fluorescence readings. The data values for other time points are represented as the percent fluorescence decrease with time.

TABLE 11

| | | Qdot ™ Fluorescence (565 nm) | | | | | | |
|---|---|---|---|---|---|---|---|---|
| Buffer pH | | 7.0 | 7.5 | 8.0 | 8.3 | 8.5 | 9.0 | 9.5 |
| 0 h | 400 nm | 140.684 | 125.188 | 69.484 | 100.586 | 85.879 | 80.797 | 93.217 |
| 1.0 h | 475 nm | 15.9 | 23.7 | 19.5 | 13.6 | 13.8 | 15.5 | 14.6 |
| | 400 nm | 17.2 | 22.0 | 15.8 | 12.7 | 13.0 | 14.6 | 13.7 |
| 3.5 h | 475 nm | 21.9 | 24.2 | 12.9 | 17.0 | 18.5 | 21.6 | 25.1 |
| | 400 nm | 23.4 | 24.0 | 10.4 | 16.4 | 17.7 | 20.2 | 23.6 |
| 6.0 h | 475 nm | 23.0 | 27.0 | 11.7 | 18.9 | 19.5 | 21.7 | 26.5 |
| | 400 nm | 24.5 | 26.8 | 8.5 | 17.6 | 19.1 | 20.9 | 25.3 |
| 24.5 h | 475 nm | 28.6 | 26.6 | 7.8 | 18.3 | 22.3 | 23.3 | 33.6 |
| | 400 nm | 30.0 | 25.8 | 5.2 | 17.3 | 21.2 | 22.0 | 32.1 |
| 29.5 h | 475 nm | 30.2 | 28.9 | 10.4 | 20.5 | 24.5 | 25.4 | 34.2 |
| | 400 nm | 32.2 | 28.2 | 8.4 | 19.2 | 23.9 | 24.2 | 33.4 |

As the pH of the buffer was lowered a decrease in the fluorescence stability was observed with time. When pH was lowered, a continued decrease in Qdot™ fluorescence occurred, however, at a more acceptable pH, the photoluminescence was stable. Optimal pH stability was observed at pH=8.0. A suitable range for Qdot™-antibody conjugates would be from 8 to 9.

TABLE 12

| | | Qdot Fluorescence (565 nm) | | | | | | | |
|---|---|---|---|---|---|---|---|---|---|
| % Wt. Casein | | 1.05 | 0.79 | 0.53 | 0.26 | 0.13 | 0.066 | A | B |
| 0 h | 400 nm | 250.1910 | 240.0527 | 247.4338 | 255.3527 | 237.4321 | 251.7085 | 244.9113 | 222.9374 |
| 0.75 h | 475 nm | 4.3 | 4.2 | 2.7 | 2.8 | 2.5 | 1.2 | 8.3 | 9.2 |
| | 400 nm | 4.1 | 4.1 | 2.3 | 2.4 | 1.9 | 1.0 | 7.3 | 8.2 |
| 1.5 h | 475 nm | 8.2 | 8.8 | 5.8 | 5.9 | 4.3 | 4.1 | 9.8 | 13.2 |
| | 400 nm | 8.2 | 8.2 | 5.6 | 5.8 | 4.2 | 4.0 | 9.3 | 12.2 |
| 2.0 h | 475 nm | 10.5 | 11.3 | 6.7 | 6.9 | 5.6 | 4.6 | 11.1 | 14.3 |
| | 400 nm | 9.9 | 10.9 | 5.8 | 6.8 | 5.4 | 4.4 | 10.2 | 13.8 |
| 18.25 h | 475 nm | 13.7 | 14.1 | 11.3 | 11.0 | 7.8 | 5.7 | 13.1 | 15.7 |
| | 400 nm | 12.5 | 12.5 | 10.2 | 9.9 | 7.0 | 4.6 | 11.0 | 14.2 |
| 19.25 h | 475 nm | 18.5 | 21.0 | 13.9 | 15.3 | 12.9 | 8.7 | 16.9 | 19.9 |
| | 400 nm | 17.9 | 20.3 | 13.0 | 14.6 | 11.9 | 8.3 | 15.3 | 18.6 |
| 22.75 h | 475 nm | 21.9 | 24.7 | 17.1 | 17.7 | 15.6 | 11.1 | 19.4 | 22.7 |
| | 400 nm | 20.7 | 23.8 | 15.7 | 17.0 | 14.7 | 10.5 | 17.6 | 21.5 |
| 23.75 h | 475 nm | 24.6 | 29.4 | 16.6 | 19.8 | 18.0 | 12.3 | 21.1 | 24.6 |
| | 400 nm | 23.6 | 28.2 | 15.8 | 18.9 | 16.9 | 12.0 | 19.8 | 23.4 |

A: 50 mM Borate Buffer; B: 0.42M Borate Buffer

Varying the concentration of casein base hydrolysates had an influence on the Qdot™565-30N nanocrystal fluorescence stability. Compositions containing smaller amounts of casein provided more fluorescence stability.

Figure 14:
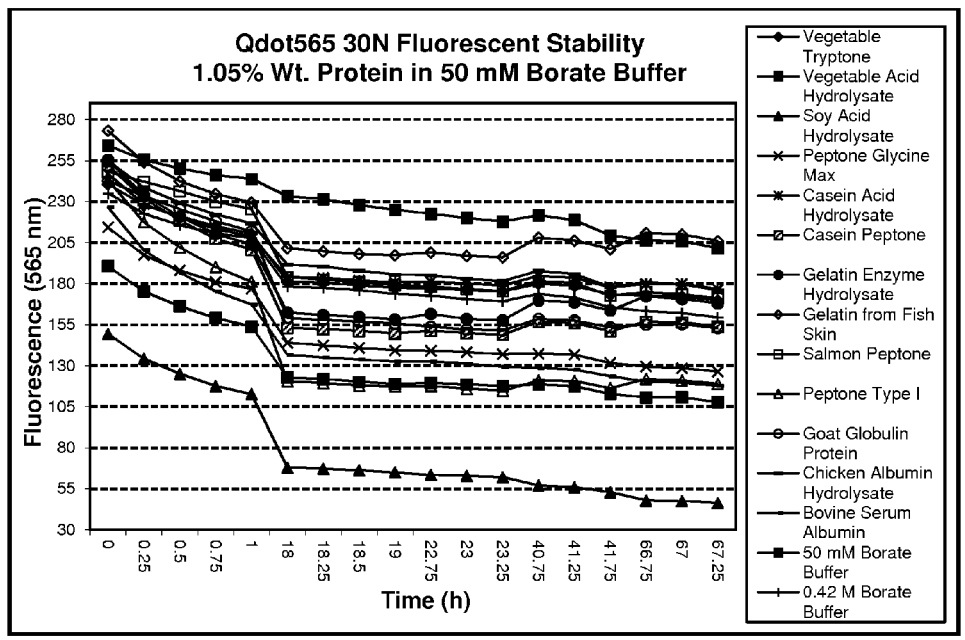
FIG. 14 is a graph of fluorescence light units at 565 nm versus time for Qdot™565-30N nanocrystals in 50 mM borate buffer at pH 8.3 with 1.05% wt various protein sources.

Several other 1.05 wt % protein sources in 50 mM borate buffer at pH=8.3 were examined as potential casein base hydrolysates substitutes. The protein sources are listed in Table 13. Fluorescence data was acquired using a Thermofisher Varioskan spectral scanning multimode plate reader. The results are shown in Table 14 and FIG. 14. The data values in Table 14 are represented as the percent fluorescence decrease with time.

TABLE 13

| Diluent | Protein Source |
|---|---|
| 1 | Vegetable Tryptone |
| 2 | Vegetable Protein Acid Hydrolysate |
| 3 | Soy Protein Acid Hydrolysate |
| 4 | Peptone Glycine Max |
| 5 | Casein Acid Hydrolysate |
| 6 | Casein Peptone |
| 7 | Gelatin Enzymatic Hydrolysate |
| 8 | Gelatin from Fish Skin |
| 9 | Salmon Peptone |
| 10 | Peptone Type I |
| 11 | Goat Globulin Protein |
| 12 | Chicken Albumin Hydrolysate |
| 13 | Bovine Serum Albumin |
| 14 | 50 mM Borate Buffer |
| 15 | 0.42M Borate Buffer |

TABLE 14

| Protein | Buffer | Qdot Fluorescence (565 nm) | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| 1.0 h | 475 nm | 13.9 | 21.2 | 26.3 | 18.8 | 17.4 | 22.0 | 22.0 | 17.2 | 9.5 | 27.0 | 12.9 | 17.0 | 27.1 | 9.0 | 13.1 |
| | 400 nm | 12.6 | 19.3 | 24.7 | 17.5 | 15.4 | 20.4 | 20.3 | 16.0 | 9.2 | 25.5 | 12.7 | 15.0 | 26.2 | 7.7 | 11.6 |
| 18.0 h | 475 nm | 26.8 | 38.2 | 54.1 | 35.3 | 27.5 | 41.5 | 38.3 | 27.5 | 27.4 | 51.9 | 35.5 | 27.2 | 42.2 | 13.0 | 25.7 |
| | 400 nm | 24.7 | 35.6 | 54.6 | 32.8 | 25.5 | 39.3 | 36.4 | 26.2 | 25.9 | 50.4 | 34.5 | 24.9 | 39.7 | 11.7 | 24.3 |
| 40.75 h | 475 nm | 28.2 | 40.9 | 61.5 | 38.7 | 28.0 | 40.3 | 36.2 | 25.7 | 28.5 | 52.4 | 36.3 | 29.2 | 45.9 | 17.6 | 28.4 |
| | 400 nm | 25.3 | 37.9 | 61.9 | 36.0 | 25.2 | 37.8 | 33.6 | 23.9 | 26.9 | 50.3 | 34.7 | 26.4 | 43.2 | 16.1 | 26.1 |

At 1.05 wt % protein concentration, the protein sources with the best potential as a casein base hydrolysates substitute were vegetable tryptone, casein acid hydrolysates and gelatin from fish skin.

Example 6

Effect of Surfactants on Qdot™ Stability

Figure 15:
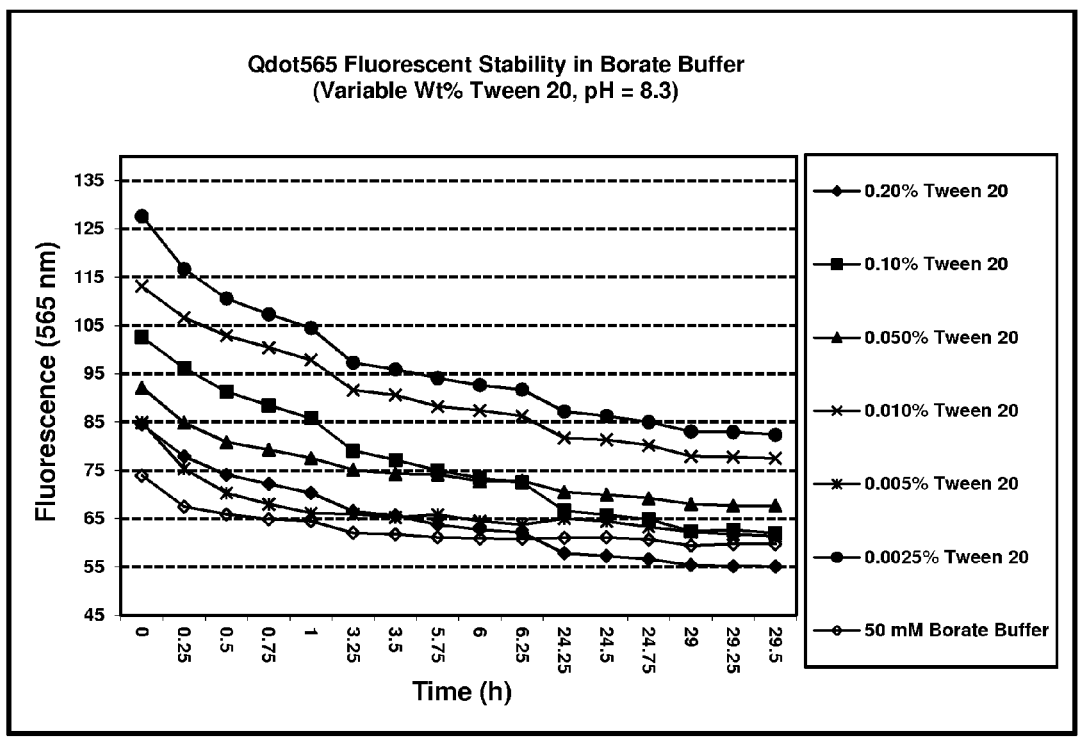
FIG. 15 is a graph of fluorescence light units at 565 nm versus time for Qdot™565-30N nanocrystals in 50 mM borate buffer at pH 8.3 with variable concentrations of Tween® 20.

Due to concerns regarding potential aggregation of protein and Qdot™-antibody conjugates, the use of surfactants to deter aggregation and further stabilize the Qdot™ nanocrystals was investigated. The fluorescence stability of a 50 nM solution of Qdot™565-30N nanocrystals was explored using 50 mM borate buffer at pH=8.3 with variable Tween® 20 concentrations. The Tween® 20 was varied from 0.0025 wt % to 0.20 wt %. Fluorescence data was acquired using a Thermofisher Varioskan spectral scanning multimode plate reader. The results are shown below in Table 15 and FIG. 15. The values at 0 h in Table 15 are the initial fluorescence readings. The data values for other time points are represented as the percent fluorescence decrease with time.

TABLE 15

| Wt % Tween 20 | | 0.20 | 0.10 | 0.050 | 0.010 | 0.0050 | 0.0025 | Borate |
|---|---|---|---|---|---|---|---|---|
| | | Qdot Fluorescence (565 nm) | | | | | | |
| 0 h | 400 nm | 84.497 | 102.604 | 92.132 | 113.090 | 84.949 | 127.598 | 73.916 |
| 1.0 h | 475 nm | 17.7 | 16.1 | 15.5 | 13.9 | 22.6 | 19.7 | 13.6 |
| | 400 nm | 16.8 | 16.4 | 15.8 | 13.5 | 22.1 | 18.1 | 12.7 |
| 3.5 h | 475 nm | 23.4 | 24.3 | 19.1 | 19.8 | 24.3 | 25.6 | 17.0 |
| | 400 nm | 22.3 | 24.8 | 19.4 | 19.9 | 23.2 | 24.8 | 16.4 |
| 6.0 h | 475 nm | 25.7 | 27.7 | 20.5 | 22.5 | 24.4 | 28.2 | 18.9 |
| | 400 nm | 25.7 | 28.4 | 21.0 | 22.7 | 24.1 | 27.4 | 17.6 |
| 24.5 h | 475 nm | 32.6 | 35.1 | 23.4 | 28.1 | 24.8 | 33.6 | 18.3 |
| | 400 nm | 32.3 | 35.9 | 24.1 | 28.1 | 24.1 | 32.4 | 17.3 |
| 29.5 h | 475 nm | 34.8 | 38.7 | 26.0 | 31.4 | 28.1 | 36.0 | 20.5 |
| | 400 nm | 34.8 | 39.6 | 26.5 | 31.5 | 27.7 | 35.5 | 19.2 |

The Tween® 20 concentration had some effect on the Qdot™565-30N nanocrystal fluorescence stability. Addition of any amount of Tween® 20 to a 50 mM borate buffer solution at pH=8.3 decreased the relative fluorescent stability compared to borate buffer alone. Tween® 20 appears to be most tolerable when the concentration is maintained between 0.005 and 0.05 wt %. A 0.05 wt % Tween® 20 concentration would potentially provide more fluorescent stability to Qdot™-antibody conjugates then 0.005 wt %. It is contemplated that the surfactant stabilizes the protein thereby avoiding aggregation of the Qdot™s.

Figure 16:
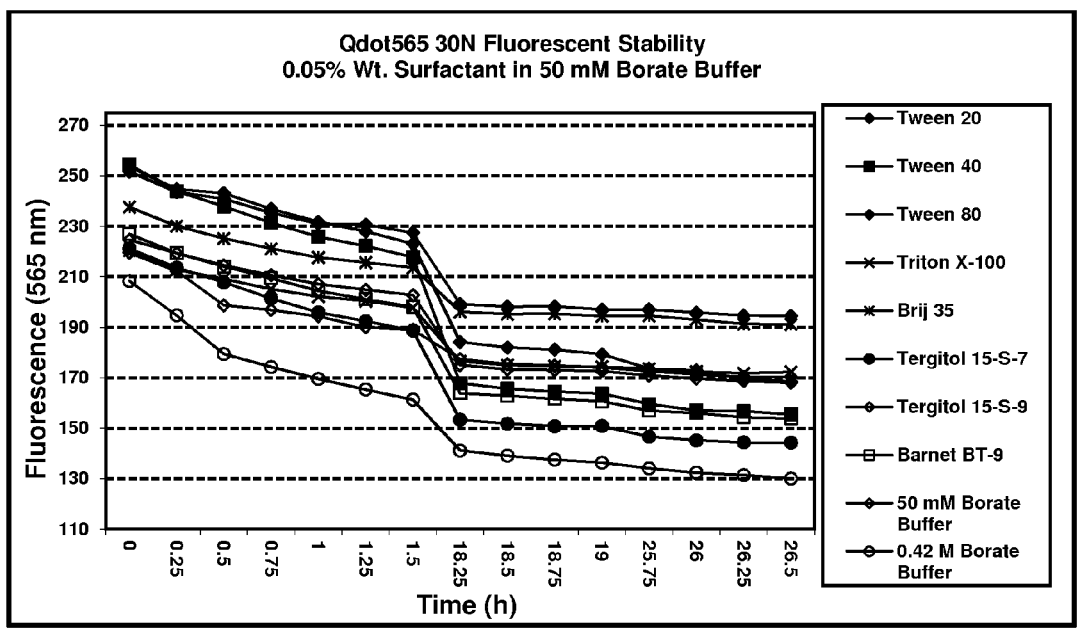
FIG. 16 is a graph of fluorescence light units at 565 nm versus time for Qdot™565-30N nanocrystals in 50 mM borate buffer at pH 8.3 with various surfactants.

Since Tween® 20 appeared to have a negative impact on the fluorescent stability of Qdot™565-30N nanocrystals in 50 mM borate buffer at pH 8.3, other surfactants were examined as potential alternatives. In prior experimentation, it was discovered that Qdot™ nanocrystals are most stable with nonionic surfactants. A variety of nonionic surfactants were formulated at 0.05 wt % concentration in 50 mM borate buffer at pH 8.3. The surfactants are listed in Table 16. Fluorescence data was acquired using a Thermofisher Varioskan spectral scanning multimode plate reader. Results are shown in Table 17 and FIG. 16. The values at 0 h in Table 17 are the initial fluorescence readings. The data values for other time points are represented as the percent fluorescence decrease with time.

TABLE 16

| Buffer | Surfactant |
|---|---|
| 1 | Tween 20 |
| 2 | Tween 40 |
| 3 | Tween 80 |
| 4 | Triton X-100 |
| 5 | Brij 35 |
| 6 | Tergitol 15-S-7 |
| 7 | Tergitol 15-S-9 |
| 8 | Barnet BT-9 |
| 9 | 50 mM Borate |
| 10 | 0.42M Borate |

TABLE 17

| Surfactant | | 1 | 2 | 3 | 4 | 5 | 6 | 7 | 8 | 9 | 10 |
|---|---|---|---|---|---|---|---|---|---|---|---|
| | | Qdot Fluorescence (565 nm) | | | | | | | | | |
| 0 h | 400 nm | 251.6299 | 254.3890 | 253.7050 | 220.4611 | 237.6370 | 221.1766 | 224.6263 | 226.9742 | 219.5009 | 208.3340 |
| 1.25 h | 475 nm | 7.8 | 13.1 | 10.4 | 9.3 | 9.7 | 13.0 | 8.5 | 11.8 | 14.6 | 21.9 |
| | 400 nm | 8.3 | 12.7 | 10.1 | 9.1 | 9.3 | 13.0 | 8.8 | 11.4 | 13.4 | 20.6 |
| 18.25 h | 475 nm | 21.6 | 34.8 | 28.2 | 20.5 | 18.1 | 31.8 | 22.6 | 28.4 | 20.7 | 33.8 |
| | 400 nm | 20.8 | 34.0 | 27.4 | 19.9 | 17.5 | 30.7 | 22.1 | 27.8 | 19.2 | 32.2 |
| 19.0 h | 475 nm | 22.6 | 36.8 | 30.4 | 20.9 | 18.8 | 32.7 | 23.3 | 30.2 | 21.4 | 36.4 |
| | 400 nm | 21.7 | 35.6 | 29.3 | 20.9 | 18.2 | 31.8 | 23.1 | 29.2 | 20.7 | 34.6 |
| 25.75 h | 475 nm | 22.2 | 36.8 | 30.4 | 20.9 | 18.8 | 32.7 | 23.3 | 30.2 | 21.4 | 36.4 |
| | 400 nm | 21.7 | 35.6 | 29.3 | 20.9 | 18.2 | 31.8 | 23.1 | 29.2 | 20.7 | 34.6 |
| 26.5 h | 475 nm | 23.7 | 39.8 | 34.3 | 22.4 | 20.2 | 35.7 | 25.1 | 32.8 | 23.2 | 39.0 |
| | 400 nm | 22.7 | 38.9 | 33.6 | 21.9 | 19.6 | 34.8 | 25.2 | 32.2 | 22.4 | 37.6 |
| 42.0 h | 475 nm | 24.3 | 42.1 | 37.3 | 24.2 | 21.6 | 37.7 | 27.2 | 34.9 | 24.3 | 39.6 |
| | 400 nm | 23.9 | 41.7 | 36.6 | 23.5 | 20.7 | 36.6 | 27.1 | 34.1 | 23.4 | 38.3 |

Brij 35 (polyoxyethyleneglycol dodecyl ether), 0.05 wt %, provided better fluorescent stability than Tween® 20 and stabilized the nanocrystals more than 50 mM borate buffer alone. Triton® X-100 (polyethylene glycol p-(1,1,3,3-tetramethylbutyl)-phenyl ether) provided a fluorescence influence comparable to Tween® 20.

Example 7

Initial Formulation of Qdot™ Stabilization Buffer (QSB)

Utilizing the active ingredients used in the stability of Q655-antibody conjugates shown in FIG. 10 (Table 8), the following initial formulation of QSB was used based on 0.42 M borate buffer at pH=8.3. Described below is the formulation for 100 mL of buffer:

75 mL of 0.42 M borate buffer, pH=8.3 (final ~0.32 M borate)
25 mL of casein base hydrolysates (42 mg/mL casein, final ~1.05 wt % casein)
664 µL of triethanolamine (~50 mM)
8 µL of ProClin® 300 (~0.01 wt %)
5 µL of Tween® 20 (~0.005 wt %)

Subsequent variations were formulated and evaluated, as described in the following examples.

Example 8

Effect of Antibacterial Reagents on Qdot™ Stability

A. Stability of Qdot™-30N Nanoparticles and their Conjugates in QSB with 0.05% or 0.01% ProClin® 300.

Initially, 0.01 wt % ProClin® 300 was selected, but it did not provide adequate antibacterial protection. Studies showed that 0.05 wt % provided adequate protection. Subsequently, QSB formulations comprising 0.007% and 0.05% were prepared, and the effect of the ProClin® 300 concentration on Qdot™ fluorescence was evaluated.

Three buffers were prepared:
A: Solution A (1.5 wt % casein base hydrolysates, 0.08 wt % sodium azide)
B: QSB with 0.007% ProClin® 300 ("Partial Borate")
C: QSB with 0.05% ProClin® 300 ("Full Borate")

Figure 17:
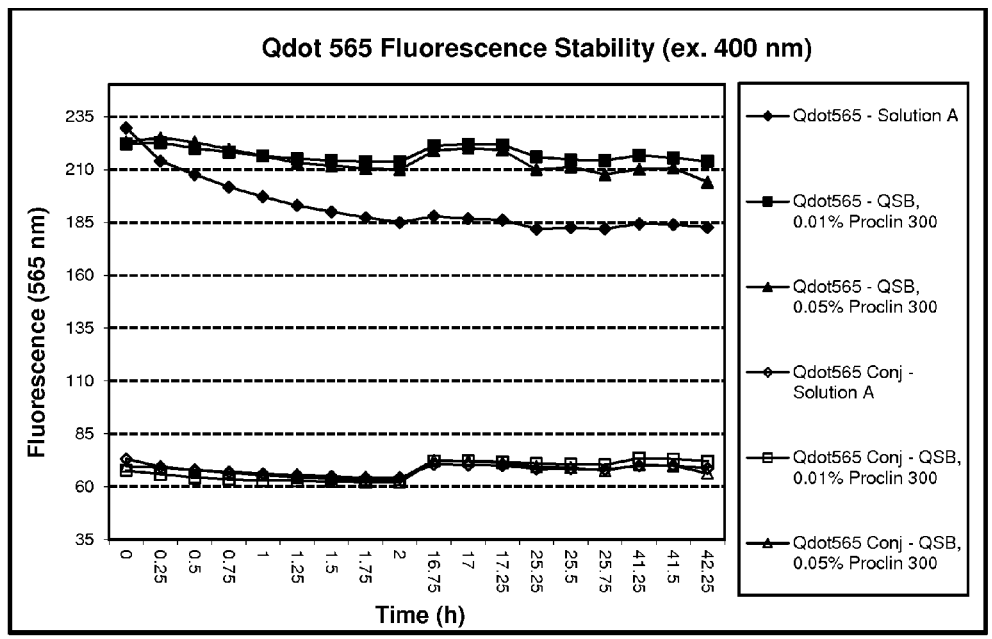
FIG. 17 is a graph of fluorescence light units at 565 nm versus time for Qdot™565-30N nanocrystals and Qdot™565-30N-Ms MAb conjugates in buffers with variable concentrations of ProClin® 300.
Figure 18:
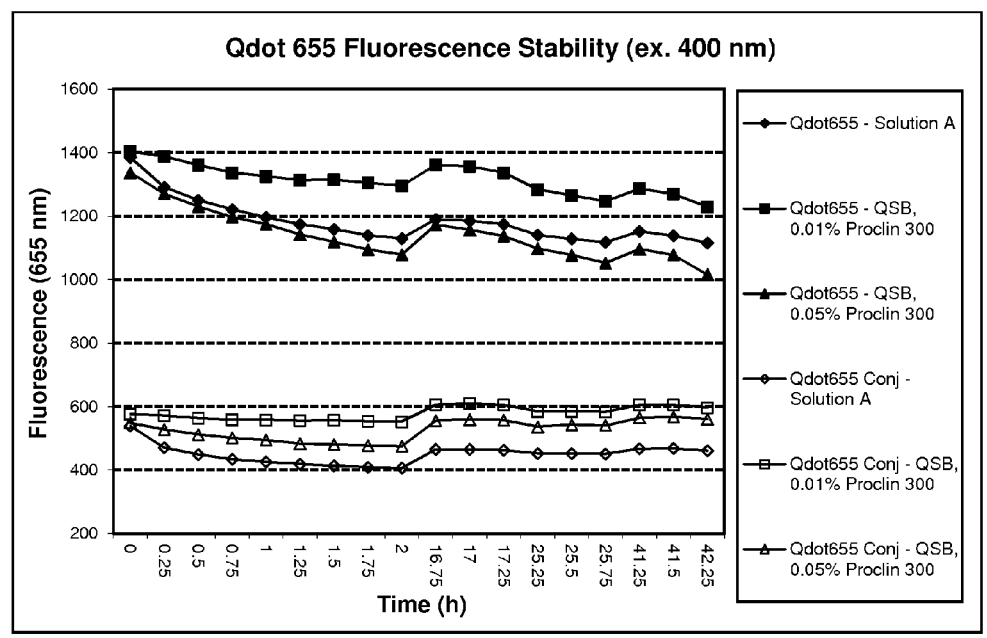
FIG. 18 is a graph of fluorescence light units at 655 nm versus time for Qdot™655-30N nanocrystals and Qdot™655-30N-Ms MAb conjugates in buffers with variable concentrations of ProClin® 300.
Figure 19:
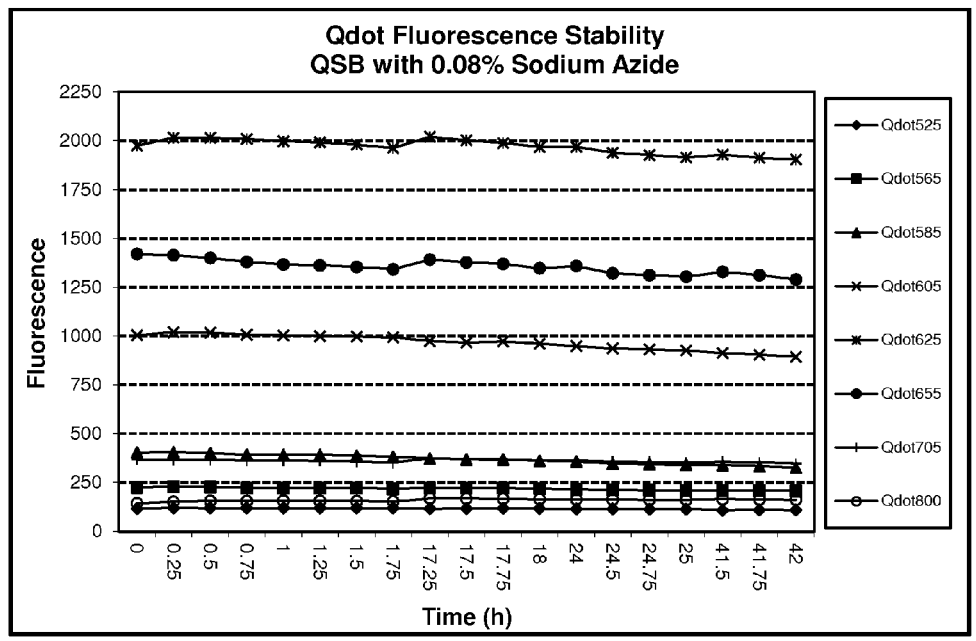
FIG. 19 is a graph of fluorescence light units versus time for various Qdot™-30N nanocrystals in a Qdot™ stabilization buffer composition with 0.08 wt % sodium azide.
Figure 20:
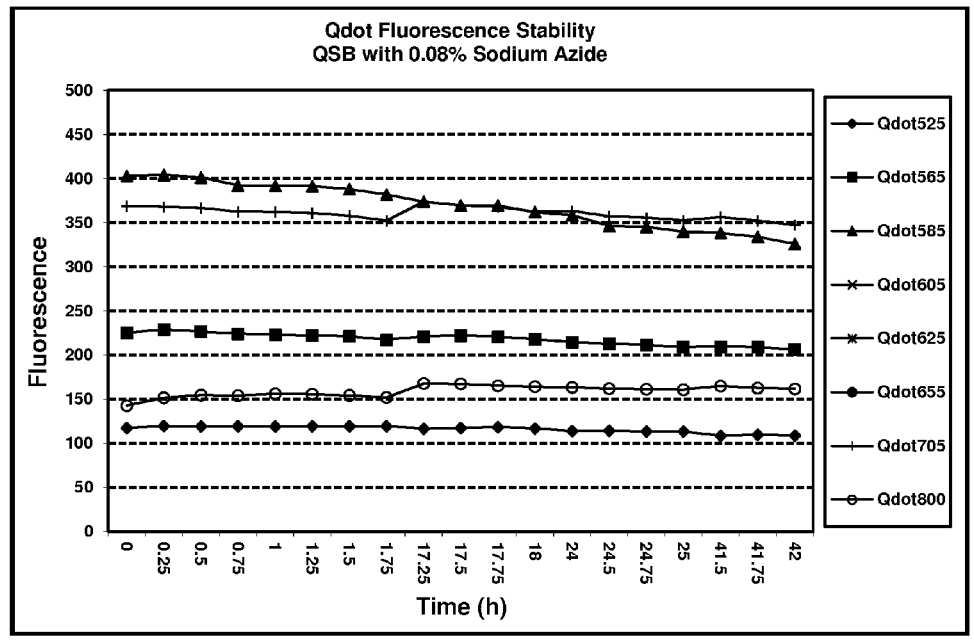
FIG. 20 is an expanded view of the lower portion of FIG. 19.
Figure 21:
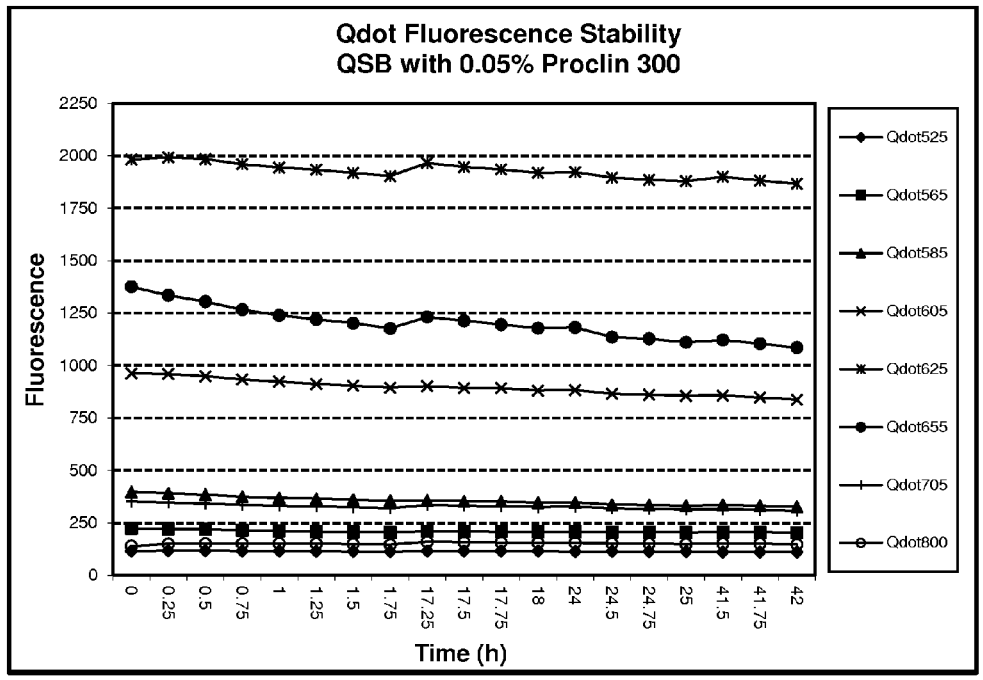
FIG. 21 is a graph of fluorescence light units versus time for various Qdot™-30N nanocrystals in a Qdot™ stabilization buffer composition with 0.05 wt % ProClin® 300.
Figure 22:
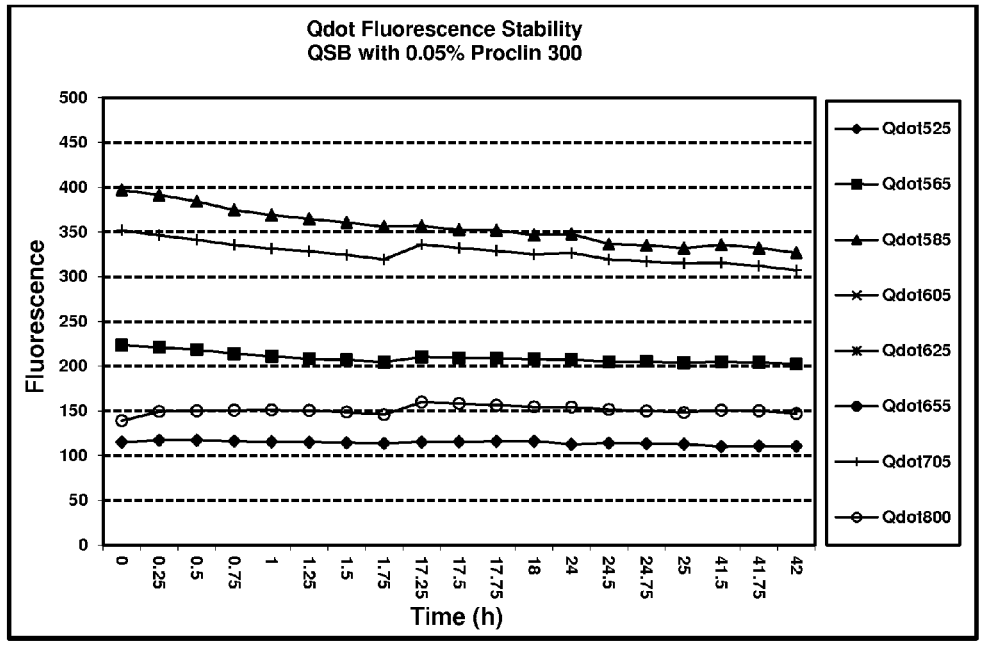
FIG. 22 is an expanded view of the lower portion of FIG. 21.

Data was acquired using a Varioskan spectral scanning multimode plate reader. The results are shown below in Tables 18-19 and FIGS. 17-18. The data values in Tables 18 and 19 are represented as the percent fluorescence decrease with time. Negative values indicate an increase in fluorescence.

Analysis of the fluorescent signal from Qdot™ nanoparticles and their conjugates in solution at room temperature showed that an increase of ProClin® 300 levels from 0.01 wt % to 0.05 wt % in QSB caused a decrease in the observed fluorescence stability of all Qdot™ materials. Both QSB compositions provided less observed fluorescent change than Solution A for the Qdot™565 nanocrystals. However for the Qdot™655 nanocrystal, QSB with 0.05 wt % ProClin® 300 produced more fluorescence loss than Solution A. In the case of the Qdot™655-30N-Ms MAb conjugate, the increase of ProClin® 300 from 0.01 wt % to 0.05 wt % in QSB caused only a minor decrease in the fluorescence stability. However for the Qdot™565-30N-Ms MAb conjugate, QSB with 0.05 wt % ProClin® 300 was comparable to Solution A.

B. Stability of Qdot™-30N Nanoparticles in QSB with 0.05% ProClin® 300 or 0.08% Sodium Azide The effective literature pH stability range for ProClin® 300 is from pH=3.0 to 8.5 (for example, as provided by Sigma-Aldrich). At a pH near or above pH=8.5, the effective antibacterial properties of ProClin® 300 is reduced. The additional drop in the observed fluorescence stability for Qdot™ nanocrystals in QSB with 0.05 wt % ProClin® 300 prompted an investigation of 0.08 wt % of sodium azide as a replacement. Since there was a difference in the observed fluorescence stability for both Qdot™565 and Qdot™655-30N nanocrystals with ProClin® 300, the influence of these reagents was examined on additional Qdot™ nanocrystals at room temperature. The Qdot™-30N nanoparticles were evaluated in QSB with either 0.05 wt % ProClin® 300 or 0.08 wt % sodium azide. Fluorescence data was acquired using a Varioskan spectral scanning multimode plate reader. The data is shown below in Tables 20A-B and FIGS. 19-22. The data values in Tables 20A-B are represented as the percent fluorescence decrease with time. Negative values indicate an increase in fluorescence.

TABLE 18

| | | Qdot Fluorescence (565 nm) | | | | | |
|---|---|---|---|---|---|---|---|
| | | t = 20 h | | t = 17.25 h | | t = 42.25 h | |
| Sample | Buffer | 400 nm | 500 nm | 400 nm | 500 nm | 400 nm | 500 nm |
| Qdot565-30N-Nanocrystal | A | 19.50 | 18.56 | 18.95 | 17.86 | 20.51 | 19.77 |
| | B | 3.82 | 3.32 | 0.25 | −0.04 | 3.75 | 3.45 |
| | C | 5.89 | 4.37 | 1.72 | 0.90 | 8.49 | 7.97 |
| Qdot565-30N-Ms MAb Conjugate | A | 12.16 | 10.14 | 4.18 | 2.63 | 6.09 | 3.65 |
| | B | 8.18 | 6.08 | −5.88 | −6.87 | −6.62 | −7.60 |
| | C | 9.03 | 7.40 | −2.26 | −2.95 | 4.95 | 3.26 |

TABLE 19

| | | Qdot Fluorescence (655 nm) | | | | | |
|---|---|---|---|---|---|---|---|
| | | t = 2.0 h | | t = 17.25 h | | t = 42.25 h | |
| Sample | Buffer | 400 nm | 500 nm | 400 nm | 500 nm | 400 nm | 500 nm |
| Qdot655-30N-Nanocrystal | A | 19.50 | 18.56 | 15.19 | 14.77 | 19.41 | 18.56 |
| | B | 3.82 | 3.32 | 4.75 | 4.69 | 12.42 | 11.77 |
| | C | 5.89 | 4.37 | 14.94 | 14.32 | 24.03 | 23.15 |
| Qdot655-30N-Ms MAb Conjugate | A | 12.16 | 10.14 | 14.11 | 12.91 | 14.41 | 13.28 |
| | B | 8.18 | 6.08 | −5.07 | −6.70 | −3.61 | −5.47 |
| | C | 9.03 | 7.40 | −1.61 | −2.72 | −2.30 | −3.76 |

TABLE 20A

| Qdot™ | t = 1.75 h | | t = 17.25 h | | t = 18.0 h | |
|---|---|---|---|---|---|---|
| | Azide | ProClin® 300 | Azide | ProClin® 300 | Azide | ProClin® 300 |
| 525 | −1.63 | 1.30 | 0.72 | −0.11 | 0.42 | −0.88 |
| 565 | 3.46 | 8.43 | 1.82 | 5.87 | 3.23 | 6.98 |
| 585 | 5.21 | 10.32 | 7.25 | 10.12 | 10.16 | 12.68 |
| 605 | 1.06 | 7.13 | 2.93 | 6.35 | 4.28 | 8.54 |
| 625 | 0.62 | 3.98 | −2.31 | 0.79 | 0.38 | 3.18 |
| 655 | 5.57 | 14.45 | 2.07 | 10.53 | 5.21 | 14.42 |
| 705 | 4.56 | 9.23 | −1.28 | 4.49 | 1.76 | 7.59 |
| 800 | −6.38 | −4.89 | −17.41 | −14.85 | −14.95 | −11.09 |

TABLE 20B

| Qdot™ | t = 25.0 h | | t = 42.0 h | |
|---|---|---|---|---|
| | Azide | ProClin® 300 | Azide | ProClin® 300 |
| 525 | 3.47 | 1.96 | 7.39 | 4.02 |
| 565 | 7.03 | 8.73 | 8.33 | 9.43 |
| 585 | 15.66 | 16.33 | 19.10 | 17.68 |
| 605 | 7.71 | 11.16 | 10.90 | 13.07 |
| 625 | 3.08 | 5.22 | 3.60 | 5.81 |
| 655 | 8.30 | 19.28 | 9.26 | 21.10 |
| 705 | 4.46 | 10.48 | 5.87 | 12.69 |
| 800 | −12.62 | −6.62 | −13.24 | −5.79 |

Less change in the relative photoluminescence of Qdot™ nanocrystals was observed in QSB containing 0.08 wt % sodium azide than QSB containing 0.05 wt % ProClin® 300. In addition, the relative rate of change varied for each Qdot™ nanocrystal. The greatest loss in the observed fluorescence was with Qdot™585-30N nanocrystals. There was a net increase in the relative fluorescence for Qdot™800-30N nanocrystals.

Figure 23:
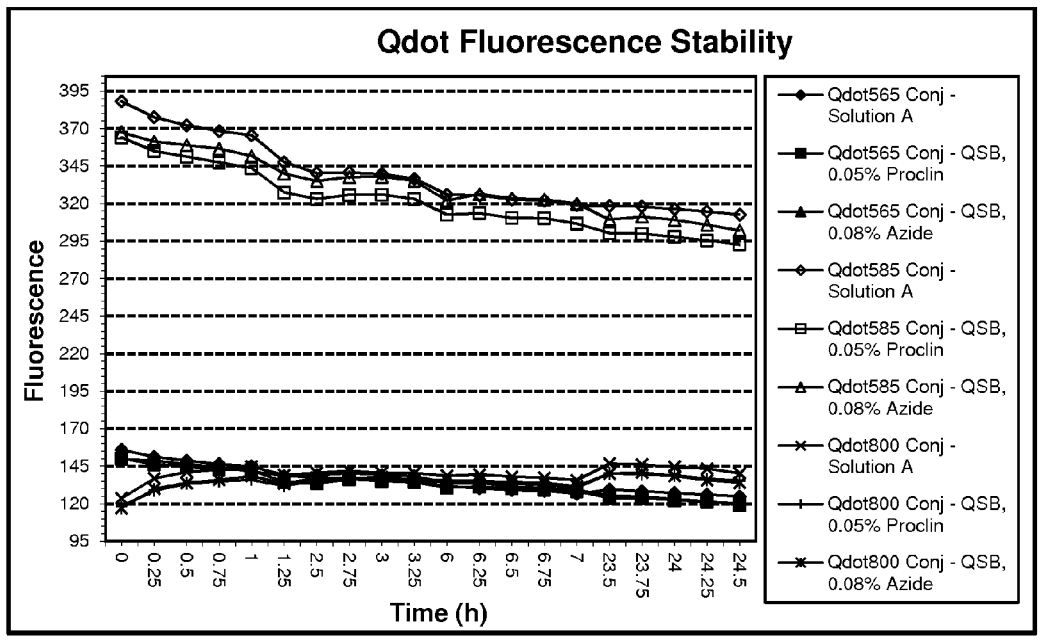
FIG. 23 is a graph of fluorescence light units versus time for various Qdot™-30N-Ms MAb conjugates in Solution A or a Qdot™ stabilization buffer composition with either 0.05 wt % ProClin® 300 or 0.08 wt % sodium azide. Each Qdot™ is measured at a different wavelength.

C. Stability of Qdot™-30N-Ms MAb Conjugates in QSB with 0.05% ProClin® 300 or 0.08% Sodium Azide The relative fluorescence of three Qdot™-30N-antibody conjugates were examined in Solution A or QSB containing either 0.08 wt % of sodium azide or 0.05 wt % ProClin® 300 at room temperature. To provide the broadest influence on the observed fluorescence, both Qdot™800 and Qdot™585-30N-Ms MAb conjugates were chosen for this experiment. These conjugates were compared to Qdot™565-30N-Ms MAb conjugate for the consistency of data sets to previous data sets. Excitation was performed at 400 nm. Fluorescence data was acquired using a Varioskan spectral scanning multimode plate. The data is shown below in Table 21 and FIG. 23. The data values in Table 21 are represented as the percent fluorescence decrease with time. Fluorescence readings for the three conjugates were taken at 565 nm, 585 nm, and 800 nm, respectively. Negative values indicate an increase in fluorescence.

TABLE 21

| QdotXXX-30N-Ms MAb Conjugate | Conjugate Diluent | Qdot Fluorescence (% Change) | | | | |
|---|---|---|---|---|---|---|
| | | 1.25 h | 3.25 h | 7.0 h | 23.5 h | 24.5 h |
| 565 | A | 11.18 | 13.50 | 18.78 | 16.99 | 19.93 |
| 565 | B | 10.47 | 10.58 | 14.51 | 17.57 | 19.98 |
| 565 | C | 7.30 | 7.62 | 13.77 | 16.23 | 20.39 |
| 585 | A | 10.44 | 13.28 | 17.84 | 17.96 | 19.46 |
| 585 | B | 10.08 | 11.26 | 15.77 | 17.51 | 19.60 |
| 585 | C | 7.47 | 8.76 | 12.94 | 15.80 | 17.80 |
| 800 | A | −12.52 | −13.53 | −9.67 | −18.66 | −13.36 |
| 800 | B | −11.70 | −14.47 | −10.82 | −18.87 | −14.71 |
| 800 | C | −14.01 | −16.13 | −12.53 | −19.76 | −14.51 |

A similar change in fluorescence was observed for the Qdot™-antibody conjugates relative to the data from the nanocrystals in Table 19. The greatest loss in the observed fluorescence was with Qdot™585-30N-Ms MAb antibody conjugate. An increase in the relative fluorescence for Qdot™800-30N-Ms MAb conjugate was observed. For each Qdot™-antibody conjugate, there was a different buffer in which it had the least decrease in fluorescence. In addition, a net settling of material was observed for some conjugates. In the case of Qdot™585 and Qdot™800 conjugates, mixing increased the relative fluorescence of the sample. Clearly, aggregation and settling of these conjugates is occurring in solution under diluted conditions.

Example 9

Figure 24:
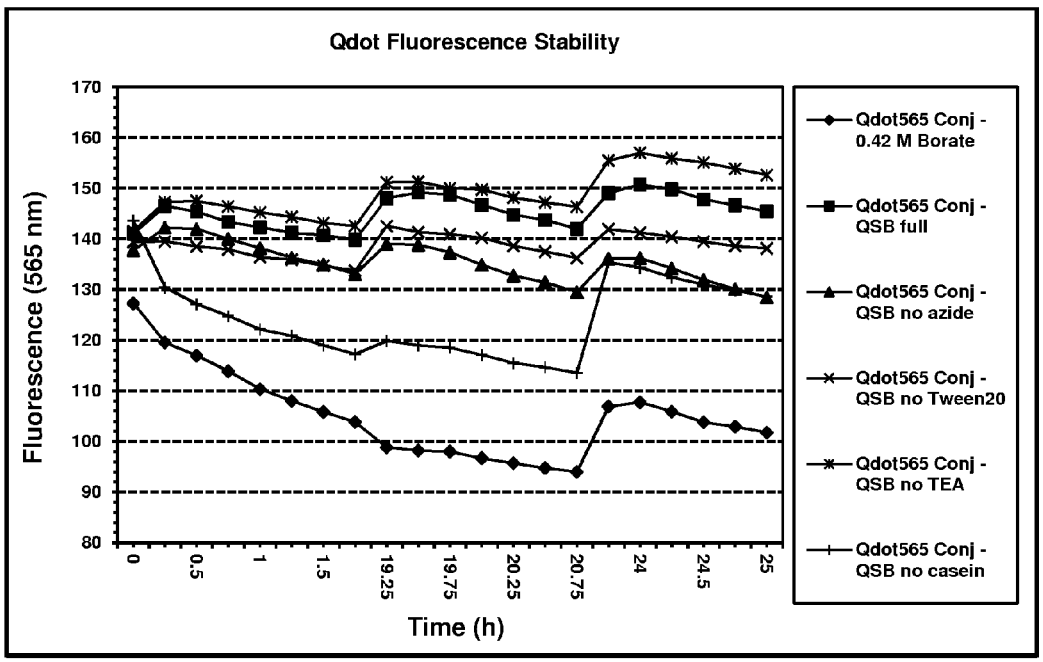
FIG. 24 is a graph of fluorescence light units at 565 nm versus time for a Qdot™565-30N-Ms MAb conjugate in various deconstructed Qdot™ stabilization buffer compositions.
Figure 25:
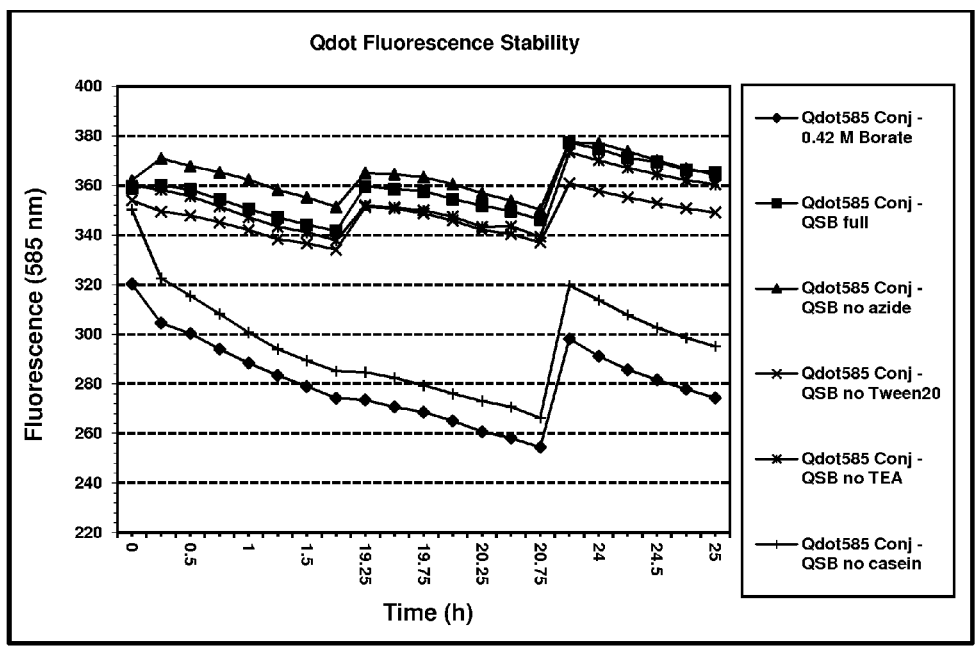
FIG. 25 is a graph of fluorescence light units at 585 nm versus time for a Qdot™585-30N-Ms MAb conjugate in various deconstructed Qdot™ stabilization buffer compositions.
Figure 26:
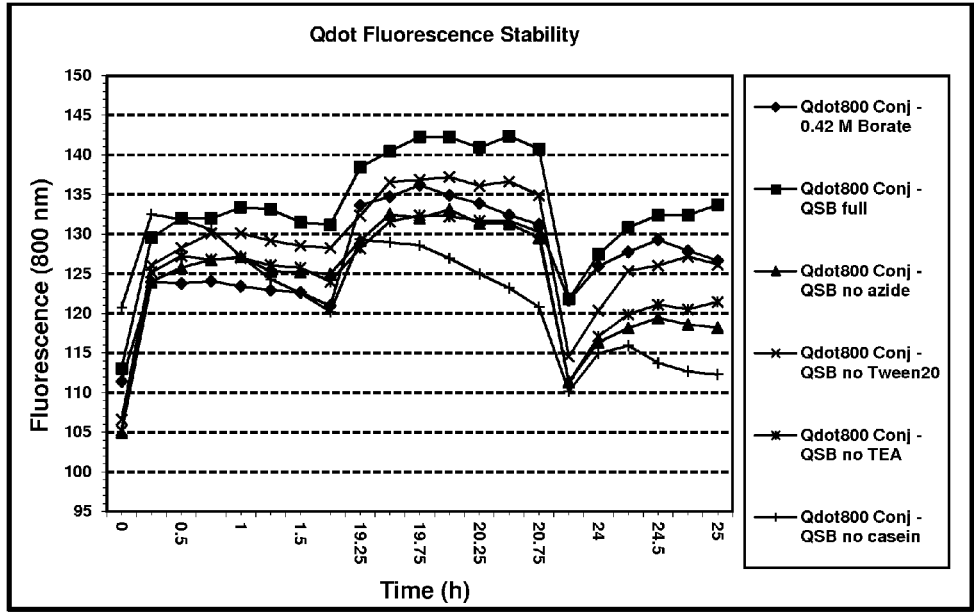
FIG. 26 is a graph of fluorescence light units at 800 nm versus time for a Qdot™800-30N-Ms MAb conjugate in various deconstructed Qdot™ stabilization buffer compositions.
Figure 27:
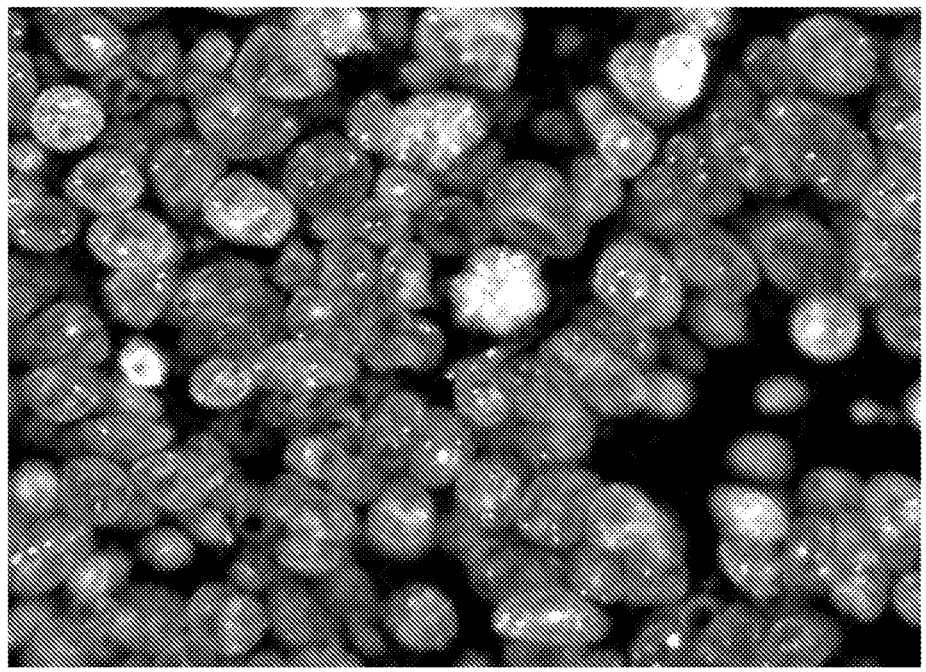
FIG. 27 is a composite spectral image, magnification 40×, illustrating FISH staining of Qdot™565-30N Ms MAb (conjugate in a Qdot™ stabilization buffer composition on prostate cancer cells at 0 days.
Figure 28:
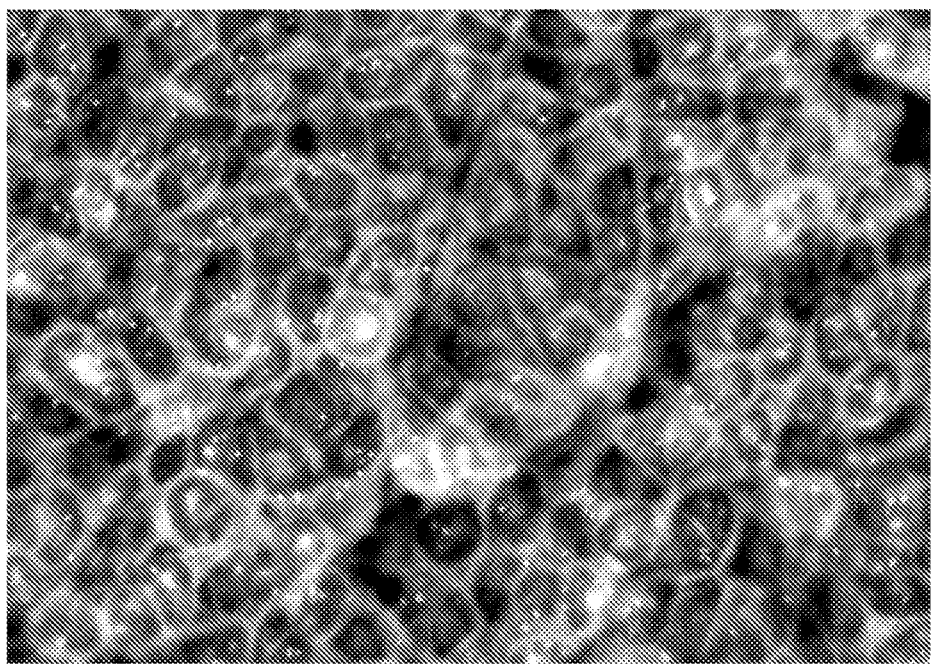
FIG. 28 is a composite spectral image, magnification 40×, illustrating FISH staining of Qdot™565-30N-MsAntiHapten conjugate in Solution A on prostate cancer cells at 0 days.
Figure 29:
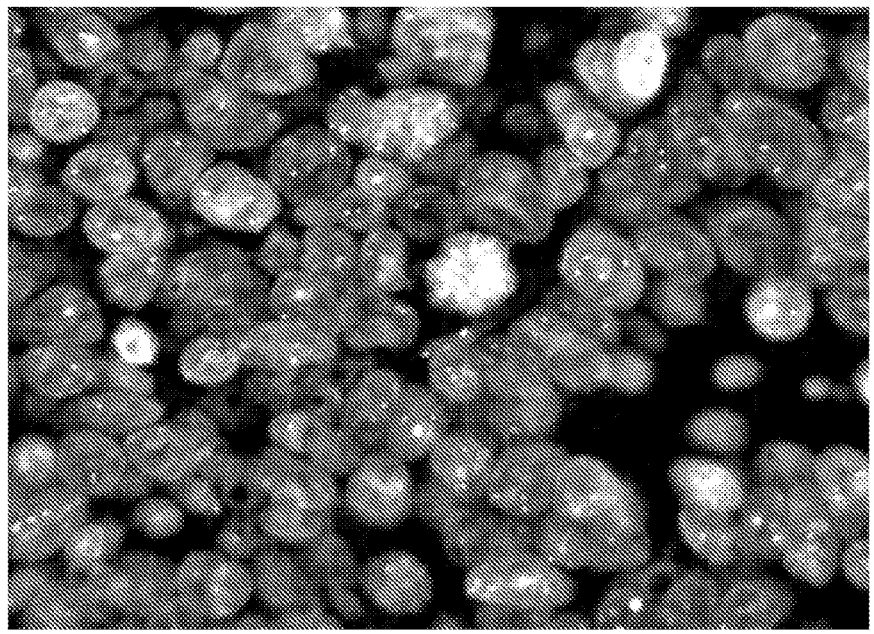
FIG. 29 is a composite spectral image, magnification 40×, illustrating FISH staining of Qdot™565-30N-MsAntiHapten conjugate in a Qdot™ stabilization buffer composition on prostate cancer cells after 1 month.
Figure 30:
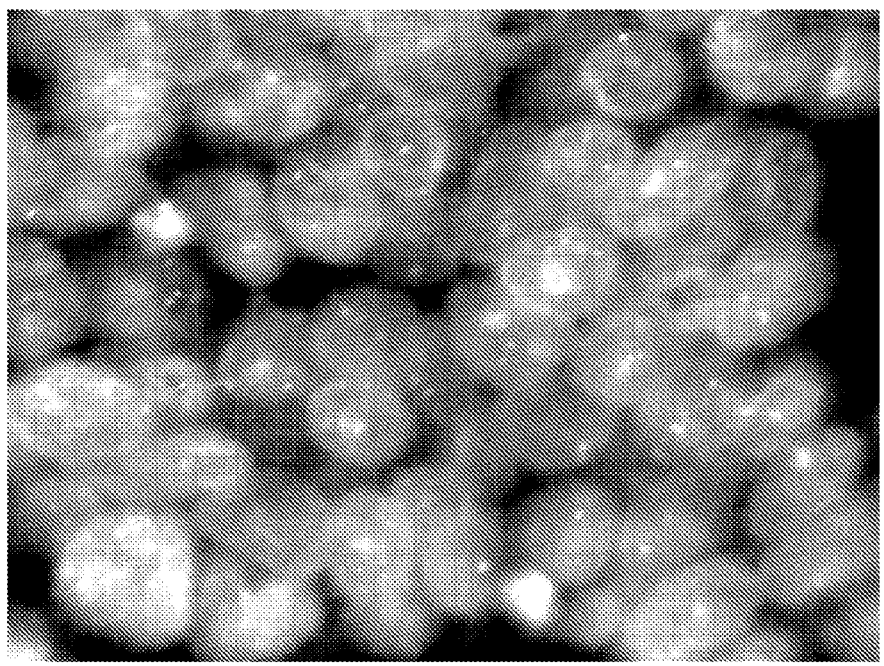
FIG. 30 is a composite spectral image, magnification 40×, illustrating FISH staining of Qdot™565-30N-MsAntiHapten conjugate in Solution A on prostate cancer cells after 1 month.

Stability of Qdot™565-30N-30N-MsAntiNP Conjugates in Deconstructed Qdot™ Stabilization Buffers A study was performed to examine the relative change in observed fluorescence of Qdot™-antibody conjugates in deconstructed versions of QSB containing 0.08 wt % sodium azide. In each case, the QSB buffer was reformulated by removing a single component of the buffer and testing it against the same Qdot™-30N-Ms MAb conjugates from Example 8C. Fluorescence data was acquired using a Varioskan spectral scanning multimode plate reader. The results are shown below in Tables 22-23 and FIGS. 24-26. In FIG. 24, $\lambda_{ex}$=400 nm, $\lambda_{em}$=565 nm; in FIG. 25, $\lambda_{ex}$=400 nm, $\lambda_{em}$=585 nm; in FIG. 26, $\lambda_{ex}$=400 nm, $\lambda_{em}$=655 nm. The data values in Table 22 are represented as the percent fluorescence decrease with time. Negative values indicate an increase in fluorescence.

TABLE 22

| Qdot Conjugate | Buffer Formulation | 1.75 h | 20.75 h | 25.0 h | FINAL RANK |
|---|---|---|---|---|---|
| Qdot565-30N-Ms Mab | A | 18.40 | 26.15 | 20.05 | 6 |
| | B | 0.84 | −0.69 | −3.14 | 2 |
| | C | 3.41 | 5.98 | 6.74 | 4 |
| | D | 4.07 | 2.26 | 0.91 | 3 |
| | E | −0.71 | −3.41 | −7.83 | 1 |
| | F | 18.36 | 20.92 | 10.43 | 5 |
| Qdot585-30N-Ms Mab | A | 14.37 | 20.58 | 14.35 | 5 |
| | B | 4.81 | 3.53 | −1.75 | 1 |
| | C | 2.95 | 3.27 | −0.62 | 2 |
| | D | 5.63 | 4.81 | 1.40 | 4 |
| | E | 6.14 | 5.74 | −0.13 | 3 |
| | F | 18.60 | 24.00 | 15.74 | 6 |
| Qdot800-30N-Ms Mab | A | −8.57 | −17.79 | −13.69 | 4 |
| | B | −16.00 | −24.48 | −18.25 | 2 |
| | C | −19.04 | −23.40 | −12.58 | 5 |
| | D | −20.30 | −26.56 | −18.34 | 1 |
| | E | −17.84 | −23.81 | −15.42 | 3 |
| | F | 0.49 | −0.04 | 7.04 | 6 |

TABLE 23

| Buffer Formulation | Total Rank Pts. | Final Rank |
|---|---|---|
| A: 50 mM Borate Buffer | 15 | 5 |
| B: New Qdot Stabilization Buffer | 5 | 1 |
| C: New Qdot Stabilization Buffer w/out Sodium Azide | 11 | 4 |
| D: New Qdot Stabilization Buffer w/out Tween20 | 8 | 3 |
| E: New Qdot Stabilization Buffer w/out Triethanolamine | 7 | 2 |
| F: New Qdot Stabilization Buffer w/out Casein Base Hydrolysates | 17 | 6 |

In each case, the buffers were ranked from 1 (best) to 6 (worst) relative to the overall fluorescence change of the conjugate. A total was created by adding up the ranking across all three conjugates. A summary of the final ranking is shown in Table 23. For all of the Qdot™-30N-Ms MAb conjugates, a similar trend for relative fluorescence change was observed for each buffer system with minor variations in the order of their ranking. Overall, the best buffer was the Qdot™ Stabilization Buffer containing 0.08 wt % sodium azide. In a couple of cases, the QSB buffer with a deleted component provided a better result than the full QSB due to the individual stability characteristics of each Qdot™ nanocrystal, as previously discussed. In both cases, the full QSB provided the second best result. The primary component which appears to have the largest influence on the stability of the Qdot™-antibody conjugates is casein base hydrolysates. In Table 6, it was demonstrated in several buffers that Qdot™ fluorescence signal intensity is stabilized in solution by the addition of casein base hydrolysates. This was further demonstrated in control pH diluents.

Several components, including triethanolamine, casein base hydrolysates, Tween® 20, and sodium azide, appeared to increase the fluorescence of at least some Qdot™s and Qdot™ conjugates. For example, a QSB composition comprising 50 mM triethanolamine increased initial fluorescence of a Qdot™800-30N-MS-Mab conjugate by 6% relative to a QSB composition with the same composition other than the absence of triethanolamine. After 25 hours, the fluorescence of the Qdot™800-30N-MS-Mab conjugate in the QSB composition with triethanolamine was 10% greater than the fluorescence in the QSB composition without triethanolamine.

A Qdot™565-30N-MS-Mab conjugate stored in a QSB composition comprising 1.05 wt % casein base hydrolysates for 25 hours had a fluorescence that was 14% greater than the fluorescence of a Qdot™565-30N-MS-Mab conjugate stored in a QSB composition with the same composition other than the absence of casein base hydrolysates. Similarly a Qdot™800-30N-MS-Mab conjugate stored in a QSB composition with casein base hydrolysates for 25 hours had a fluorescence that was 20% greater than the fluorescence in a QSB composition without casein base hydrolysates, and a Qdot™585-30N-MS-Mab conjugate had a fluorescence that was 27% greater than the fluorescence in a QSB composition without casein base hydrolysates. The presence of casein base hydrolysates stabilizes fluorescence by minimizing quantum dot aggregation and maintaining the quantum dot solubility in the solution.

A Qdot™800-30N-MS-Mab conjugate stored in a QSB composition with 0.005 wt % Tween® 20 had an initial fluorescence that was 6% greater than the fluorescence of a Qdot™800-30N-MS-Mab conjugate stored in a QSB composition with the same composition other than the absence of Tween® 20. The Qdot™800-30N-MS-Mab conjugate stored in a QSB composition with 0.005 wt % Tween® 20 for 25 hours also had a fluorescence that was 6% greater than the fluorescence in a QSB composition without Tween® 20. A Qdot™565-30N-MS-Mab conjugate stored in a QSB composition comprising 0.005 wt % Tween® 20 for 25 hours had a fluorescence that was 6% greater than the fluorescence of a Qdot™565-30N-MS-Mab conjugate stored in a QSB composition without Tween® 20. A Qdot™585-30N-MS-Mab conjugate stored in a QSB composition comprising 0.005 wt % Tween® 20 for 25 hours had a fluorescence that was 5% greater than the fluorescence of a Qdot™585-30N-MS-Mab conjugate stored in a QSB composition without Tween® 20.

A Qdot™800-30N-MS-Mab conjugate stored in a QSB composition with 0.08 wt % sodium azide had an initial fluorescence that was 6% greater than the fluorescence in a QSB composition without sodium azide. The Qdot™800-30N-MS-Mab conjugate stored in a QSB composition with 0.08 wt % sodium azide for 25 hours had a fluorescence that was 14% greater than the fluorescence in a QSB composition without sodium azide. A Qdot™565-30N-MS-Mab conjugate stored in a QSB composition comprising 0.08 wt % sodium azide for 25 hours had a fluorescence that was 14% greater than the fluorescence of a Qdot™565-30N-MS-Mab conjugate stored in a QSB composition with the same composition other than the absence of sodium azide.

Example 10

Final Formulation of Qdot™ Stabilization Buffer

The final formulation of QSB is shown below for a 100 mL aliquot of QSB containing 0.08 wt % sodium azide. The final pH was adjusted to pH=8.3.

75 mL of 0.42 M borate buffer, pH=8.3 (final ~0.32 mM borate)
25 mL of casein base hydrolysate (42 mg/mL casein stock, final ~1.05 wt %)
664 µL of triethanolamine (~50 mM)
80 mg of sodium azide (~0.08 wt %)
5 µL of Tween® 20 (~0.005 wt %)

Example 11

Qdot™-Antibody Conjugate Staining

A. Parameters for Evaluating Staining of Qdot™565-30N-MsAntiHapten Conjugates

The functional performance of the Qdot™ 565-30N-SMCC-MsAntiHapten conjugate was evaluated in a FISH assay diluted in either Qdot™ Stabilization Buffer (QSB) or Solution A. The FISH assay was performed in a fully automated manner on a Benchmark XT Instrument.

Test sample: A 4 µm thick, FFPET (formalin-fixed paraffin-embedded tissue), xenograft section determined to exhibit a genomic translocation correlated with prostate cancer was used. The prostate cancer cell line originated from the vertebral metastasis of a prostate cancer case. The cells exhibit polysomy, 3'-ERG-5'-ERG break apart and 3'-ERG amplification.

FISH assay: The hybridization was performed at 52° C. for 8 h, and the stringency washes were done at 72° C. in 2×SSC (3×8 min).

Probe: A repeat-depleted 5'-ERG-Hapten probe was used at a 40 µg/ml concentration.

Detection: The Qdot™565-30N-MSAntiHapten conjugate solution was diluted to a 50 nM concentration in either QSB (formulation from Example 10) or Solution A. After formulation, the diluted conjugate solution was stored at 4° C. The samples were tested monthly in an automated FISH assay on a BenchMark XT instrument. Composite spectral images at 40× magnification were obtained.

B. Staining Results for Qdot™565-30N-MsAntiHapten Conjugate in Qdot™ Stabilization Buffer (QSB)

Figure 31:
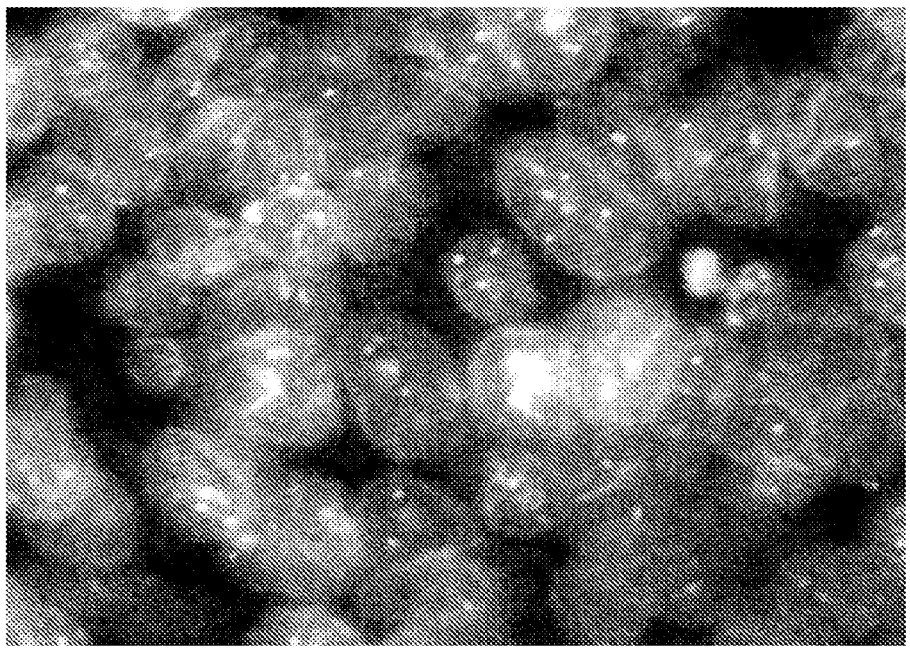
FIG. 31 is a composite spectral image, magnification 40×, illustrating FISH staining of Qdot™565-30N-MsAntiHapten conjugate in a Qdot™ stabilization buffer composition on prostate cancer cells after 3 months.
Figure 32:
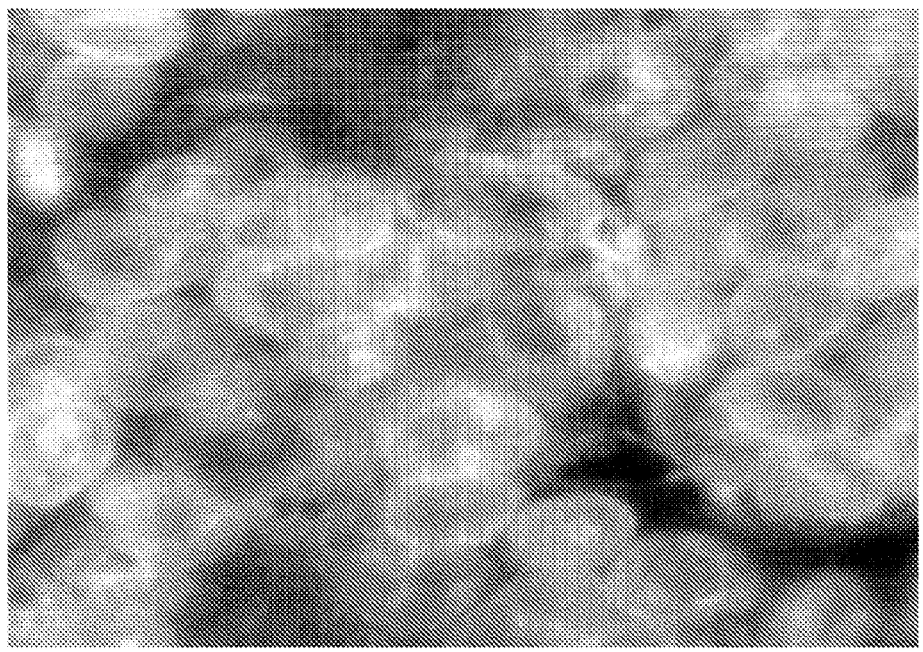
FIG. 32 is a composite spectral image, magnification 40×, illustrating FISH staining of Qdot™565-30N-MsAntiHapten conjugate in Solution A on prostate cancer cells after 3 months.
Figure 33:
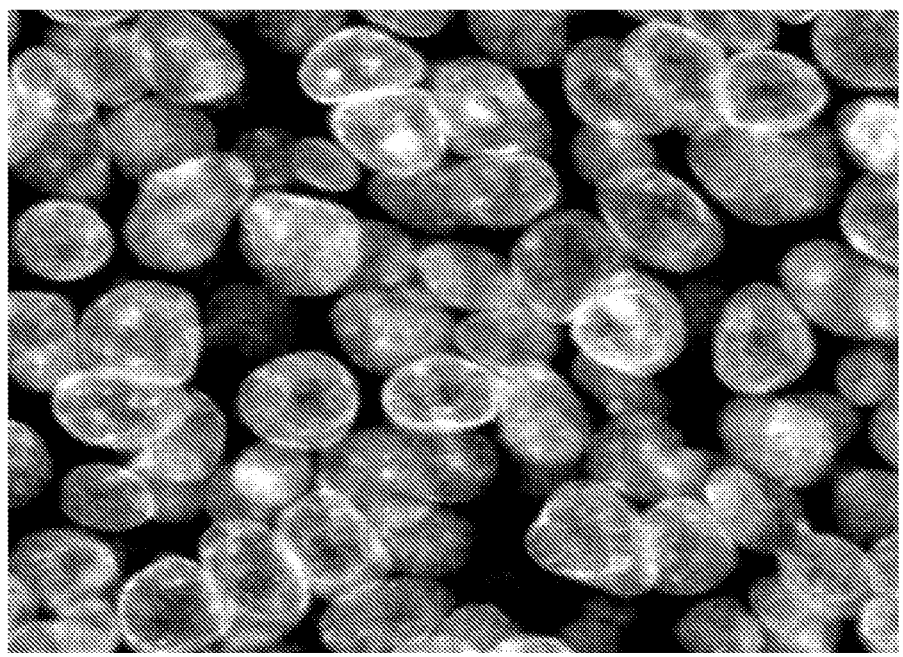
FIG. 33 is a composite spectral image, magnification 40×, illustrating FISH staining of Qdot™565-30N-MsAntiHapten conjugate in a Qdot™ stabilization buffer composition on prostate cancer cells after 6 months.
Figure 34:
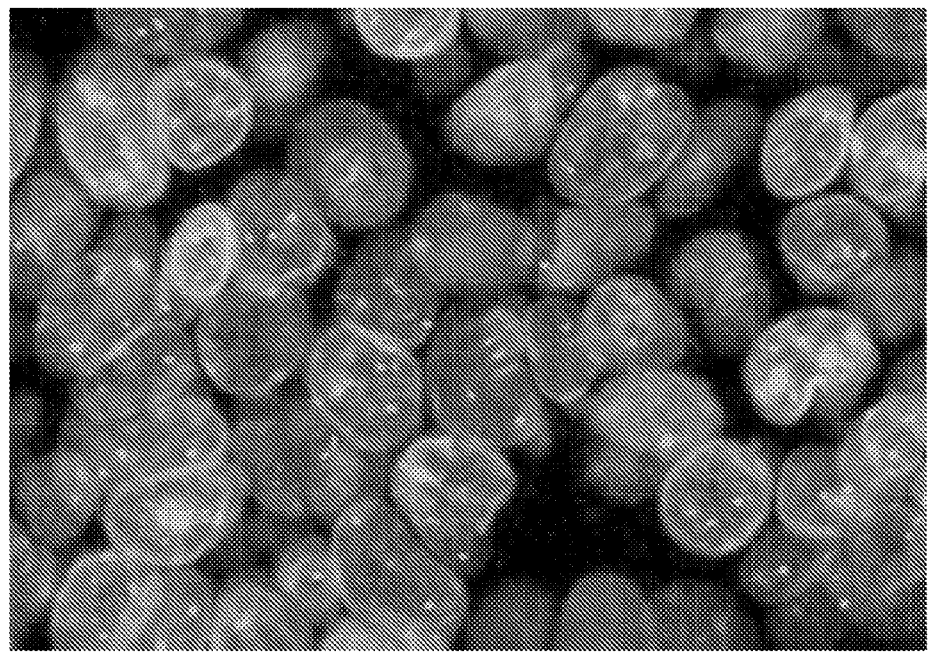
FIG. 34 is a standard FISH image of Qdot™565-30N-MsAntiHapten conjugate in a Qdot™ stabilization buffer composition on prostate cancer cells after 6 months.

The Qdot™565-30N-MsAntiHapten conjugate produced a brighter FISH signal in QSB throughout the observed 6-month time period. Representations of the FISH tissue staining are found in FIGS. 27-33. FIGS. 27-33 are composite spectral images (CSI) at 40× magnification. FIG. 34 is a standard FISH image. (A FISH image is a sequential image acquired with narrow band micron filters. The CSI image is a spectral image composed of acquisition of the entire visible spectrum at regular sampled intervals.) The results in QSB and Solution A were evaluated at 0 days (FIGS. 27-28), 1 month (FIGS. 29-30), and 3 months (FIGS. 31-32). FIGS. 33-34 illustrate the results in QSB at 6 months. At the 1-month time point, the FISH signal intensity began to decrease noticeably for the conjugate in the Solution A. The QSB preserved the original signal intensity through the 3-month time point. A mild decrease in signal intensity was detected at 6 months.

The staining was evaluated using pathology scoring criteria. A positive signal is seen as a bright, circular dot (diameter ~0.1 μm-0.5 μm) in the nucleus of the cells. The dots appear in a dark background, and occur as a single, dual, or multiple configuration. The brightness intensity in a dark field was scored on a scale of 0-3, as outlined in Table 24. A summary of the results is provided in Table 25.

TABLE 24

| Score Level | Scoring Criteria |
|---|---|
| 3+ | Very bright, strong signal in the whole view field, virtually every nucleus contains signal |
| 2+ | Medium brightness in the whole view field, virtually every nucleus contains signal |
| 1+ | Low brightness, and only focally present |

TABLE 25

| | Staining Diluent | |
|---|---|---|
| Timepoint | QSB | Solution A |
| 0 Days | 3+ | 3+ |
| 1 Month | 3+ | 2+ |
| 2 Months | 2+ | 1+ |
| 3 Months | 3+ | 0 |
| 4 Months | 2+ | 0 |
| 5 Months | 2+ | 0 |
| 6 Months | 2+ | 0 |

Pathology scoring was on a scale of 0-3, with 3 representing the greatest signal intensity.

In addition to the staining results presented above, all samples which failed to provide adequate staining were analyzed for potential changes in their fluorescence, antibody kinetic activity and aggregation. In each failure case, no significant changes were observed in the relative luminescence or wavelength for fluorescent emission in either buffer. In addition, analysis of the samples by BioLayer Interferometry (BLI) revealed no significant loss of antibody avidity for the hapten probe label.

Two conjugates were evaluated in Solution A under stressed conditions. An aliquot of the conjugate from the stressed conditions was dispensed and coverslipped on a slide. Samples were stressed for 10 days at 37° C., and were stored at 4° C. It was noticed that discrete aggregates of the conjugate formed within the sample, and staining was reduced. Aggregation most likely inhibits staining by both limiting the amount of reagent in solution and making the conjugate too big to enter a cell. In contrast, when Qdot™ conjugates in QSB buffer were evaluated under the same conditions, there was less aggregation of the conjugates.

The following patents and applications are considered to be part of the disclosure of this application and are incorporated herein by reference: U.S. patent application Ser. No. 11/800,360 (U.S. Publication No. 2008/0274463), filed May 4, 2007, U.S. patent application Ser. No. 11/849,060 (U.S. Publication No. 2008/0057513), filed Aug. 31, 2007, U.S. patent application Ser. No. 11/982,627 (U.S. Publication No. 2008/0268562), filed Nov. 1, 2007, U.S. patent application Ser. No. 11/999,914 (U.S. Publication No. 2008/0212866), filed Dec. 6, 2007, U.S. patent application Ser. No. 12/154,472 (U.S. Publication No. 2008/0305497), filed May 22, 2008, PCT Application No. PCT/US2009/045841 (WO 2009/149013), filed Jun. 1, 2009, PCT Application No. PCT/US2009/054614, filed Aug. 21, 2009, and U.S. Provisional Application No. 61/288,226, filed Dec. 18, 2009.

Embodiments of a composition for stabilizing a fluorescent particle include (a) a substituted amine other than an amino acid or an alkyl-substituted alkyl amine or (b) an amine and a protein and/or protein hydrolysate, wherein at least one of the amine or the protein and/or protein hydrolysate is present at a concentration effective to stabilize and/or increase fluorescence intensity of a fluorescent particle stored in the composition relative to fluorescence intensity of the fluorescent particle stored in a composition devoid of (a) a substituted amine other than an amino acid or an alkyl-substituted alkyl amine or (b) an amine and a protein and/or protein hydrolysate. In some embodiments, the composition further comprises a borate buffer, and the composition has a pH greater than or equal to 7. In any or all of the above embodiments, the composition may further include a preservative and a surfactant.

In any or all of the above embodiments, the composition may comprise 0.02 M to 0.5 M borate, 0.05 wt % to 1.5 wt % protein and/or protein hydrolysate, 25 mM to 200 mM amine, 0.05 wt % to 0.2 wt % preservative, and 0.005 wt % to 0.05 wt % surfactant.

In any or all of the above embodiments, the amine may be a substituted amine having the formula $R_nNH_{(3-n)}$, where n=1, 2, or 3, each R is independently an aliphatic group, a heteroaliphatic group, an aryl group, a heteroaryl group, an alkyl aryl group, or an aryl alkyl group, and at least one R is substituted. In some embodiments, at least one R is substituted with one or more —OH, —OR$_1$, —CO$_2$R$_1$, —CN groups, or combinations thereof, where R$_1$ is a substituted or unsubstituted aliphatic or aryl group.

In any or all of the above embodiments, the amine may be an alkanolamine. In any or all of the above embodiments, the amine may be an N-ethanol substituted amine, such as ethanolamine, diethanolamine, triethanolamine, N-methyldiethanolamine, N,N-dimethylethanolamine, or a combination thereof. In any or all of the above embodiments, the amine may be an N-ethanol substituted amine with a concentration in the range of 50 mM to 100 mM.

In any or all of the above embodiments, the amine may be a substituted tertiary alkyl amine.

In any or all of the above embodiments, the protein and/or protein hydrolysate may be vegetable tryptone, salmon peptone, casein hydrolysates, chicken albumin hydrolysates, gelatin from fish skin, or a combination thereof. In any or all of the above embodiments, the preservative may be a) sodium azide, b) a preservative composition comprising 9.5-9.9% 2-methyl-4-isothiazolin-3-one, c) a preservative composition comprising 2.3% 5-chloro-2-methyl-4-isothiazolin-3-one, 0.7% 2-methyl-4-isothiazolin-3-one, 2-3% alkyl carboxylate, and 93-95% modified glycol, or d) a combination thereof.

In any or all of the above embodiments, the surfactant may be a nonionic surfactant. In some embodiments, the surfactant is an alkylene glycol or oxygenated alkylene glycol, such as polyethylene glycol sorbitan monolaurate, polyethylene glycol p-(1,1,3,3-tetramethylbutyl)-phenyl ether), or polyoxyethyleneglycol dodecyl ether.

In any or all of the above embodiments, the composition may have a pH of 7 to 9, or a pH of 8 to 9.

In any or all of the above embodiments, the composition may further include a fluorescent particle, wherein fluorescence intensity of the fluorescent particle is increased relative to fluorescence intensity of the fluorescent particle in a composition devoid of (a) a substituted amine other than an amino acid or an alkyl-substituted alkyl amine or (b) an amine and a protein and/or protein hydrolysate. In some embodiments, fluorescence intensity, at a time subsequent to mixing the fluorescent particle with the composition, is increased at least 5% relative to fluorescence intensity of the fluorescent particle in a composition devoid of (a) a substituted amine other than an amino acid or an alkyl-substituted alkyl amine or (b) an amine and a protein and/or protein hydrolysate.

In some embodiments, the fluorescent particle is a quantum dot or quantum dot conjugate, and the composition includes 0.32 M borate, 1.05 wt % casein hydrolysates, 50 mM triethanolamine, 0.08 wt % sodium azide, and 0.005 wt % polyethylene glycol sorbitan monolaurate, and the composition has a pH of 8 to 8.5.

Embodiments of a method for stabilizing a fluorescent particle include providing a fluorescent particle solution comprising at least one fluorescent particle, and diluting the fluorescent particle solution in a composition to provide a diluted fluorescent particle solution, wherein the composition comprises (a) a substituted amine other than an amino acid or an alkyl-substituted alkyl amine or (b) an amine and a protein and/or protein hydrolysate, wherein at least one of the amine or the protein and/or protein hydrolysate is present at a concentration effective to stabilize and/or increase fluorescence of the fluorescent particle.

In some embodiments, diluting the fluorescent particle solution in the composition increases fluorescence intensity of the diluted fluorescent particle solution relative to fluorescence intensity of a diluted fluorescent particle solution formed by diluting the fluorescent particle solution in a composition devoid of (a) a substituted amine other than an amino acid or an alkyl-substituted alkyl amine or (b) an amine and a protein and/or protein hydrolysate. In particular embodiments, fluorescence intensity of the diluted fluorescent particle solution, at a time subsequent to diluting the fluorescent particle solution in the composition, is increased at least 5% relative to fluorescence intensity of a diluted fluorescent particle solution formed by diluting the fluorescent particle solution in a composition devoid of (a) a substituted amine other than an amino acid or an alkyl-substituted alkyl amine or (b) an amine and a protein and/or protein hydrolysate.

In any or all of the above embodiments, the composition may further comprise a borate buffer, a preservative, and a surfactant, and the composition may have a pH greater than or equal to 7. In any or all of the above embodiments, the composition may include 0.05 M to 0.5 M borate, 0.05 wt % to 1.1 wt % protein and/or protein hydrolysate, 50 mM to 100 mM amine, 0.05 wt % to 0.2 wt % preservative, and 0.005 wt % to 0.05 wt % nonionic surfactant. In any or all of the above embodiments, the amine may be an N-ethanol substituted amine.

In any or all of the above embodiments, the method further includes storing the diluted fluorescent particle solution at 4° C. In some embodiments, fluorescence intensity of the diluted fluorescent particle solution remains substantially the same after storage at 4° C. for one month. In certain embodiments, fluorescence intensity of the diluted fluorescent particle solution remains substantially the same after storage at 4° C. for three months.

In any or all of the above embodiments, the fluorescent particle solution may be a quantum dot conjugate solution comprising at least one quantum dot conjugate, and the quantum dot conjugate solution is diluted to a concentration of 0.5 nM to 150 nM to provide a diluted quantum dot conjugate solution.

In some embodiments, the diluted quantum dot conjugate solution is used to detect a probe hybridized to a target. In certain embodiments, the quantum dot conjugate is a quantum dot-antibody conjugate, and the method further includes hybridizing the probe to the target to provide a hybridized probe; providing a diluted quantum dot-antibody conjugate solution, wherein the diluted quantum dot-antibody conjugate solution comprises 5 nM to 100 nM quantum dot-antibody conjugate, 0.05 M to 0.5 M borate, 0.05 wt % to 1.1 wt % protein and/or protein hydrolysate, 50 mM to 100 mM N-ethanol substituted amine, 0.05 wt % to 0.1 wt % sodium azide, and 0.005 wt % to 0.05 wt % nonionic surfactant and having a pH of 8-9, wherein the quantum dot-antibody conjugate is capable of binding to the probe; combining the diluted quantum dot-antibody conjugate solution with the hybridized probe; and detecting fluorescence of the quantum dot-antibody conjugate.

In some embodiments, the diluted quantum dot conjugate solution is used to detect a protein antigen on a tissue sample. In certain embodiments, the quantum dot conjugate is a quantum dot-antibody conjugate, and the method further includes providing a diluted quantum dot-antibody conjugate solution, wherein the diluted quantum dot-antibody conjugate solution comprises 5 nM to 100 nM quantum dot-antibody conjugate, 0.05 M to 0.5 M borate, 0.05 wt % to 1.1 wt % protein and/or protein hydrolysate, 50 mM to 100 mM N-ethanol substituted amine, 0.05 wt % to 0.1 wt % sodium azide, and 0.005 wt % to 0.05 wt % nonionic surfactant and having a pH of 8-9, wherein the quantum dot-antibody conjugate is capable of binding to the protein antigen; combining the diluted quantum dot-antibody conjugate solution with the tissue sample; and detecting fluorescence of the quantum dot-antibody conjugate.

In some embodiments, the diluted quantum dot-antibody conjugate solution has a pH in the range of 8 to 8.5 and comprises 5 nM to 100 nM quantum dot-antibody conjugate, 0.32 M borate, 1.0 wt % casein hydrolysates, 50 mM triethanolamine, 0.08 wt % sodium azide, and 0.005 wt % polyethylene glycol sorbitan monolaurate. In some embodiments, the diluted quantum dot-antibody conjugate solution is stored at 4° C. prior to use. In some embodiments, fluorescence intensity of the diluted quantum dot-antibody conjugate solution remains substantially the same after one month in storage at 4° C. In certain embodiments, fluorescence intensity of the diluted quantum dot-antibody conjugate solution remains substantially the same after three months in storage at 4° C.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition for stabilizing a quantum dot fluorescent particle or a quantum dot conjugate fluorescent particle, the composition having a pH greater than or equal to 7, the composition comprising:
(a) (i) a substituted amine, other than an amino acid or an alkyl-substituted alkyl amine, the substituted amine having a formula $R_nNH_{(3-n)}$, where n=1, 2, or 3, each R is independently an aliphatic group, a heteroaliphatic group, an aryl group, a heteroaryl group, an alkyl aryl group, or an aryl alkyl group, and at least one R is substituted with one or more —OH, —$OR_1$, —$CO_2R_1$, —CN groups, or combinations thereof, where $R_1$ is a substituted or unsubstituted aliphatic or aryl group, or (ii) an amine and a protein and/or protein hydrolysate, wherein at least one of the substituted amine, the amine, or the protein and/or protein hydrolysate is present at a concentration effective to stabilize and/or increase fluorescence intensity of a fluorescent particle stored in the composition relative to fluorescence intensity of the fluorescent particle stored in a composition devoid of (i) a substituted amine other than an amino acid or an alkyl-substituted alkyl amine, or (ii) an amine and a protein and/or protein hydrolysate;
(b) a borate buffer comprising a salt concentration of from greater than zero to 2 M;
(c) a preservative; and
(d) a surfactant.

2. The composition of claim 1, comprising:
0.02 M to 0.5 M borate;
0.05 wt % to 1.5 wt % protein and/or protein hydrolysate;
25 mM to 200 mM amine;
0.05 wt % to 0.2 wt % preservative; and
0.005 wt % to 0.05 wt % surfactant.

3. The composition of claim 1, where the amine is a substituted amine having the formula $R_nNH_{(3-n)}$, where n=1, 2, or 3, each R is independently an aliphatic group, a heteroaliphatic group, an aryl group, a heteroaryl group, an alkyl aryl group, or an aryl alkyl group, and at least one R is substituted.

4. The composition of claim 3, where at least one R is substituted with one or more —OH, —$OR_1$, —$CO_2R_1$, —CN groups, or combinations thereof, where $R_1$ is a substituted or unsubstituted aliphatic or aryl group.

5. The composition of claim 1, where the amine comprises an N-ethanol substituted amine.

6. The composition of claim 1, where the amine is ethanolamine, diethanolamine, triethanolamine, N-methyldiethanolamine, N,N-dimethylethanolamine, or a combination thereof.

7. The composition of claim 1, where the protein and/or protein hydrolysate is vegetable tryptone, salmon peptone, chicken albumin hydrolysates, casein hydrolysates, gelatin from fish skin, or a combination thereof.

8. The composition of claim 1, where the preservative is sodium azide, a preservative composition comprising 9.5-9.9% 2-methyl-4-isothiazolin-3-one, a preservative composition comprising 2.3% 5-chloro-2-methyl-4-isothiazolin-3-one, 0.7-% 2-methyl-4-isothiazolin-3-one, 2-3% alkyl carboxylate, 93-95% modified glycol, or a combination thereof.

9. The composition of claim 1, where the surfactant is a nonionic surfactant.

10. The composition of claim 9, where the surfactant is polyethylene glycol sorbitan monolaurate, polyethylene glycol p-(1,1,3,3-tetramethylbutyl)-phenyl ether), or polyoxyethyleneglycol dodecyl ether.

11. The composition of claim 1, where the composition has a pH of 7 to 9.

12. The composition of claim 1, further comprising a fluorescent particle selected from a quantum dot fluorescent particle or a quantum dot conjugate fluorescent particle, wherein fluorescence intensity of the fluorescent particle is increased relative to fluorescence intensity of the fluorescent particle in a composition devoid of (i) a substituted amine other than an amino acid or an alkyl-substituted alkyl amine, or (ii) an amine and a protein and/or protein hydrolysate.

13. The composition of claim 12, where fluorescence intensity, at a time subsequent to mixing the fluorescent particle with the composition, is increased at least 5% relative to fluorescence intensity of the fluorescent particle in a composition devoid of (i) a substituted amine other than an amino acid or an alkyl-substituted alkyl amine, or (ii) an amine and a protein and/or protein hydrolysate.

14. A composition for stabilizing a quantum dot fluorescent particle or a quantum dot conjugate fluorescent particle, the composition comprising:
a quantum dot fluorescent particle or a quantum dot conjugate fluorescent particle;
0.3 M borate;
1 wt % casein hydrolysates;
50 mM triethanolamine;
0.08 wt % sodium azide; and
0.005 wt % polyethylene glycol sorbitan monolaurate, wherein the composition has a pH of 8 to 8.5;
wherein fluorescence intensity of the quantum dot fluorescent particle or quantum dot conjugate fluorescent particle is increased relative to fluorescence intensity of the fluorescent particle in a composition devoid of (i) a substituted amine other than an amino acid or an alkyl-substituted alkyl amine, or (ii) an amine and a protein and/or protein hydrolysate.

15. A method, comprising:
providing a fluorescent particle solution comprising at least one quantum dot fluorescent particle or quantum dot conjugate fluorescent particle; and
diluting the fluorescent particle solution in a composition to provide a diluted fluorescent particle solution, the composition having a pH greater than or equal to 7 and comprising (a) (i) a substituted amine, other than an amino acid or an alkyl-substituted alkyl amine, the substituted amine having the formula $R_nNH_{(3-n)}$, where n=1, 2, or 3, each R is independently an aliphatic group, a heteroaliphatic group, an aryl group, a heteroaryl group, an alkyl aryl group, or an aryl alkyl group, and at least one R is substituted with one or more —OH, —$OR_1$, —$CO_2R_1$, —CN groups, or combinations thereof, where $R_1$ is a substituted or unsubstituted aliphatic or aryl group, or (ii) an amine and a protein and/or protein hydrolysate, wherein at least one of the substituted amine, the amine or the protein and/or protein hydrolysate is present at a concentration effective to stabilize and/or increase fluorescence of the fluorescent particle; (b) a borate buffer comprising a salt concentration of from greater than zero to 2 M; (c) a preservative; and (d) a surfactant.

16. The method of claim 15, where fluorescence intensity of the diluted fluorescent particle solution, at a time subsequent to diluting the fluorescent particle solution in the composition, is increased at least 5% relative to fluorescence intensity of a diluted fluorescent particle solution formed by diluting the fluorescent particle solution in a composition devoid of a substituted amine other than an amino acid or an alkyl-substituted alkyl amine, or an amine and a protein and/or protein hydrolysate.

17. The method of claim 15, where the composition comprises 0.05 M to 0.5 M borate, 0.05 wt % to 1.1 wt % protein and/or protein hydrolysate, 50 mM to 100 mM amine, 0.05 wt % to 0.2 wt % preservative, and 0.005 wt % to 0.05 wt % nonionic surfactant.

18. The method of claim 15, further comprising storing the diluted fluorescent particle solution at 4° C.

19. The method of claim 18, where fluorescence intensity of the diluted fluorescent particle solution remains substantially the same after storage at 4° C. for one month.

20. The method of claim 15, where the fluorescent particle solution is a quantum dot conjugate solution comprising at least one quantum dot conjugate, and the quantum dot conjugate solution is diluted to a concentration of 0.5 nM to 150 nM to provide a diluted quantum dot conjugate solution.

21. The method of claim 15, further comprising using the diluted fluorescent particle solution to detect a probe hybridized to a target or to detect a protein antigen on a tissue sample, wherein the fluorescent particle is a quantum dot-antibody conjugate capable of specifically interacting with the probe or with the protein antigen,
wherein the composition has a pH greater than or equal to 7, and
wherein fluorescence intensity of the quantum dot-antibody conjugate is increased relative to fluorescence intensity of the quantum dot-antibody conjugate in a composition devoid of a substituted amine other than an amino acid or an alkyl-substituted amine, or an amine and a protein and/or protein hydrolysate.

22. The method of claim 21, where the fluorescent particle solution is diluted to provide a diluted fluorescent particle solution comprising 5 nM to 100 nM quantum dot-antibody conjugate, 0.05 M to 0.5 M borate, 0.05 wt % to 1.1 wt % protein and/or protein hydrolysate, 50 mM to 100 mM N-ethanol substituted amine, 0.05 wt % to 0.1 wt % sodium azide, and 0.005 wt % to 0.05 wt % nonionic surfactant and having a pH of 8-9.

23. The method of claim 22 where the diluted fluorescent particle solution has a pH in the range of 8 to 8.5 and comprises 5 nM to 100 nM quantum dot-antibody conjugate, 0.32 M borate, 1.0 wt % casein hydrolysates, 50 mM triethanolamine, 0.08 wt % sodium azide, and 0.005 wt % polyethylene glycol sorbitan monolaurate.

24. A composition for stabilizing a quantum dot fluorescent particle or a quantum dot conjugate fluorescent particle, the composition comprising:
(a) an alkyl amine wherein one or more alkyl groups are substituted with one or more —OH, —$CO_2R_1$, —CN groups, or combinations thereof, where $R_1$ is a substituted or unsubstituted aliphatic or aryl group;
(b) a protein and/or protein hydrolysate selected from vegetable tryptone, salmon peptone, chicken albumin hydrolysates, casein hydrolysates, gelatin from fish skin, or a combination thereof;
(c) a borate buffer comprising a salt concentration of from greater than zero to 2 M;
(d) a preservative selected from an isothiazolinone, a glycol, an azide, or a combination thereof; and
(e) a glycol surfactant.

25. The composition of claim 24, wherein:
the alkyl amine is selected from ethanolamine, diethanolamine, triethanolamine, N-methyldiethanolamine, or N,N-dimethylethanolamine;
the protein and/or protein hydrolysate is selected from vegetable tryptone, salmon peptone, chicken albumin hydrolysates, casein hydrolysates, gelatin from fish skin, or a combination thereof;
the preservative is an azide preservative; and
the glycol surfactant is selected from polyethylene glycol sorbitan monolaurate, polyethylene glycol p-(1,1,3,3-tetramethylbutyl)-phenyl ether), polyoxyethyleneglycol dodecyl ether, or a combination thereof.

26. The composition of claim 25, comprising:
0.02 M to 0.5 M borate buffer;
0.5 wt % to 1.1 wt % protein and/or protein hydrolysate;
38 mM to 75 mM alkyl amine;
0.05 wt % to 0.1 wt % azide preservative; and
0.005 wt % to 0.01 wt % glycol surfactant.

* * * * *

UNITED STATES PATENT AND TRADEMARK OFFICE
CERTIFICATE OF CORRECTION

Page 1 of 1

PATENT NO. : 8,877,505 B2
APPLICATION NO. : 13/382509
DATED : November 4, 2014
INVENTOR(S) : May et al.

It is certified that error appears in the above-identified patent and that said Letters Patent is hereby corrected as shown below:

In the Claims:

Claim 8, column 41, line 63, "0.7-%" should read – 0.7% –

Claim 10, column 42, line 3, "p-(1,1,3,3-tetramethylbutyl)-phenyl ether)" should read – p-(1,1,3,3-tetramethylbutyl)-phenyl ether –

Claim 24, column 44, line 11, "-OH, -CO$_2$R$_1$, -CN" should read – -OH, -OR$_1$, -CO$_2$R$_1$, -CN –

Claim 25, column 44, lines 33-34, "p-(1,1,3,3-tetramethylbutyl)-phenyl ether)" should read – p-(1,1,3,3-tetramethylbutyl)-phenyl ether –

Signed and Sealed this
Twenty-third Day of February, 2016

Michelle K. Lee
*Director of the United States Patent and Trademark Office*